US010137264B2

(12) United States Patent
Darby et al.

(10) Patent No.: US 10,137,264 B2
(45) Date of Patent: Nov. 27, 2018

(54) RESPIRATORY ASSISTANCE APPARATUS

(71) Applicant: Fisher & Paykel Healthcare Limited, Auckland (NZ)

(72) Inventors: Adam John Darby, Auckland (NZ); Donald Roy Kuriger, Auckland (NZ); Johannes Nicolaas Bothma, Otorohanga (NZ); Scott Bent, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 910 days.

(21) Appl. No.: 14/376,381

(22) PCT Filed: Feb. 1, 2013

(86) PCT No.: PCT/NZ2013/000006
§ 371 (c)(1),
(2) Date: May 6, 2015

(87) PCT Pub. No.: WO2014/007655
PCT Pub. Date: Jan. 9, 2014

(65) Prior Publication Data
US 2015/0157818 A1   Jun. 11, 2015
US 2017/0151401 A9   Jun. 1, 2017

Related U.S. Application Data

(63) Continuation-in-part of application No. 14/131,725, filed as application No. PCT/NZ2012/000124 on Jul. 13, 2012.
(Continued)

(51) Int. Cl.
*A61M 16/00* (2006.01)
*A61M 16/06* (2006.01)
(Continued)

(52) U.S. Cl.
CPC .... *A61M 16/0066* (2013.01); *A61M 16/0003* (2014.02); *A61M 16/0051* (2013.01);
(Continued)

(58) Field of Classification Search
CPC .......... A61M 16/0066; A61M 16/0069; A61M 16/06–16/0694; F04D 29/281–29/283; F04D 29/30
See application file for complete search history.

(56) References Cited

U.S. PATENT DOCUMENTS 2,929,944 A  *  3/1960  Shewmon .............. H02K 15/16
                                                              310/51
4,161,667 A      7/1979  Buckman
(Continued)

FOREIGN PATENT DOCUMENTS

CN         1266150 A       9/2000
CN       101296722 A      10/2008
(Continued)

OTHER PUBLICATIONS

European Search Report; dated Jul. 20, 2015; 13 pages.
(Continued)

*Primary Examiner* — Valerie L Woodward
(74) *Attorney, Agent, or Firm* — Knobbe, Martens, Olson & Bear, LLP

(57) ABSTRACT

A head-mounted respiratory assistance apparatus configured to provide a respiratory gases stream to a user. The head-mounted respiratory assistance has a main body securable to the head of a user and a blower unit that is operable to generate a pressurized gases stream from a supply of gases from the surrounding atmosphere. A patient interface is provided on the main body that has a gases inlet which is fluidly connected to the blower unit and which is configured to deliver the pressurized gases to the user's nose and/or mouth.

20 Claims, 42 Drawing Sheets

Related U.S. Application Data

(60) Provisional application No. 61/594,258, filed on Feb. 2, 2012, provisional application No. 61/719,726, filed on Oct. 29, 2012, provisional application No. 61/738,910, filed on Dec. 18, 2012, provisional application No. 61/507,384, filed on Jul. 13, 2011.

(51) Int. Cl.

| | |
|---|---|
| A61M 16/10 | (2006.01) |
| F04D 29/02 | (2006.01) |
| F04D 29/28 | (2006.01) |
| F04D 29/30 | (2006.01) |
| A61M 16/16 | (2006.01) |
| F04D 25/08 | (2006.01) |
| F04D 29/053 | (2006.01) |

(52) U.S. Cl.
CPC ...... *A61M 16/0069* (2014.02); *A61M 16/024* (2017.08); *A61M 16/06* (2013.01); *A61M 16/0616* (2014.02); *A61M 16/0633* (2014.02); *A61M 16/0683* (2013.01); *A61M 16/1045* (2013.01); *F04D 29/023* (2013.01); *F04D 29/281* (2013.01); *F04D 29/30* (2013.01); A61M 16/107 (2014.02); A61M 16/161 (2014.02); A61M 2016/0021 (2013.01); A61M 2016/0033 (2013.01); A61M 2205/33 (2013.01); A61M 2205/332 (2013.01); A61M 2205/3561 (2013.01); A61M 2205/3592 (2013.01); A61M 2205/505 (2013.01); A61M 2205/8206 (2013.01); A61M 2205/8243 (2013.01); A61M 2205/8262 (2013.01); A61M 2205/8268 (2013.01); A61M 2209/086 (2013.01); A61M 2209/088 (2013.01); A61M 2210/06 (2013.01); A61M 2210/0618 (2013.01); A61M 2210/0625 (2013.01); A61M 2230/10 (2013.01); F04D 25/08 (2013.01); F04D 29/053 (2013.01); F05D 2260/96 (2013.01); F05D 2300/43 (2013.01)

(56) References Cited

U.S. PATENT DOCUMENTS

| | | | |
|---|---|---|---|
| 4,233,972 A | 11/1980 | Hauff et al. | |
| 4,357,552 A | 11/1982 | MacMillan | |
| 4,590,951 A | 5/1986 | O'Connor | |
| 5,211,171 A | 5/1993 | Choromokos | |
| 5,484,270 A | 1/1996 | Adahan | |
| 5,567,127 A | 10/1996 | Wentz | |
| 5,662,611 A | 9/1997 | Beiser et al. | |
| 5,797,727 A | 8/1998 | Peters et al. | |
| 5,875,783 A | 3/1999 | Kullik | |
| 5,967,764 A | 10/1999 | Booth et al. | |
| 6,050,262 A | 4/2000 | Jay | |
| 6,376,952 B1 | 4/2002 | Stenta | |
| 6,439,861 B1 | 8/2002 | Shieh | |
| 6,543,449 B1 | 4/2003 | Woodring et al. | |
| 6,622,724 B1 | 9/2003 | Truitt et al. | |
| 6,644,310 B1 | 11/2003 | Delache et al. | |
| 6,700,255 B1 | 3/2004 | Stenta | |
| 6,717,299 B2 | 4/2004 | Bacile et al. | |
| 6,722,359 B2 | 4/2004 | Chalvignac | |
| 6,802,648 B2 | 10/2004 | Merot et al. | |
| 6,910,483 B2 | 6/2005 | Daly et al. | |
| 7,244,099 B2 * | 7/2007 | Yamasaki | F04D 29/162 415/173.6 |
| 7,384,237 B2 | 6/2008 | Baecke et al. | |
| 7,448,383 B2 | 11/2008 | Delache et al. | |
| 7,516,743 B2 | 4/2009 | Hoffman | |
| 7,913,692 B2 * | 3/2011 | Kwok | A61M 16/06 128/206.21 |
| 8,011,362 B2 | 9/2011 | Adams | |
| 8,020,556 B2 | 9/2011 | Shahar | |
| 8,020,557 B2 * | 9/2011 | Bordewick | A61M 16/00 128/206.18 |
| 8,042,535 B2 | 10/2011 | Kenyon et al. | |
| 8,074,645 B2 | 12/2011 | Bordewick et al. | |
| 8,074,647 B2 | 12/2011 | Truitt et al. | |
| 8,122,884 B2 | 2/2012 | Daly et al. | |
| 8,375,944 B2 | 2/2013 | Kwok | |
| D688,788 S | 8/2013 | Spruell et al. | |
| 8,638,014 B2 | 1/2014 | Sears et al. | |
| 8,973,576 B2 * | 3/2015 | Kenyon | A61M 16/0066 128/204.18 |
| 9,132,250 B2 * | 9/2015 | Allum | A61M 16/00 |
| 9,132,252 B2 * | 9/2015 | Barlow | A61M 16/0066 |
| 2005/0188989 A1 | 9/2005 | Delache et al. | |
| 2005/0210622 A1 | 9/2005 | Baecke et al. | |
| 2006/0096596 A1 | 5/2006 | Occhialini et al. | |
| 2006/0237013 A1 | 10/2006 | Kwok | |
| 2007/0017518 A1 | 1/2007 | Farrugia et al. | |
| 2007/0251527 A1 | 11/2007 | Sleeper | |
| 2007/0277827 A1 | 12/2007 | Bordewick et al. | |
| 2007/0284952 A1 * | 12/2007 | Ihle | H02K 1/2733 310/43 |
| 2008/0149306 A1 | 6/2008 | Hwang et al. | |
| 2008/0178879 A1 | 7/2008 | Roberts et al. | |
| 2008/0216835 A1 | 9/2008 | McGinnis et al. | |
| 2009/0071480 A1 * | 3/2009 | Adams | A61M 16/0066 128/204.18 |
| 2009/0194101 A1 * | 8/2009 | Kenyon | A61M 16/0057 128/201.22 |
| 2009/0301485 A1 | 12/2009 | Kenyon et al. | |
| 2009/0315492 A1 | 12/2009 | Oomura | |
| 2009/0320842 A1 * | 12/2009 | Doherty | A61M 16/06 128/204.21 |
| 2010/0059055 A1 | 3/2010 | Brungart et al. | |
| 2010/0059056 A1 | 3/2010 | Sears et al. | |
| 2010/0132711 A1 | 6/2010 | Kenyon | |
| 2010/0170513 A1 * | 7/2010 | Bowditch | A61M 16/00 128/204.23 |
| 2011/0073110 A1 * | 3/2011 | Kenyon | A61M 16/0057 128/204.18 |
| 2011/0132363 A1 | 6/2011 | Chalvignac | |
| 2012/0000463 A1 | 1/2012 | Bordewick et al. | |
| 2012/0080032 A1 | 4/2012 | Bordewick et al. | |
| 2012/0097156 A1 | 4/2012 | Bowman et al. | |
| 2012/0138058 A1 | 6/2012 | Fu et al. | |
| 2012/0152255 A1 | 6/2012 | Barlow et al. | |
| 2012/0167879 A1 * | 7/2012 | Bowman | A61M 16/0066 128/201.22 |
| 2012/0266873 A1 * | 10/2012 | Lalonde | A61M 16/0057 128/201.13 |
| 2012/0285454 A1 | 11/2012 | Nibu et al. | |
| 2013/0098359 A1 * | 4/2013 | Becker | A61M 16/0666 128/201.13 |
| 2013/0152918 A1 * | 6/2013 | Rummery | A61M 16/00 128/201.22 |
| 2013/0306072 A1 * | 11/2013 | Moir | A61M 16/0066 128/204.18 |
| 2014/0069432 A1 | 3/2014 | Mebasser et al. | |
| 2014/0216460 A1 | 8/2014 | Bothma et al. | |
| 2014/0227091 A1 | 8/2014 | Kenyon et al. | |
| 2015/0328418 A1 | 11/2015 | Bothma et al. | |

FOREIGN PATENT DOCUMENTS

| | | |
|---|---|---|
| CN | 101321958 A | 12/2008 |
| CN | 101449064 A | 6/2009 |
| CN | 101466429 A | 6/2009 |
| DE | 3310376 A1 | 9/1984 |
| EP | 1035330 | 9/2000 |
| EP | 1205203 A2 | 5/2002 |
| EP | 1205203 A3 | 7/2002 |
| EP | 1 205 203 | 9/2004 |
| EP | 1205203 B1 | 9/2004 |
| EP | 2317150 A1 | 5/2011 |
| GB | 1041313 | 9/1966 |
| JP | 2002-511786 A | 4/2002 |

(56) References Cited

FOREIGN PATENT DOCUMENTS

| JP | 2004-353655 A | 12/2004 |
|---|---|---|
| JP | 2007-506482 A | 3/2007 |
| WO | WO 2007/048206 | 5/2007 |
| WO | WO 2007/134405 | 11/2007 |
| WO | WO 2008/028247 | 3/2008 |
| WO | WO 2008/092235 | 8/2008 |
| WO | WO 2010/028121 | 3/2010 |
| WO | WO 2010/096467 A1 | 8/2010 |
| WO | WO 2011/017763 | 2/2011 |
| WO | WO 2011/022779 | 3/2011 |
| WO | WO 2011/062633 | 5/2011 |
| WO | WO 2011/112807 | 9/2011 |
| WO | WO 2012/024740 | 3/2012 |
| WO | WO 2012/094230 | 7/2012 |
| WO | WO 2012/113027 | 8/2012 |
| WO | WO 2012/145358 | 10/2012 |
| WO | WO 2012/174602 | 12/2012 |
| WO | WO 2013/020167 | 2/2013 |

OTHER PUBLICATIONS

China First Office Action; 201280034511.4; dated Jul. 29, 2015; 28 pages.

China First Office Action; 201380018302.5; dated Nov. 4, 2015; 9 pages.

Sep. 24, 2013 International Search Report and Written Opinion for Application No. PCT/NZ2013/000006 filed on Feb. 1, 2013.

Sep. 24, 2013 Written Opinion for Application No. PCT/NZ2013/000006 filed on Feb. 1, 2013.

Extended European Search Report for European Patent Application No. 17157168.0, dated Jun. 12, 2016, in 7 pages.

International Search Report; PCT/IB2013/060549; dated Mar. 19, 2014; 5 pages.

Written Opinion; PCT/IB2013/060549, dated Mar. 19, 2014; 6 pages.

Japanese Examination Report with English Translation, dated Dec. 19, 2016; 8 pages.

International Search Report; PCT/NZ2012/000124; dated Oct. 29, 2012; 6 pages.

Written Opinion; PCT/NZ2012/000124; dated Oct. 29, 2012; 9 pages.

Examination Report for Australian Application No. 2017204037, dated Nov. 16, 2017; 3 pages.

Examination Report No. 2 for Australian Application No. 2017204037, dated Jan. 3, 2018; 2 pages.

\* cited by examiner

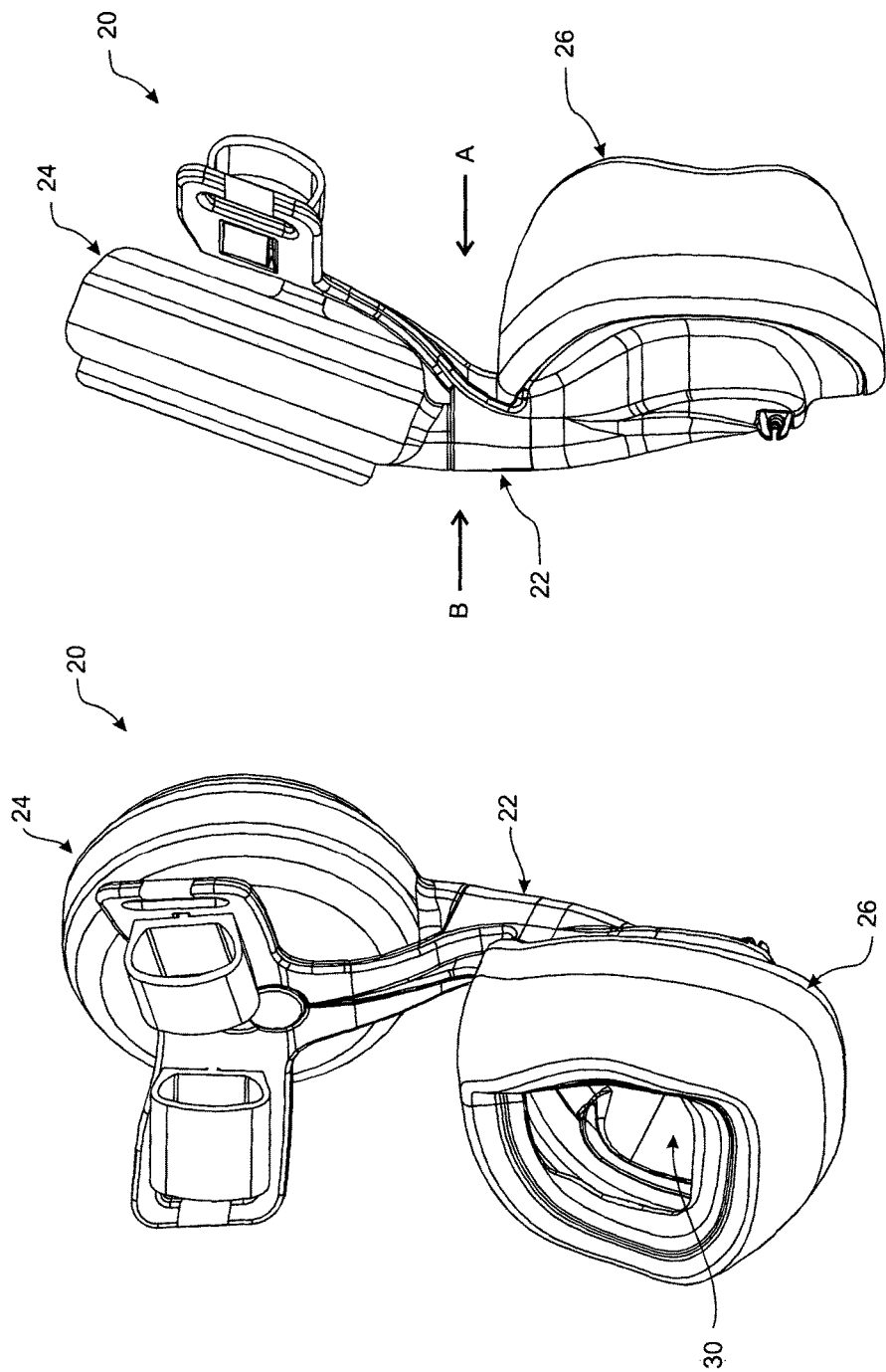

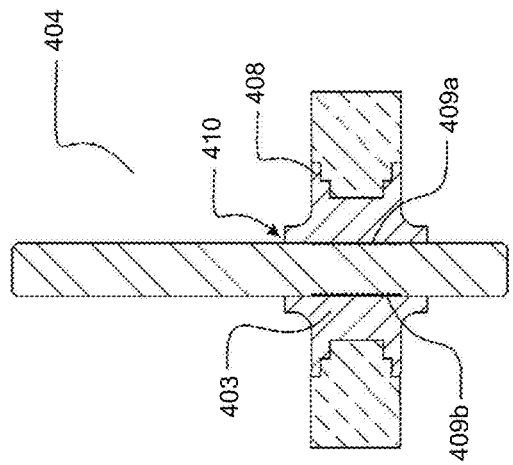
FIGURE 33B1
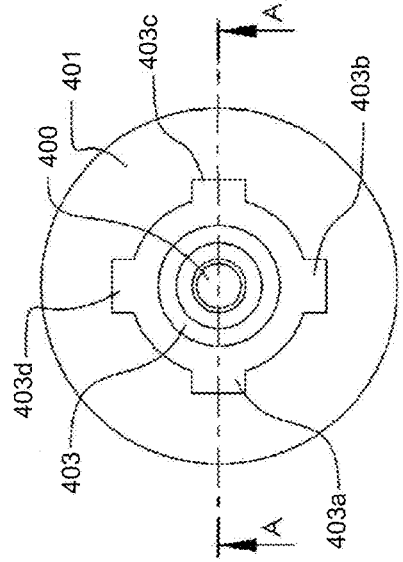
FIGURE 33B3
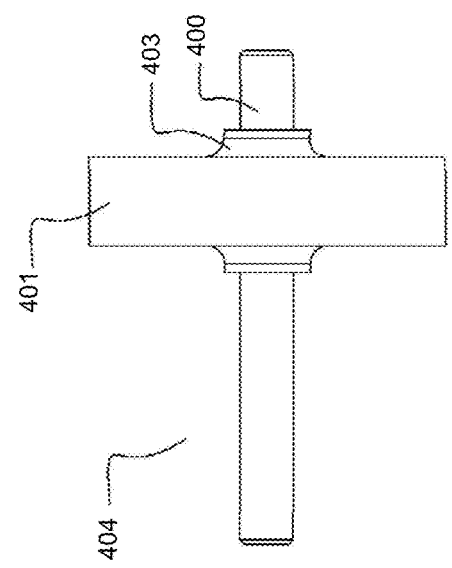
FIGURE 33B2

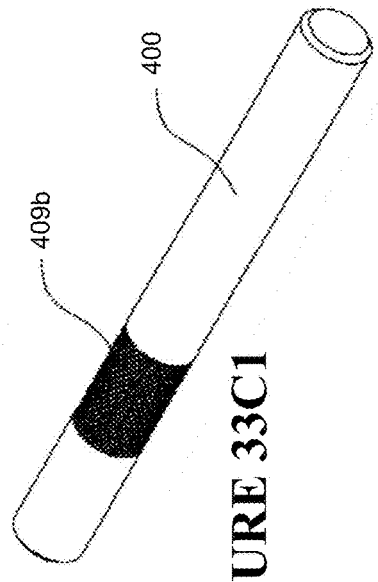
FIGURE 33C1
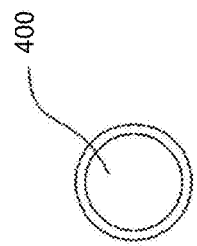
FIGURE 33C3
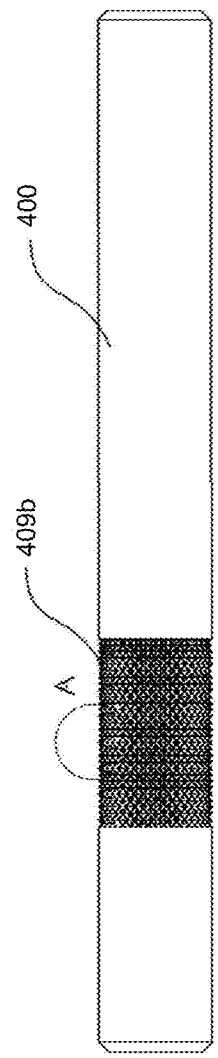
FIGURE 33C2
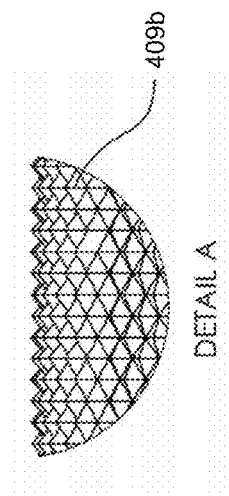
DETAIL A
FIGURE 33C4

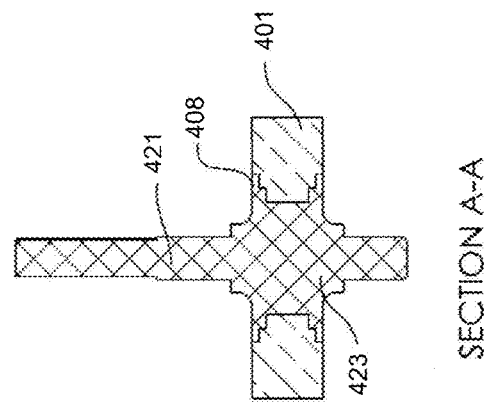
FIGURE 33D4
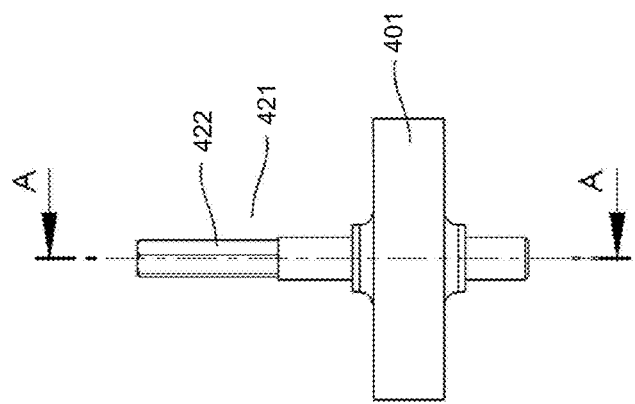
FIGURE 33D3
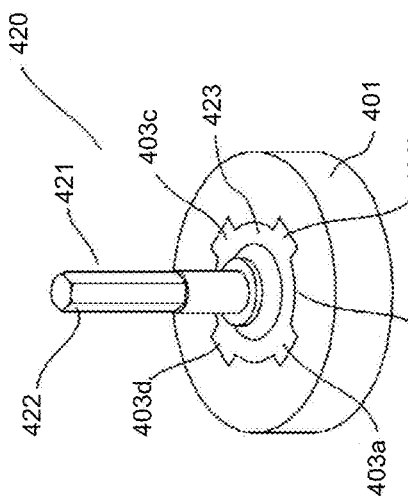
FIGURE 33D1
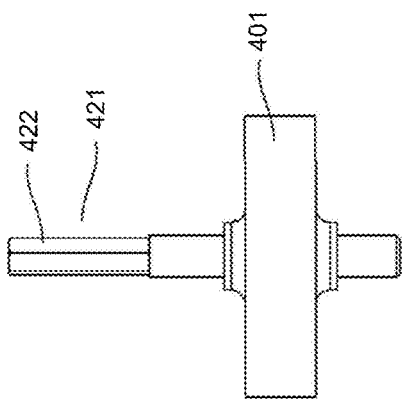
FIGURE 33D2

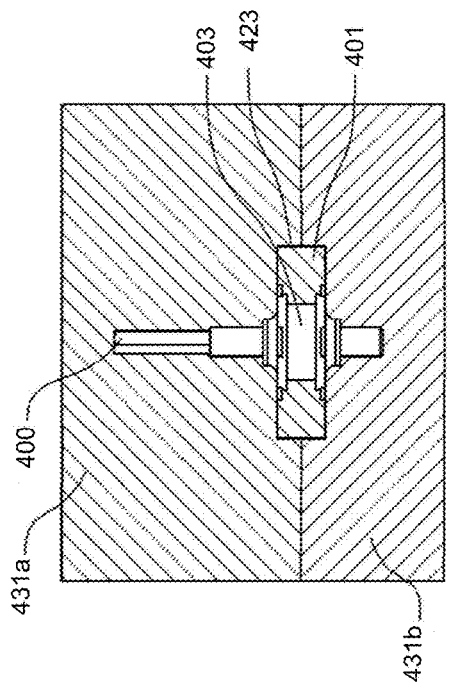
FIGURE 33F1
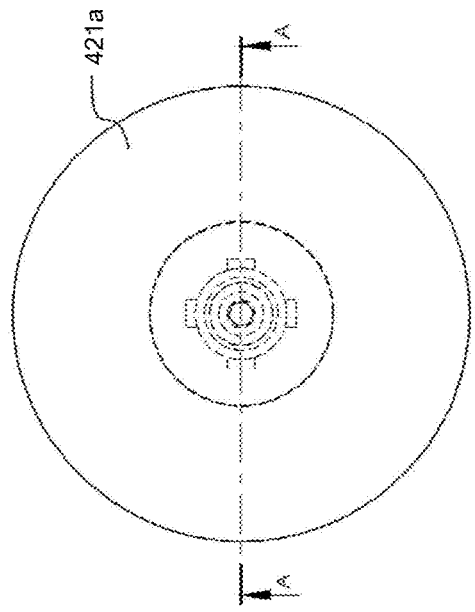
FIGURE 33F3
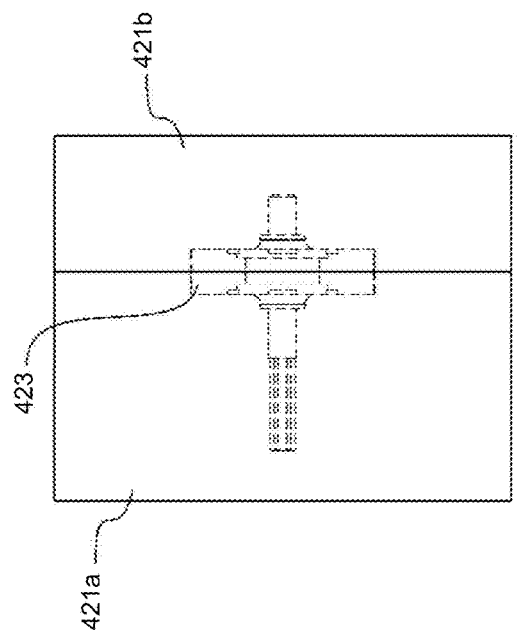
FIGURE 33F2

RESPIRATORY ASSISTANCE APPARATUS

FIELD OF THE INVENTION

This invention relates to a respiratory assistance apparatus that provides a stream of gases to a user for therapeutic purposes. In particular, although not exclusively, the respiratory assistance apparatus may provide respiratory assistance to patients or users who require a supply of gases for respiratory therapies such as Positive Airway Pressure (PAP) therapies, including but not limited to Continuous Positive Airway Pressure (CPAP) therapy, Bi-level Positive Airway Pressure (Bi-PAP) therapy, and Oral Positive Airway Pressure (OPAP) therapy, and which are typically used for the treatment of diseases such as Obstructive Sleep Apnea (OSA), snoring, or Chronic Obstructive Pulmonary Disease (COPD).

BACKGROUND OF THE INVENTION

Respiratory or breathing assistance devices or systems for providing a flow of humidified and heated gases to a patient for therapeutic purposes are well known in the art. Systems for providing therapy of this type (for example respiratory humidification) typically have a structure where gases are delivered to a humidifier chamber from a gases source, such as a blower (also known as a compressor, an assisted breathing unit, a fan unit, a flow generator or a pressure generator). As the gases pass over the hot water, or through the heated and humidified air in the humidifier chamber, they become saturated with water vapour. The heated and humidified gases are then delivered to a user or patient downstream from the humidifier chamber, via a patient interface comprising a flexible gases conduit and a patient interface.

In one form, such respiratory assistance systems can be modular systems that comprise a humidifier unit and a blower unit that are separate (modular) items. The modules are connected in series via connection conduits to allow gases to pass from the blower unit to the humidifier unit. For example, FIG. 1 shows a schematic view of a user 1 receiving a stream of heated and humidified air from a modular respiratory assistance system. Pressurised air is provided from an assisted breathing unit or blower unit 2a via a connector conduit 7 to a humidifier chamber 4a. The stream of humidified, heated and pressurised air exits the humidification chamber 4a via a flexible hose or gases conduit 3, and is provided to the patient or user 1 via a patient interface 5.

In an alternative form, the respiratory assistance systems can be integrated systems in which the blower unit and the humidifier unit are contained within the same housing. A typical integrated system consists of a main blower unit or assisted breathing unit which provides a pressurised gases flow, and a humidifier unit that mates with or is otherwise rigidly connected to the blower unit. FIG. 2 shows a schematic view of the user 1 receiving heated and humidified air from an integrated respiratory assistance system 6. The system operates in the same manner as the modular system shown in FIG. 1, except the humidification chamber 4b has been integrated with the blower unit to form the integrated system 6.

The patient interface 5 shown in FIGS. 1 and 2 is a nasal mask, covering the nose of the user 1. However, it should be noted that in systems of these types, a mask that covers the mouth and nose, a full face mask, a nasal cannula, or any other suitable patient interface could be substituted for the nasal mask shown. A mouth-only interface or oral mask could also be used. Also, the patient or user end of the conduit can be connected to a tracheostomy fitting, or an endotracheal intubation.

Impeller type fans or blowers are most commonly used in respiratory assistance systems of this type. An impeller blade unit is contained within an impeller housing. The impeller blade unit is connected to a drive of some form by a central spindle. A typical impeller housing is shown in FIGS. 3 and 4. A typical rotating impeller unit 10, having a plurality of blades 11 and a shroud 12, which in use is located inside the housing is shown in FIGS. 5 and 6. Air is drawn into the centre of the impeller unit through an aperture, and is then forced outwards from the centre of the housing towards an exit passage (usually located to one side of the housing) by the blades of the rotating impeller unit. The blades 11 are coupled to the central spindle 13, which is rotated by a motor for example.

The respiratory assistance systems of the type described above typically present various problems or challenges to the manufacturer from a design viewpoint, some of which are briefly outlined below.

Effective respiratory therapy often requires a user to use respiratory assistance systems of the type described above on a daily basis for long periods of time. For the treatment of OSA, the user needs to use the respiratory assistance system at night when they are asleep. Patient comfort and convenience when using such respiratory assistance systems is paramount to compliant and effective treatment. Mask leaks are a common complaint of user's of the above type of respiratory assistance systems. Mask leaks are typically caused by the flexible gases conduit 3 tugging on the patient interface or mask 5 when the user moves in their sleep.

Most respiratory assistance systems of the type described above for treating OSA with PAP therapy provide a gas supply to the patient interface but have no return path for gases from the interface. To eliminate the build-up of carbon dioxide in the patient interface, the patient interface requires a gas washout vent for venting exhaled gases to atmosphere, and this is often referred to as the 'bias flow'. The bias flow represents a loss in the gases supply circuit and the blower unit must have a motor that is powerful enough to maintain the bias flow while also generating the desired gas pressure at the patient interface. The gas washout vent can also become a source of noise and a source of discernable draughts. Excessive noise can be irritating for the patient and their bed partner. Depending on their location, draughts can also be annoying to the patient.

Humidification of the gases in the respiratory assistance systems also adds to the design complexity. For example, heating of the gases conduit 3 of the patient interface is often required to prevent condensation forming in the gases conduit.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved respiratory assistance apparatus, or to at least provide the public with a useful choice.

SUMMARY OF THE INVENTION

In a first aspect, the invention broadly consists in a head-mounted respiratory assistance apparatus configured to provide a respiratory gases stream to a user, comprising: a main body securable to the head of a user; a blower unit provided on the main body having a gases inlet to receive a supply of gases from the surrounding atmosphere and which is operable to generate a pressurised gases stream at a gases outlet; and a patient interface provided on the main body having a gases inlet which is fluidly connected via a gases flow path to the gases outlet of the blower unit and which is configured to deliver the pressurised gases to the user's nose and/or mouth via one or more gases outlets, and wherein the gases flow path from the gases inlet of the blower unit to the gases outlet(s) of the patient interface is substantially sealed such that there is zero bias flow along the gases flow path, and wherein the blower unit comprises a lightweight impeller, and a motor with a rotatable drive shaft that is configured to rotate the impeller.

Preferably, the apparatus may be configured to passively humidify and warm the pressurised respiratory gases in the gases flow path via accumulated heat and moisture build up within at least a portion of the gases flow path. In one form, the gases flow path may be configured to accumulate heat and moisture build-up within at least a portion of the air flow path from exhaled gases from the user flowing back into the gases flow path from the patient interface.

Preferably, the apparatus may further comprise one or more heat and moisture exchangers (HMEs) in the gases flow path of the respiratory assistance apparatus.

Preferably, the gases or air flow path is provided through the respiratory device between the gases inlet of the blower unit and an outlet or opening of the patient interface.

Preferably, excess exhaled gases from the user may vent back through the air flow path in the opposite direction of the pressurised gases stream and exit the respiratory assistance apparatus into the atmosphere from the gases inlet of the blower unit. Preferably, the gases flow path volume or 'deadspace' between the gases inlet of the blower unit and the gases outlet(s) of the patient interface may be less than approximately 200 mL, and more preferably in the range of approximately 50 mL to approximately 150 mL.

Preferably, the apparatus may be configured to be operatively connectable to a separate base station, the base station comprising: a power supply system that is operable to supply power to the respiratory assistance apparatus; a data transfer system that is operable to send and receive data to and from the respiratory assistance apparatus; and a control system that is operable to control the respiratory assistance apparatus via control signals.

Preferably, the apparatus may further comprise headgear that is configured to secure or mount the main body to the head of a user, the headgear comprising one or more headstraps. In one form, the headgear may comprise an upper headstrap that is connected to an upper part of the respiratory assistance apparatus and is configured to extend around an upper part of the user's head; and a lower headstrap that is connected to a lower part of the respiratory assistance apparatus and is configured to extend around a lower part of the user's head, and wherein the headgear is configured to locate the main body of the respiratory assistance apparatus in the region of user's face.

In one form, the headgear may be fully flexible or formed substantially from flexible components. In another form, the headgear may be semi-rigid in that it may comprise one or more rigid components, such as but not limited to the various headgear embodiments described in published patent application WO2012/140514, the contents of which are herein incorporated by reference.

Preferably, the respiratory assistance apparatus may comprise one or more onboard power supply modules that are configured to supply power to the apparatus, and wherein the power supply modules are mounted to or integrated with the headgear. Alternatively, the power supply modules may be otherwise head-mounted with the respiratory assistance apparatus, such as mounted to or integrated with the main body or blower unit of the respiratory assistance apparatus. Preferably, the power supply modules are connected to the respiratory assistance apparatus by a power cable or cables. In one form, the power supply module(s) may be detachable or releasable from the respiratory assistance apparatus.

Alternatively or additionally, the power supply module(s) may be a separate non-head-mounted portable module that is connected to the respiratory device by a power cable. Alternatively or additionally, the respiratory assistance apparatus may be configured to connect to an AC power adaptor for a supply of power.

In one form, one or more pockets are provided within the headstrap(s) within which the one or more power supply module(s) are retained. Preferably, the pocket(s) may be openable to enable removal of the power supply module(s). In another form, the power supply module(s) may be releasably mounted to a part of the headgear such that they are detachable from the headgear. In another form, the power supply module(s) may be provided within a flexible package secured to the headgear and which is configured to extend at least partially over the top of the user's head. Preferably, the flexible package may be secured to one or more of the headstraps of the headgear by a base layer of flexible material.

Preferably, the headgear may further comprise one or more shielding plates located between the one or more power supply modules and the surface of the user's head when the headgear is worn by a user.

Preferably, the power supply module(s) comprise any one or more energy storage devices selected from the following: batteries or battery packs (rechargeable or disposable), fuel cells, and/or capacitors.

Preferably, the lightweight impeller of the blower unit may be shroudless or otherwise have reduced material.

In one embodiment, a distal end of the impeller blades curve in the direction of blade rotation. In another embodiment, the impeller blades curve in the opposite direction of blade rotation.

In some embodiments, the impeller is formed in one piece.

In some embodiments, the impeller comprises a radius of between 15 and 60 mm.

In some embodiments, the impeller has a mass of less than 2 grams and preferably between 0.8 and 1.8 grams.

In some embodiments, the impeller is configured to have a pressure to inertia to radius ratio greater than 50:1 Pa per gram*mm, and preferably greater than 80:1 Pa per gram*mm.

In some embodiments, the impeller is configured to have a moment of inertia to radius ratio less than 15 g*mm and preferably within the range of 8 to 12 g*mm.

In some embodiments, the impeller is configured to have a blade sweep volume to a blade volume ratio of 16:1 or greater.

Preferably, the blower unit may further comprise a casing having upper and lower internal surfaces that enclose the impeller, and wherein the impeller has a plurality of blades that are substantially open to the upper and lower internal surfaces of the casing by virtue of being shroudless or otherwise having reduced material. In one form, the casing forms part of or is integrated with the respiratory assistance apparatus.

Preferably, the blower unit may further comprise a partition to define first and second interior regions within the casing, the first region being defined by the casing and the partition and comprising the gases inlet and motor, the second region being defined by the casing and the partition and comprising the impeller, and wherein the first and second regions are fluidly connected by an opening formed in or by the partition.

Preferably, the impeller may have an axis of rotation, the partition extending radially from the axis of rotation.

Preferably, the casing of the blower unit may further comprise a volute that is fluidly connected to the second region by an air passage, and wherein the gases outlet of the blower unit is proximate the periphery of the volute.

In a first form, the blower unit may comprise a motor comprising: a stator, and at least one bearing structure to support the rotatable drive shaft within the stator, the bearing structure comprising one or more bearings that are supported by one or more bearing mounts about the axis of the rotatable drive shaft. Preferably the bearing mount(s) provide compliant support to the rotatable shaft.

Preferably, the stator may comprise a stator frame, and an outer portion of the one or more bearing mounts engages the stator and/or an inner surface of the stator frame. In one form, an outer portion of the one or more bearing mounts engages the stator and/or a stator frame and/or other structure.

Preferably, the blower unit may further comprise a motor mount that couples the stator and the casing to provide compliant support to the motor.

Preferably the bearing mount and/or motor mount are flexible and/or resilient.

Preferably the bearing mount is made from a material that provides resilience and/or flexibility to provide preload when in the engaged configuration.

Preferably the bearing mounts are made from a material that provides damping.

Preferably, the bearing mounts may be flexible and/or resilient, and wherein the bearing mounts may have a curved annular body and when engaged with the stator and/or stator frame the annular body is coerced into an engaged configuration that provides preload to the one or more bearings.

Preferably the motor is operated using field oriented control.

In one form, the rotatable drive shaft may be plastic. Preferably, the motor may further comprise a rotor within the stator, and wherein the plastic rotatable drive shaft is formed and coupled to the rotor by injection moulding. In one form, Preferably the motor comprises a plastic rotatable shaft extending through an opening in a magnet rotor and being coupled thereto.

Also described is a method of manufacturing a shaft and rotor assembly for a motor comprising: inserting a rotor with a central opening into a first mould part, supporting a shaft extended through the central opening, coupling a second mould part to the first mould part to create a mould cavity around the central opening, injection moulding a plastic insert between the plastic shaft and the central opening to couple the plastic shaft to the rotor.

Also described is a method of manufacturing a shaft and rotor assembly for a motor comprising: inserting a rotor with a central opening into a first mould part, coupling a second mould part to the first mould part to create a mould cavity around the central opening, injection moulding a plastic shaft that extends through and couples to the central opening of the rotor.

In a second form, the blower unit comprises: a motor comprising a rotatable shaft located within a stator, a bearing structure to support the rotatable shaft in the stator, the bearing structure having one or more bearing mounts.

In a third form, the blower unit may comprise: a centrifugal impeller driven by a motor within a casing, the casing having a gases inlet, a gases outlet and a partition (or divider) to define first and second interior regions wherein the first and second regions are fluidly connected by an opening in the partition.

In a fourth form, the blower unit may comprise: a motor with a rotatable shaft and at least one bearing structure to support the rotatable shaft within a stator, the bearing structure having one or more flexible and/or resilient bearing mounts to provide compliance and/or preload and/or damping for the rotatable shaft, a lightweight impeller coupled to the rotatable shaft, a flexible and/or resilient motor mount that couples the stator and the housing to provide compliance and/or damping for the motor a partition to define first and second interior regions within the housing, wherein the first and second regions are fluidly connected by opening formed in or by the partition.

In a fifth form, the blower unit comprises: a gases inlet, a gases outlet, a motor with a shaft, and a lightweight impeller connected to the motor and rotatable to draw gases from the inlet and emit gases through the outlet, wherein the impeller is shroudless or otherwise has reduced material.

Each of the forms of the blower unit may additionally comprise any one or more features mentioned in respect to the other forms of the blower unit.

Preferably, the respiratory assistance apparatus comprises an operable control system having an onboard controller that is configured to control the blower unit to deliver the pressurised gases stream to the user at the desired pressure and/or flow rate during the user's breathing cycle. By way of example, the apparatus may comprise an onboard electronic controller that is mounted to or within the respiratory assistance apparatus and which is operable to control the pressure of respiratory gases delivered to the user by controlling the motor speed within the blower unit.

Preferably, the apparatus may further comprise one or more sensors mounted to or within the respiratory assistance apparatus that are configured to sense operational parameters and generate representative sensor signals for sending to the controller.

Preferably, the apparatus may further comprise an onboard wireless power transfer receiver that is configured to receive power from a wireless power transfer transmitter.

Preferably, the apparatus may further comprise an onboard power supply module.

In one form, the blower unit may be releasably mounted to the main body. In another form, the blower unit may be integrated with or fixed to the main body.

In one form, the main body may comprise: a forehead support member that is configured to engage with the user's forehead; a mask body for receiving a mask seal assembly of the patient interface; a connecting member extending between the forehead support member and mask body, and a gases inlet that is fluidly connected to the gases outlet of the blower unit. Preferably, the forehead support member of the main body may be horizontally oriented and the connecting member extends centrally from the forehead support member in a vertical orientation such that the members together form a T-shaped part (or T-piece), and wherein the blower unit is mounted to the T-shaped part. In one form, the blower unit may be provided on or may be mounted to the forehead support member of the main body such that it is located in the user's forehead region when in use.

In one form, the apparatus is configured as a positive airway pressure (PAP) device. For example, the apparatus may be configured to operate as a CPAP device, Bi-PAP device, or any other PAP device.

In one form, the patient interface is releasably mounted to the main body. In another form, the patient interface is integrated with or fixed to the main body.

In one form, the patient interface may comprise a nasal mask that is configured to sealingly engage with the user's face so as to cover their nose.

In another form, the patient interface may comprise any one of the following: a full face mask configured to sealingly engage with the user's face so as to cover their nose and mouth; a nasal pillows mask that sealingly engages the user's nostrils; an unsealed nasal cannula that is configured to be positioned inside the user's nostrils; or an oral interface that is configured to sealingly engage with or within the user's mouth.

Preferably, the main body may further comprise a gases passage or conduit that fluidly connects the gases outlet of the blower unit to the gases inlet of the patient interface, and wherein the gases passages forms part of the gases flow path.

In one form, the main body may be configured to mount or locate the blower unit in the forehead region of the user's face and patient interface in the nose and/or mouth region of the user's face, when the apparatus is worn in use. Alternatively, the blower unit may be fixedly or releasably mounted to the front of the patient interface (e.g. mask).

In a second aspect, the invention broadly consists in a base station that is operatively connectable to a head-mounted respiratory assistance apparatus configured to provide a respiratory gases stream to a user, the head-mounted respiratory assistance apparatus comprising: a main body securable to the head of a user; a blower unit provided on the main body having a gases inlet to receive a supply of gases from the surrounding atmosphere and which is operable to generate a pressurised gases stream at a gases outlet; and a patient interface provided on the main body having a gases inlet which is fluidly connected via a flow path to the gases outlet of the blower unit and which is configured to deliver the pressurised gases to the user's nose and/or mouth via one or more gases outlets, the base station comprising: a power supply system that is operable to supply power to the respiratory assistance apparatus; a data transfer system that is operable to send and receive data to and from the respiratory assistance apparatus; and a control system that is operable to control the respiratory assistance apparatus via control signals.

In one form, the power supply system may be configured to transfer power to the respiratory assistance apparatus via one or more power transfer cables.

In another form, the power supply system may comprise wireless power transfer circuitry that is configured to transfer power to the respiratory assistance apparatus wirelessly.

Preferably, the data transfer system may comprise a first communication module that is operable to transfer data between the base station and the respiratory assistance apparatus over a wired or wireless communication medium.

Preferably, the data transfer system may further comprise a second communication module that is operable to transfer data between the base station and an external server over a wired or wireless communication medium.

Preferably, the control system may be operable to send control signals to the respiratory assistance apparatus to control any one or more of the following operational modes: on/off mode, charging mode, drying mode, and/or data transfer mode.

In one form, the control system may be configured to automatically send control signals to the respiratory assistance apparatus to control one or more operational modes based on whether an operative connection between the base station and the respiratory assistance apparatus is detected.

In a third aspect, the invention broadly consists in a respiratory assistance system comprising: a head-mounted respiratory assistance apparatus configured to provide a respiratory gases stream to a user, the head-mounted respiratory assistance apparatus comprising: a main body securable to the head of a user; a blower unit provided on the main body having a gases inlet to receive a supply of gases from the surrounding atmosphere and which is operable to generate a pressurised gases stream at a gases outlet; and a patient interface provided on the main body having a gases inlet which is fluidly connected via a flow path to the gases outlet of the blower unit and which is configured to deliver the pressurised gases to the user's nose and/or mouth via one or more gases outlets; and a wireless power supply system that is configured to supply power wirelessly to the respiratory assistance apparatus.

Preferably, the wireless power supply may be configured to supply power to the respiratory assistance apparatus for powering of the blower unit.

Preferably, the respiratory assistance apparatus may comprise one or more sensors that are configured to sense various operational parameters and generate representative sensor signals, and wherein the wireless power supply is configured to supply power to the sensors.

In a fourth aspect, the invention broadly consists in a respiratory assistance system comprising: a head-mounted respiratory assistance apparatus configured to provide a respiratory gases stream to a user, the head-mounted respiratory assistance apparatus comprising: a main body securable to the head of a user; a blower unit provided on the main body having a gases inlet to receive a supply of gases from the surrounding atmosphere and which is operable to generate a pressurised gases stream at a gases outlet; and a patient interface provided on the main body having a gases inlet which is fluidly connected via a flow path to the gases outlet of the blower unit and which is configured to deliver the pressurised gases to the user's nose and/or mouth via one or more gases outlets; and one or more wireless sensors mounted to or within the respiratory assistance apparatus that are configured to sense operational parameters and generate representative sensor signals.

Preferably, the one or more wireless sensors may be configured to transmit, directly or indirectly, the generated sensor signals wirelessly to a separate external device or system.

Preferably, the one or more wireless sensors may be powered wirelessly by a wireless power transfer system that is wirelessly connected to the respiratory assistance apparatus In a fifth aspect, the invention broadly consists in a respiratory assistance system comprising: a head-mounted respiratory assistance apparatus configured to provide a respiratory gases stream to a user, the head-mounted respiratory assistance apparatus comprising: a main body securable to the head of a user; a blower unit provided on the main body having a gases inlet to receive a supply of gases from the surrounding atmosphere and which is operable to generate a pressurised gases stream at a gases outlet; and a patient interface provided on the main body having a gases inlet which is fluidly connected via a flow path to the gases outlet of the blower unit and which is configured to deliver the pressurised gases to the user's nose and/or mouth via one or more gases outlets; and a wireless communication module onboard the respiratory assistance apparatus that is operable to receive and send data to external devices and/or systems.

Preferably, the respiratory assistance apparatus comprises one or more sensors that may be configured to sense operational parameters and generate representative sensor signals, and wherein the communication module is configured to send the generated sensor signals to a separate external device or system.

Preferably, the respiratory assistance apparatus may comprises an onboard electronic controller that is configured to store usage data indicative of the user's use of the respiratory assistance apparatus, and wherein the communication module is configured to transfer the usage data wirelessly to a separate external device or system.

In a sixth aspect, the invention broadly consists in a head-mounted respiratory assistance apparatus configured to provide a respiratory gases stream to a user, the head-mounted respiratory assistance apparatus comprising: a main body securable to the head of a user; a blower unit provided on the main body having a gases inlet to receive a supply of gases from the surrounding atmosphere and which is operable to generate a pressurised gases stream at a gases outlet; a patient interface provided on the main body having a gases inlet which is fluidly connected via a flow path to the gases outlet of the blower unit and which is configured to deliver the pressurised gases to the user's nose and/or mouth via one or more gases outlets; and a head-mounted power supply that is configured to supply power to the respiratory device.

In another aspect, also described is a head-mounted respiratory assistance apparatus configured to provide a respiratory gases stream to a user, comprising: a main body securable to the head of a user; a blower unit provided on the main body having a gases inlet to receive a supply of gases from the surrounding atmosphere and which is operable to generate a pressurised gases stream at a gases outlet; and a patient interface provided on the main body having a gases inlet which is fluidly connected to the gases outlet of the blower unit and which is configured to deliver the pressurised gases to the user's nose and/or mouth.

In some embodiments, the respiratory assistance apparatus may be configured to provide a bias flow and may comprise one or more gas washout vents in the vicinity of the patient interface through which a portion of exhaled gases may exit the respiratory assistance apparatus. In other embodiments, the respiratory assistance apparatus may be configured to have zero bias flow.

In another aspect, also described is a respiratory assistance system comprising: a head-mounted respiratory assistance apparatus according to any of the above aspects; and a base station that is configured to receive and retain the respiratory assistance apparatus when not in use.

Each aspect of the invention above may additionally have any one or more of the features mentioned in respect of the other aspects.

The phrase "bias flow" as used in this specification and claims is intended to mean, unless the context suggests otherwise, the deliberate or controlled leak or flow of gases from the respiratory assistance apparatus to the surrounding atmosphere from one or more gas flushing vents or gas washout vents provided on the respiratory assistance apparatus and which are fluidly connected with or provided at or along a portion of the air or gases flow path within the apparatus.

The phrases "zero bias flow" or "zero bias" as used in this specification and claims is intended to mean, unless the context suggests otherwise, nil bias flow or in some embodiments minimal bias flow of not greater than 5 liters per minute.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 9 shows a lower perspective view of the rear side of the respiratory assistance apparatus of FIG. 7;

FIG. 10 shows a side elevation view of the respiratory assistance apparatus of FIG. 7;

FIGS. 33A and 33B1-33B3 show a metal shaft and magnet rotor assembly forming part of a motor;

FIGS. 33C1-33C4 show the metal shaft of the assembly in FIGS. 33A, 33B;

FIGS. 33D1-33D4 show a plastic shaft and magnet rotor assembly forming part of another embodiment of the motor;

FIGS. 33E and 33F1-33F3 show an injection moulding tool for manufacturing the plastic shaft and rotor assembly of FIGS. 33D1-33D4;

DETAILED DESCRIPTION OF PREFERRED EMBODIMENTS

Overview

Figure 1:
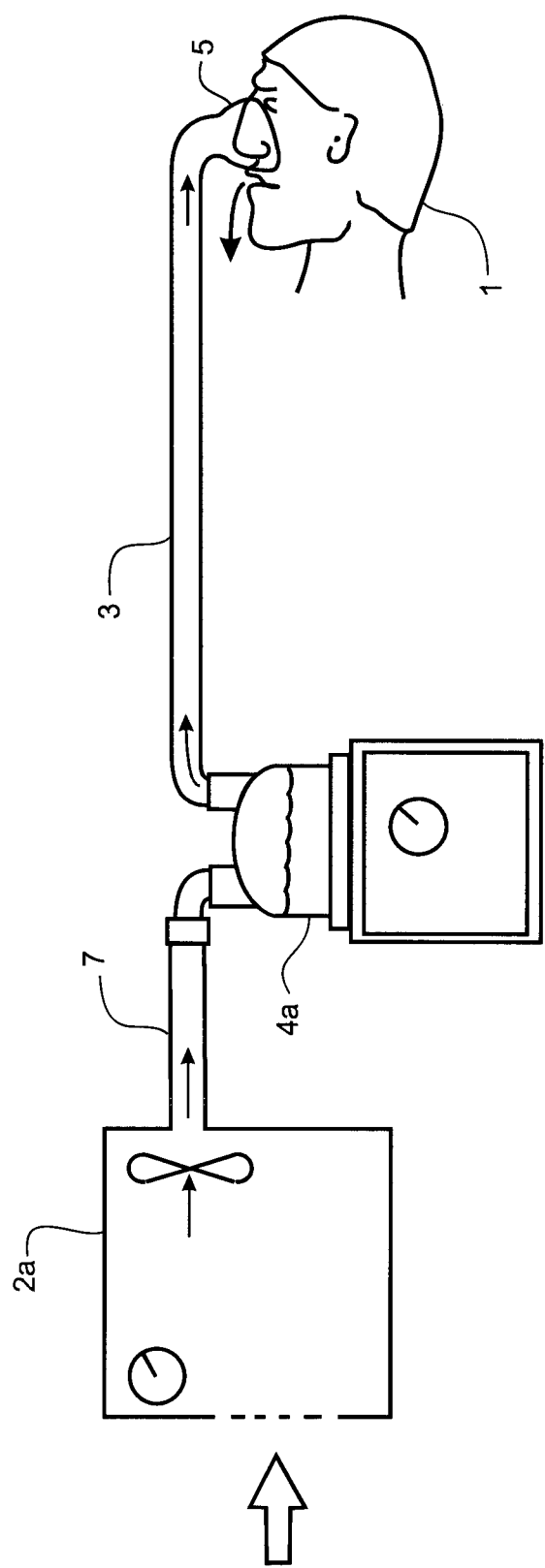
FIG. 1 shows a schematic view of a known form of respiratory assistance apparatus having a modular configuration blower unit connected to a humidifier unit.

The invention relates to a respiratory assistance apparatus (respiratory device) that is capable of supplying a flow or stream of respiratory gases to a user or patient for respiratory therapies. An embodiment of the respiratory device that is configured as a CPAP respiratory device will be described by way of example, although it will be appreciated that the respiratory device may be adapted or configured for other PAP therapies, including but not limited to Bi-PAP therapy, or any other suitable respiratory therapy that employs the delivery of a flow of gases to a user.

Wearable

Referring to FIGS. 7-12, in this embodiment the respiratory device 20 is portable and fully wearable. In particular, the respiratory device 20 is in the form of a head-mounted CPAP respiratory device. The respiratory device 20 is operable to deliver or supply a flow of respiratory gases (for example atmospheric air) at a controllable continuous pressure as is known to those skilled in the art of CPAP devices and therapies. The respiratory device can be configured to deliver gases at any desired flow rate and/or pressures required by the patient, whether customized to a single or multiple discrete flow rates and/or pressures or whether configured to operate at a range of flow rates and/or pressures. By way of example only, the respiratory device may be operable to deliver gases at a flow rate or rates in the range of 0-120 liters per minute, and can create a pressure or pressures in the range of 0-25 cmH2O, or may be customized to operate within sub-ranges of these ranges depending on patient requirements. The respiratory device 20 is portable in that the main components are all provided in a unit or assembly that is head-mountable or otherwise wearable. As will be explained in further detail later, the respiratory device's power supply may also be head-mounted or alternatively hardwired to the main unit and carried or otherwise worn by the user, e.g. in a pocket or belt-mounted for example. The respiratory device 20 comprises a base or main body 22 to which a blower unit 24 and patient interface or mask 26 are integrated, fixed or releasably mounted. The respiratory device 20 has a user-facing (or rear) side indicated by arrow A in FIG. 10 and an outward-facing (or front) side indicated by arrow B.

The blower unit 24 comprises a rotatable impeller that is configured to draw or suck in surrounding atmospheric gases or air through a blower gases inlet 28 and then pressurise those gases into a supply or stream of pressurised gases. As will be appreciated by those skilled in CPAP devices and therapy, the blower unit 24 comprises a controllable variable speed fan unit that is controllable by one or more control signals to generate the desired level of flow and/or pressure of gases at the mask 26.

The blower unit 24 is fluidly connected or in fluid communication via an airway or gases passage with the mask 26 such that pressurised gases generated by the blower unit 24 can flow into the internal cavity 30 (see FIG. 9) of the mask 26 for breathing or respiration by the user via their nose and/or mouth, depending on the type of mask employed. In this embodiment, a nasal mask 26 is provided that is configured to sealingly engage with the user's face around their nose, but alternatively other patient interfaces or masks could be used, including but not limited to full face masks covering the user's nose and mouth, oral masks for the user's mouth, nasal cannula or prongs, or any other suitable mask or patient interface for respiratory gases.

Headgear (not shown in FIGS. 7-12) is provided on the respiratory device 20 for securing the device to the head of a user. Various headgear assembly configurations can be employed to secure the respiratory device to the user's head and some examples of headgear configurations will be described by way of example later. Some example headgear configurations comprise an upper headstrap connected or coupled to an upper part of the respiratory device in the vicinity of the blower unit 24 and which extends around an upper part of the user's head above their ears and a lower headstrap that is coupled to or connected to a lower part of the respiratory device in the vicinity of the mask 26 and which extends around a lower part of the user's head, typically at or below the ear level.

Controller

The respiratory device 20 has an onboard electronic controller (such as a microcontroller, microprocessor or similar) or control system that is mounted to or within the blower unit 24, main body 22 or another part of the respiratory device. As well as other functionality, the electronic controller is primarily configured to control the pressure of respiratory gases delivered to the user by controlling the motor speed within the blower unit 24 as will be appreciated by those skilled in the art of CPAP respiratory devices. For example, the blower unit in use is set to a user-specified pressure level and/or the pressure level can be automatically controlled. The flow rate for the preferred embodiment will vary during use, depending on the users breathing. The power to blower unit can be altered, to change the speed at which the impeller is rotating, and therefore the pressure.

The electronic controller may be controlled by an onboard user interface or control panel comprising one or more switches, buttons, dials, touch screen control panels provided on the respiratory device. Additionally or alternatively, the onboard controller may be operable or controlled remotely by an external control device (e.g. a remote control, Personal Computer, portable communication device such as smart phone running a smart phone application, or any other programmable device, portable or otherwise) that communicates with the onboard controller via a wireless communication medium, such as RF communication, Bluetooth, Wi-Fi, infrared, or any other wireless communication standard or technique.

In some embodiments, the controller may be configured to employ sensorless vector control (also known as field-oriented control) of the motor in the blower unit.

The control system may comprise one or more sensors within the respiratory device that are configured to sense various operational parameters and generate representative sensor signals for the controller. For example, in some embodiments the respiratory system may comprise a flow rate sensor and/or a pressure sensor in the air flow path. The sensed signals are processed by the controller and used to control the motor in the blower unit to deliver the desired pressure and/or flow to the user as is known to those skilled in the art of CPAP respiratory devices.

The control system may also include additional sensors such as EEG, humidity, temperature, or accelerometers, to provide additional features or benefits as required.

The sensors may be hardwired or wireless, or a combination of these. In some embodiments, the sensors may be hardwired to the onboard power supply module or alternatively powered wirelessly by a wireless power transfer system in connectivity range. In some embodiments, the sensors are hardwired to the onboard controller such that the controller receives the sensor signals and/or sensor data generated. Additionally or alternatively, the sensors may be configured to transmit their sensor signals or sensor data wirelessly to the onboard controller or directly to an external system or device in connectivity range.

Power Supply

The respiratory device 20 is preferably powered by an onboard power supply package or module that is head-mounted. The power supply module may be in the form of an energy storage device or devices such as, but not limited to, a battery package comprising one or more batteries, which are typically but not necessarily rechargeable, a fuel cell, capacitor, or any other suitable energy storage device. The power supply and associated power circuitry may be mounted to or within the respiratory device, such as to or within the blower unit 24 or main body 22, or may be mounted to or integrated with the headgear or any other part of the respiratory device. Additionally or alternatively, the power supply module may be non-head mounted but otherwise portable and wearable and which can be connected to the respiratory device by a power cable or other hardwiring. In such embodiments, the power supply module may be carried or worn e.g. carried in a pocket of the user's clothing or belt-mounted for example, if the user is moving. Otherwise, the power supply module may be placed down in a convenient location near the user if desired. Typically, the power supply module is a DC power supply. Additionally or alternatively, the respiratory device may also be configured for optional connection to an AC power adaptor that connects to an AC mains power supply and converts it to a DC power supply for the respiratory device. The power supplied by the AC power adaptor may also be configured to re-charge any battery power supply modules onboard the respiratory device.

If the power supply module is a rechargeable energy storage device, such as a rechargeable battery pack or comprises rechargeable batteries, it may be recharged by either a wired or a wireless charging system, including but not limited to inductive power transfer, some examples of which will be explained later with reference to FIGS. 44-50.

It will be appreciated that in some embodiments the respiratory device may be battery-less (i.e. not have an onboard power supply module) and may be powered directly be an AC power adaptor above or alternatively powered via a wireless power transfer system, as will be discussed later.

Passive Humidification

In this embodiment, the respiratory device 20 is configured to provide passive humidification and warming or heating of the respiratory gases using accumulated moisture or humidity within the mask cavity and remaining volume of the air flow passage or path within the respiratory device that is created by the user's exhaled breath. This passive humidification may also heat the respiratory gases. This passive humidification method eliminates the requirement for active humidification, which is typically carried out by a conventional humidification unit comprising a humidification chamber after the blower unit as is known in conventional CPAP therapy respiratory devices. In some embodiments, one or more heat and moisture exchangers (HMEs) may also be provided in the air flow path to further enhance the passive humidification recycling effect.

In some embodiments, mask condensation control/reduction methods may be employed. This includes, but is not limited to, permeable mask materials, drip collection systems, and heating of the mask surface.

Zero Bias Flow

In this embodiment, the respiratory device 20 does not employ a bias flow to assist in expelling exhaled gases from the user as is known in conventional CPAP therapy respiratory devices as described with reference to FIGS. 1 and 2 in which the respiratory gases are delivered to the patient along a flexible gases conduit 3 to a patient interface 5, such as a nasal mask. In this embodiment, the respiratory device has a zero bias flow configuration. The respiratory device 20 is configured with a substantially sealed interior air flow passage or path, defined between the blower inlet 28 and the outlet region of the mask 26, that is of a sufficiently small volume to control or reduce $CO_2$ rebreathing to an acceptable or desired level without requiring a bias flow to assist in flushing exhaled gases like in the conventional CPAP respiratory devices. The total interior air flow passage volume or gas path volume within the respiratory device 20 is defined generally by the total cumulative volume of the air passage or gas path through the respiratory assistance apparatus between the atmosphere and the user's mouth, ie from the gases inlet of the blower unit 24 to the gases outlet or outlet region of the patient interface or mask 26 at the user's nose and/or mouth (depending on the type of patient interface), and includes the internal volume of the blower unit 24, any air passage or connection port between the outlet of the blower unit 24 and inlet of the mask 26 in the main body 22, and the interior volume or cavity 30 of the mask 26. The air flow passage volume is configured to be within predetermined ranges so as to control $CO_2$ rebreathing to a desired level as the controlled volume enables a portion of exhaled gases to vent back through the respiratory device and exiting the respiratory device from the blower unit gases inlet 28 and out into the atmosphere. In this embodiment, the total interior air flow passage volume is preferably less than 200 mL.

Figure 2:
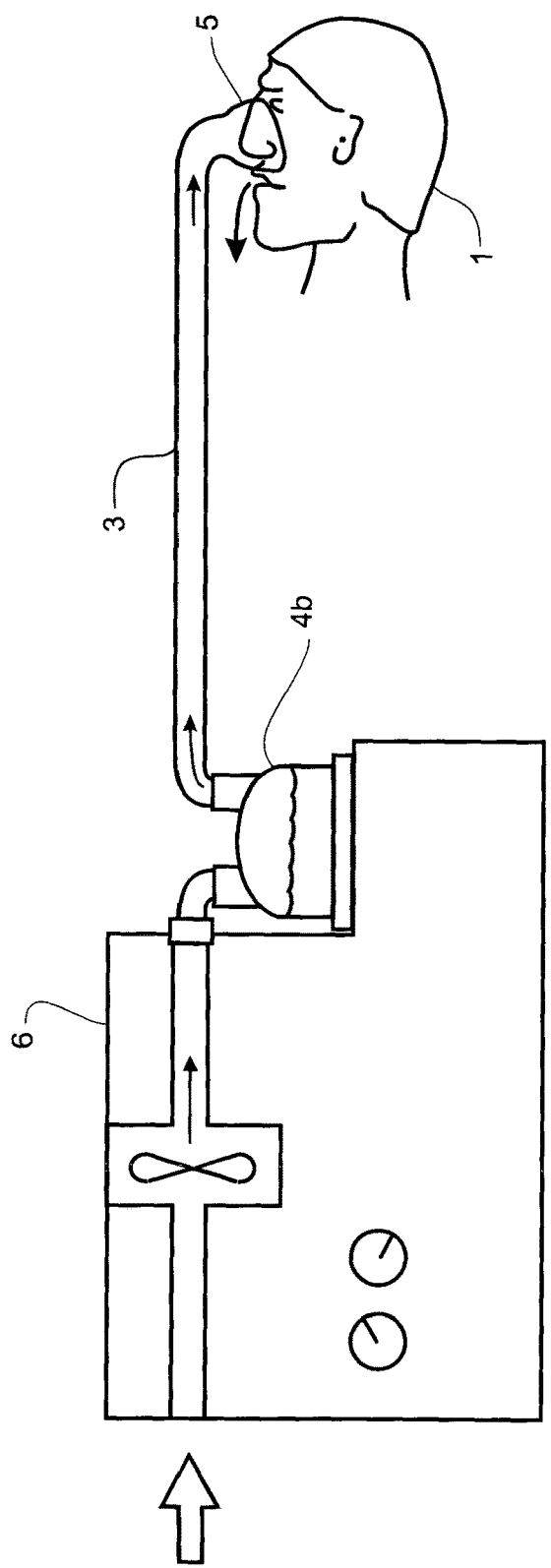
FIG. 2 shows a schematic view of another known form of respiratory assistance apparatus in which the blower unit and humidifier unit are integrated into a single main housing.
Figure 3:
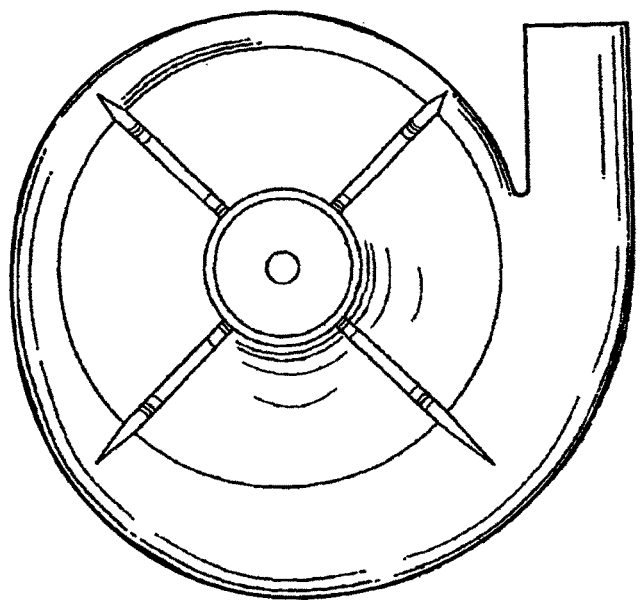
FIG. 3 shows a plan view of an example of a known blower unit.

In other embodiments, the respiratory device may be configured to optionally provide a 'reduced' or small amount of bias flow, typically at a reduced level relative to that provided in conventional CPAP therapy respiratory devices of FIGS. 1 and 2, via one or more gases washout vents, typically in the patient interface or mask or elsewhere in the air flow path. The level of bias flow may be controllable in some embodiments.

Heating

In some embodiments, additional heating of the respiratory gases may be provided in the blower unit 24 where heat dissipated from the motor and control circuitry acts to heat the incoming respiratory gases above the ambient temperature by forced convection heat transfer.

Base Station

In this embodiment, the respiratory device is also optionally provided with a separate base station configured to supply power to the respiratory device for operation and/or charging of any onboard energy storage devices, such as battery packs or similar. The base station may additionally be configured to provide data communication for compliance data transfer and/or may be configured as a docking station or mounting stand upon which the respiratory device may be docked or mounted or otherwise stored when not in use. The base station may be a unit or assembly that is configured to either rest on a flat surface, such as a table, or alternatively may be wall-mounted or fixed to any other structure in a convenient location. The base station may be provided with or control an integrated or separate power module or system that is configured to connect to the respiratory device and power it during operation and/or recharge any onboard power supply, either when it is docked or otherwise in connectivity range. The power system may be via a hardwired cable connection to the respiratory device or a wireless energy transfer system (such as but not limited to electromagnetic induction power transfer, electromagnetic radiation power transfer, or the like). The base station may additionally or alternatively provide other optional features and functionality such as communication modules for compliance data transfer, memory stick interface, calibration, drying, cleaning, clock radio, music player. By way of example only, various base station embodiments are described later with reference to FIGS. 44-50.

Model Variations

In some embodiments, some or all of the elements or components of the respiratory assistance apparatus may be disposable or replaceable, including but not limited to the mask or mask assembly, blower unit, and main body, themselves or components thereof.

In some embodiments, either or both of the blower unit and patient interface may be modular components that are releasably or removably mounted or attached to the main body such that different patient interfaces or blower units of different type, specification, size or any other characteristic may be connected to the main body to vary or customize the operation, capability, specification, characteristics, and/or functionality of the respiratory device to suit a particular application or end user requirements.

In some embodiments, the respiratory assistance apparatus may be provided or configured as a snoring treatment device by operating in a limited pressure range, for example 1-4 cmH2O. In such embodiments, the size of the respiratory assistance apparatus would be smaller than a device configured for PAP therapy.

In some embodiments, the respiratory assistance apparatus may be configured to operate in a diagnostic mode, for use either in the home or a sleep clinic. In such embodiments, the respiratory assistance apparatus may have one or more additional sensors (EEG, accelerometer, SpO2 etc).

In some embodiments, the respiratory assistance apparatus may be switchable to a "zero pressure" or "low pressure" mode, on detection of the patient being awake, or by patient manual intervention, e.g. by pressing a button on the device, or by detection of head or body movements that indicate an awake state.

In some embodiments, multiple different models of the respiratory assistance apparatus may be provided, each configured to operate at a specific limited pressure range, to minimise weight and size of the apparatus for each pressure range, and each having a blower unit and power supply that is optimised for the model's target pressure range. For example, in one embodiment three separate models may be provided, covering pressure ranges of 4-10, 8-14, and 12-20 cmH2O respectively.

Main Body and Mask Assembly

Figure 14:
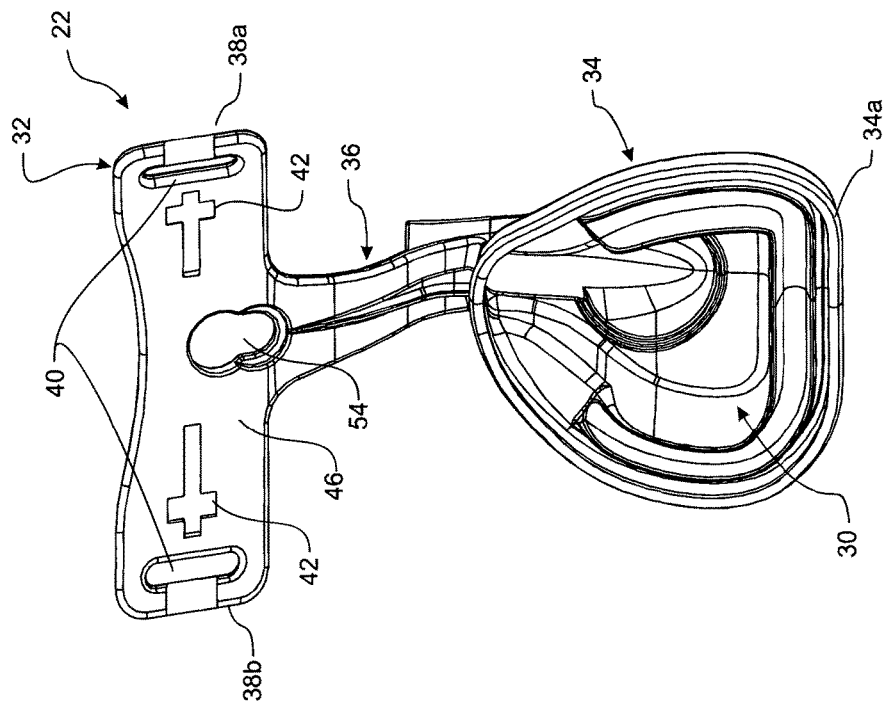
FIG. 14 shows a rear perspective view of the frame of the respiratory assistance apparatus of FIG. 7.
Figure 16:
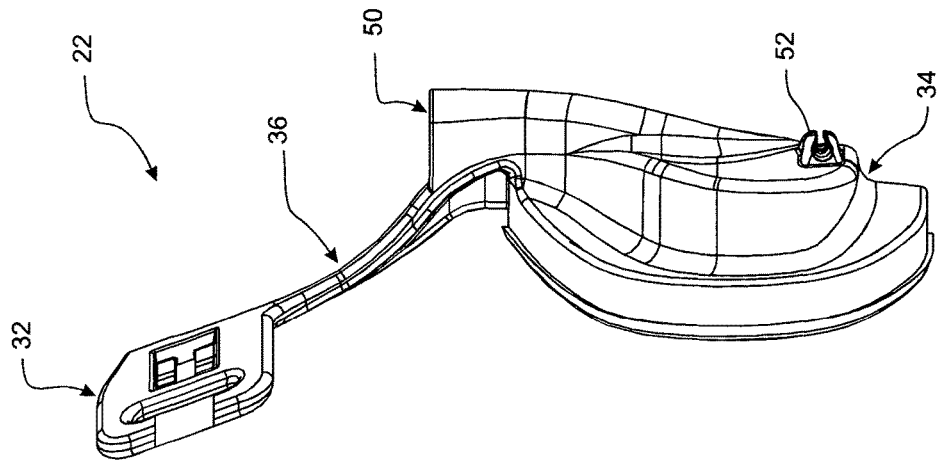
FIGS. 15 and 16 show front perspective and side elevation views respectively of the frame of the respiratory assistance apparatus of FIG. 7.
Figure 15:
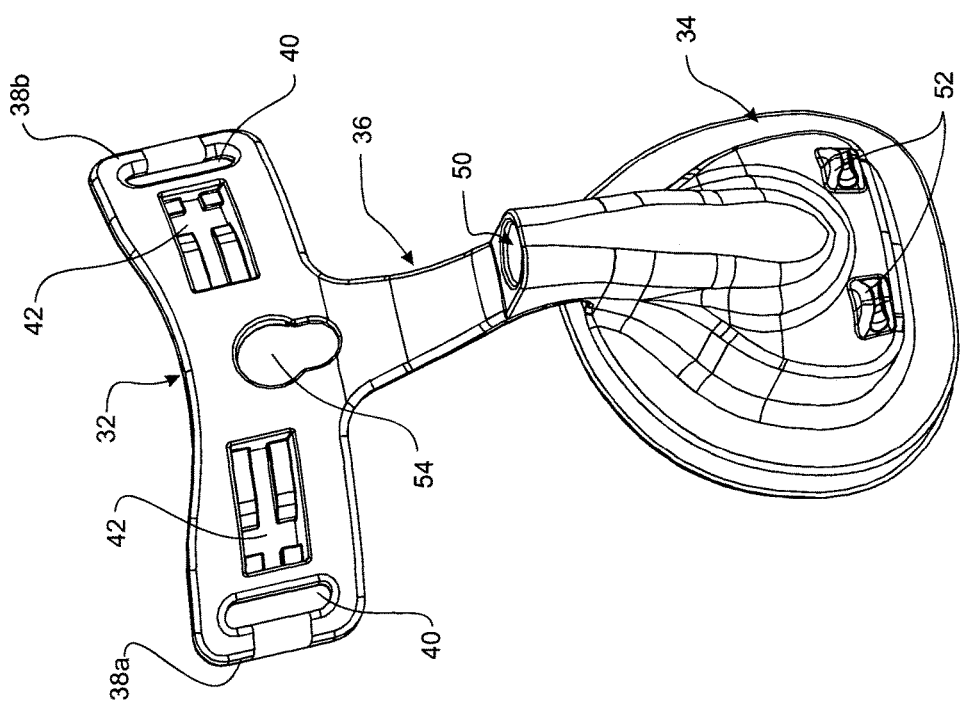

Referring to FIGS. 7-16, the main body 22 and mask 26 of the respiratory device 20 will be described in further detail. FIGS. 14-16 show the main body 22 in isolation. In this embodiment, the upper or top part or portion of the main body 22 comprises a forehead support member 32 that is configured to extend generally horizontally or laterally relative to the remainder of the main body. The forehead support 32 is configured to be located in the vicinity of the user's forehead when worn by a user. The lower or bottom part or portion of the main body 22 comprises a mask body 34 which forms part of the mask 26 or mask assembly of the respiratory device 20. The forehead support 32 and mask body 34 are connected together by a centrally and vertically extending vertical support member or connecting member 36. In this embodiment, the forehead support 32, vertical support 36, and mask body 34 are preferably formed from a rigid plastics material such as, but not limited to, polycarbonate, nylon, acetyl or other similar rigid plastic. The components 32, 34, 36 are preferably integrally formed as a single piece although it will be appreciated that the components may be formed separately and connected, fixed or otherwise releasably coupled together to form the main body 22 in alternative embodiments. The horizontal forehead support member 32 and vertical support member 36 together form a T-shape, and can be collectively referred to as a "T-piece".

In this embodiment, the forehead support 32 is substantially elongate in the horizontal direction and extends between a first end 38a and second end 38b. At or toward each end is provided a connection aperture 40 to which respective ends of a headstrap may be releasably or fixedly connected or coupled. The forehead support 32 is also provided with one or more mounting apertures 42 to which one or more pads or cushions 44 may be releasably or fixedly mounted on the user-facing side of the main body 22. In this embodiment, a pair of mounting apertures 42 each located toward a respective side of the forehead support 32 relative to the centre are provided for receiving and retaining respective cushion members 44 (see FIG. 13). In this embodiment, the mounting apertures 42 are configured to releasably receive and retain complementary mounting formations 44a provided on the rear-side of the cushion members 44. In use, the forehead support 32 locates against the user's forehead and provides stability to the mask 26 when fitted.

In this embodiment, the mask body 34 of the main body 22 forms an internal cavity 30 (see FIG. 14) into which respiratory gases are supplied from the connected blower unit 24, which is in fluid communication with the mask body 34 via an air passage or passages of the main body 22. Referring to FIGS. 15 and 16, the mask body 34 is provided with a gases inlet 50 at or toward the top of the front side of the mask body and which in this embodiment is centrally located or aligned with vertical support 36 of the main body 22. A gases flow path or passageway extends from the mask body inlet 50 and terminates or opens into the internal cavity 30 of the mask body 34.

Figure 13:
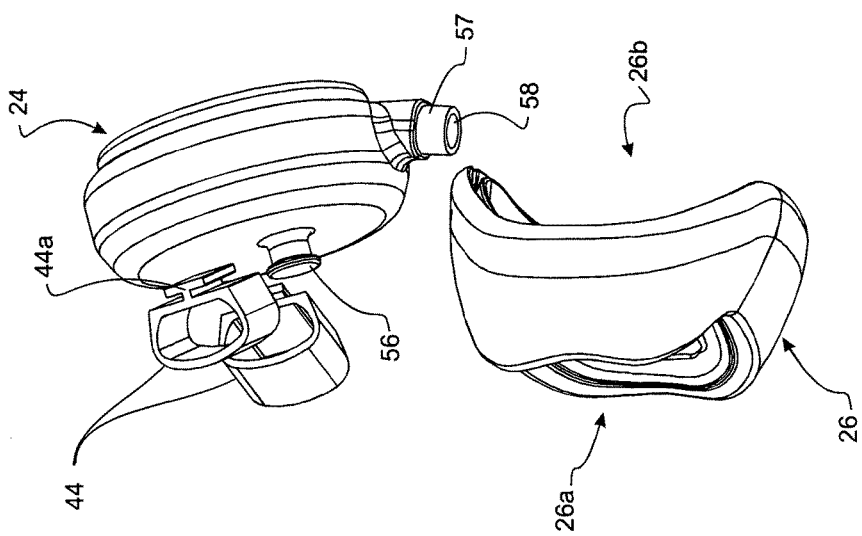
FIG. 13 shows a lower perspective view of the rear of the respiratory assistance apparatus of FIG. 7 but with the frame omitted from view, and in particular showing mask seal, blower unit, and forehead bumper components.

In this embodiment, a mask 26 or mask seal assembly is configured to be releasably mounted to the mask body 34. Referring to FIG. 13, the mask 26 in this embodiment is a nasal mask and is configured to sealingly engage with the user's face around their nose and has a front user-engaging side 26a and a rear side 26b for engaging with the mask body 34. The mask seal assembly 26 may comprise a flexible seal or cushion on the front side 26a that is shaped to substantially fit or conform to the contours of the user's face for sealing engagement and a plastic clip may be provided on the rear side 26b for releasably mounting or engaging with a complementary receiving and retaining formation provided on the mask body 34. For example, the plastic or rigid clip of the mask seal assembly 26 may be a formation that extends around the peripheral edge of the mask seal assembly 26 on its rear side 26b and which engages or releasably couples to a complementary shaped recess or formation extending about the peripheral edge 34a (see FIG. 14) of the mask body 34. The flexible seal on the front side 26a of the mask seal assembly 26 may for example be formed from a soft plastics material, such as silicone. The formation and configuration of a mask assembly formed by the mask body 34 and mask seal assembly 26 will be appreciated by those skilled in the art of patient interfaces and by way of example may be of the type described in US 2010/0006101, the contents of which is incorporated by reference. While the mask 26 is preferably releasably mounted to the mask body 34 such that it can be removed, replaced or cleaned if required, in alternative embodiments it will be appreciated that the mask may be integrally formed with of fixed to the mask body 34.

In this embodiment, the front side of the mask body 34 is provided with one or more clips 52 (see FIGS. 15 and 16) or retaining formations that are configured to slidably or receive and retain a part of the headgear assembly. For example, the headgear assembly may have a lower strap that extends around the user's head below or at ear level and which is connected to the lower part of the respiratory device by the clips 52. In one embodiment, the lower head strap may comprise an elongate glider member that may slide or glide within the one or more clips 52 such that the mask assembly may move laterally with respect to the headgear, as will be explained in further detail later.

In this embodiment, the blower unit 24 is mounted to the main body 22 such that it is located in the user's forehead region when in use. For example, the blower unit 24 is provided on or mounted to an upper part or portion of the main body, such as on or to the T-piece. In this embodiment, the blower unit 24 is mounted to the forehead support 32 or in the forehead support region of the T-piece, and is typically centrally located relative to the sides of the main body.

In this embodiment, the blower unit 24 is releasably mounted to the main body 22. The forehead support member 32 is provided with a central mounting aperture 54 (see FIG. 15) which is configured to receive and retain a complementary mounting protrusion or formation 56 that is provided on the rear side of the blower unit 24 (see FIG. 13). In this embodiment, the mounting aperture 54 has a keyhole-type shape formed by an upper circular aperture that extends or overlaps into a lower smaller aperture. In use, the retaining formation 56 of the blower unit is in the form of a cylindrical protrusion that terminates with a circular stop member of larger diameter such that the formation 56 may be inserted through the large aperture of the keyhole aperture 54 and then slid down into secure retaining engagement with smaller aperture of the keyhole mounting aperture 54. It will be appreciated that this is only one type of releasable mounting configuration for attaching the blower unit 24 to the main body 22 of the respiratory device 20. Various other alternative releasable mounting arrangements or configurations may alternatively be used such as, but not limited to, magnetic coupling, clips or clipping systems, hook and loop fastening configurations or the like. Further, in alternative embodiments the casing or housing of the blower unit may be integrally formed with the main body 22.

The bottom or underside of the blower unit 24 is provided with a gases outlet (see FIG. 13) through which the pressurised gases stream generated by the rotating fan or impeller of the blower unit exits the blower unit. In this embodiment, the gases outlet comprises a tubular connector 57 that terminates with an outlet aperture 58 or opening. The connector 57 is configured to sealingly engage into or with the gases inlet 50 of the mask body 34 when the blower unit is securely mounted to the main body. This allows respiratory gases to flow from the blower unit 24 through into the air flow passage of the main body 22 and then into the internal cavity 30 of the mask body 34.

Blower Unit Casing

Embodiments of the blower unit 24 of the respiratory device 20 will now be described in further detail with reference to FIGS. 17-33H. In this embodiment, the blower unit 24 comprises a substantially circular casing or housing 60 when viewed in plan view: The casing 60 has a front side or surface generally indicated by arrow C and a rear side or surface generally indicated by arrow D, and a peripheral wall 72 extends between the sides. The casing 60 defines a substantially hollow interior with one or more regions for receiving and retaining the blower componentry, such as a motor and impeller.

The front side or surface of the casing comprises one or more apertures or openings 64 that form a gases inlet. In this embodiment, the gases inlet 64 is a circular hole or aperture located in approximately the centre of the front side or surface of the casing 60 and passes from the outside of the casing to the inside. In use, the front face of the blower unit 24 faces away from the user and atmospheric air is drawn into the casing of blower unit via the gases inlet 64 where it is then pressurised by the rotating impeller to generate a pressurised gases stream at the gases outlet of the blower unit. While the predominant direction of flow of the respiratory gases is from the gases inlet 64 of the blower unit to the gases outlet 58 of the blower unit and into the mask body 22 for receiving by the user via the mask 26, a reverse flow also exists in the opposite direction during the user's respiratory cycle during expiration in which exhaled gases may flow back through the mask 26 and exit the respiratory device from the gases inlet 64 of the blower unit back into the atmosphere. Therefore, the gases inlets/outlets referred to are bi-directional in that they do not restrict flow in any particular direction. In this embodiment, the gases inlet 64 comprises a filter 66, which may be a foam material that has a dual purpose of filtering incoming air, and acting as a heat and moisture exchanger (HME). In alternative embodiments, the gases inlet need not necessarily comprise a filter. The rear side or surface of the casing which in use faces the user comprises a mounting protrusion or formation 56 (see FIG. 18) as previously discussed for mounting the blower unit to the main body 22.

The blower unit casing 60 houses a motor that is configured to rotate or drive an impeller, also mounted in the casing. In this embodiment, the blower unit comprises a lightweight/low inertia impeller. The lightweight nature of the impeller provides the low inertia. In use, the blower unit 24 may be controlled or set to deliver respiratory gases at a user-specified flow rate and/or pressure level. The flow rate during use may vary depending on the user's breathing. The power delivered to the motor of the blower unit can be varied by control signals from the controller to change the speed at which the impeller is rotating and therefore the flow rate and/or pressure of the respiratory gases at the mask 26.

Figure 22:
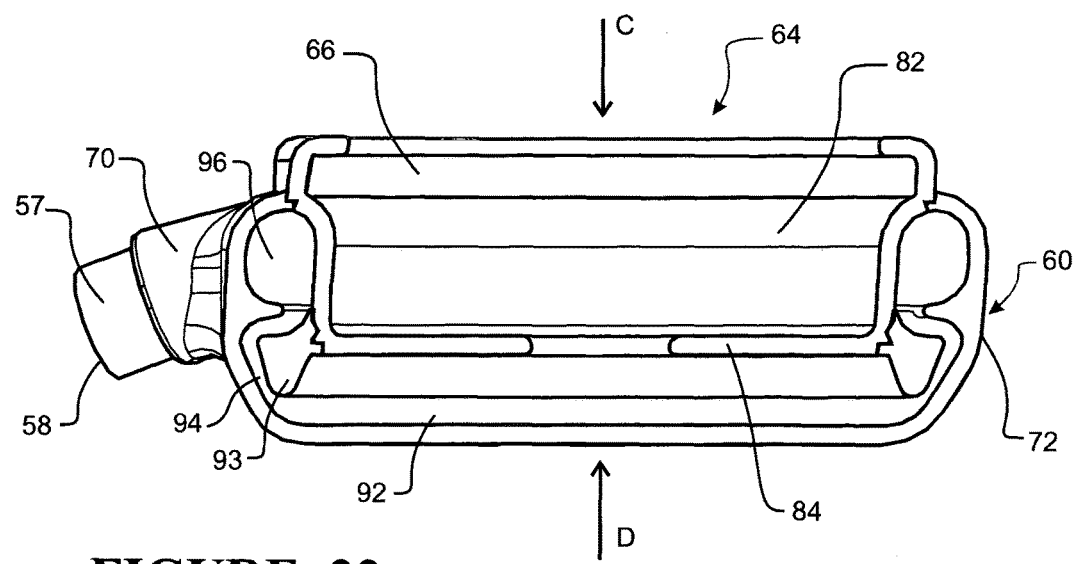
FIG. 22 shows a cross-sectional view through the casing of the blower unit of FIG. 17.

Referring to FIG. 22, the overall internal construction of the casing 60 can be seen more clearly with the motor and impeller omitted from view. As shown, the interior of the casing is divided or portioned into one or more fluidly connected regions. In this embodiment, the interior of the casing 60 is divided or separated into a first or upper interior region 82 adjacent the front side and a second or lower interior region 92 adjacent the rear side. In this embodiment, the upper 82 and lower 92 regions are formed or created by a partitioning layer or divider 84. In this embodiment, the divider 84 is a horizontally oriented circular plate or member that is parallel to the front and rear sides of the casing and which extends across the interior region between the inner surface of the peripheral wall 72 at a position intermediate or between the front and rear sides of the casing.

Figures 19, 20:
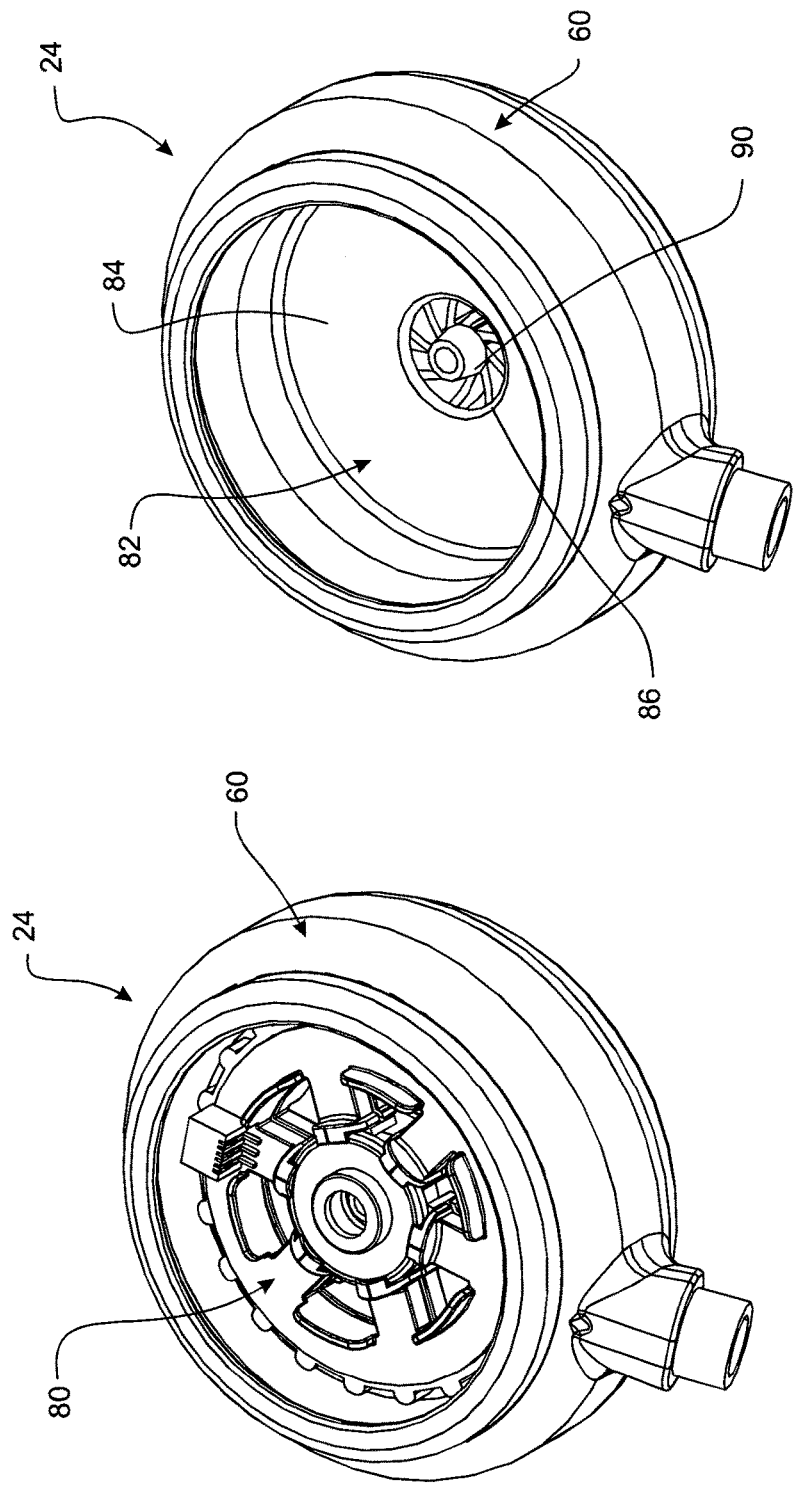
FIG. 19 shows a front perspective view of the blower unit of FIG. 17 with the gases inlet filter removed so as to expose the motor assembly.
FIG. 20 shows a front perspective view of the blower unit in FIG. 19 with the motor assembly removed from the blower unit casing.

The motor assembly 80 is mounted in the upper region 82 of the casing 60 which is defined between the front side of the casing, comprising the gases inlet 64 and filter 66, and the divider 84 as shown in FIG. 19. FIG. 20 shows the casing 60 with the motor 80 removed and exposing the receiving cavity of the upper region into which the motor is mounted. As shown, the divider 84 comprises a central aperture 86 through which a rotatable drive shaft of the motor can extend through to couple to the impeller 90 in the lower region 92 below. This aperture 86 is also large enough to allow gases to flow or be drawn through the aperture between the upper region 82 and lower region 92. For example, in operation atmospheric gases are drawn into the upper region 82 where the motor is located via the gases inlet 64 and filter 66 and then flows through the divider aperture 86 into the lower region 92 where the impeller 90 is located. It will be appreciated that one or more additional apertures may be provided in the divider 84 to increase the flow of air from the upper region 82 into the lower region 92.

In an alternative embodiment, the aperture in the divider 84 through which gases flow through between the upper region and lower region may be an opening located at or close to the outer edge of the divider. For example, the opening may be a cut-away in the partition layer 84 or some other configuration/shape of the casing such that the combination/arrangement of the partition layer 84 and the casing creates an aperture/opening between the two. The cut-away could form a circumferential aperture between the casing and partition 84, for example. The curvature/centre of radius of the circumferential aperture is preferably offset from the centre of radius of the partition layer 84 or otherwise has a curvature that differs from that of the circumference of the partition 84 resulting in an eccentric or otherwise offset circumferential aperture around the circumference of the partition. This produces an aperture with a crescent ("smile") opening that spans a leading edge to a trailing edge. However, the aperture may be of any shape with a gradual opening and closing relative to the plane of impeller rotation. The aperture allows for gradual supply of pressure and flow from the high static pressure source at the top of the blower. The angle of the aperture opening and closing is tuned to allow for reverse flow to return through the system in a stable fashion. It also contributes to the blade pass noise reduction by not having a sharp break in geometry.

Figure 21:
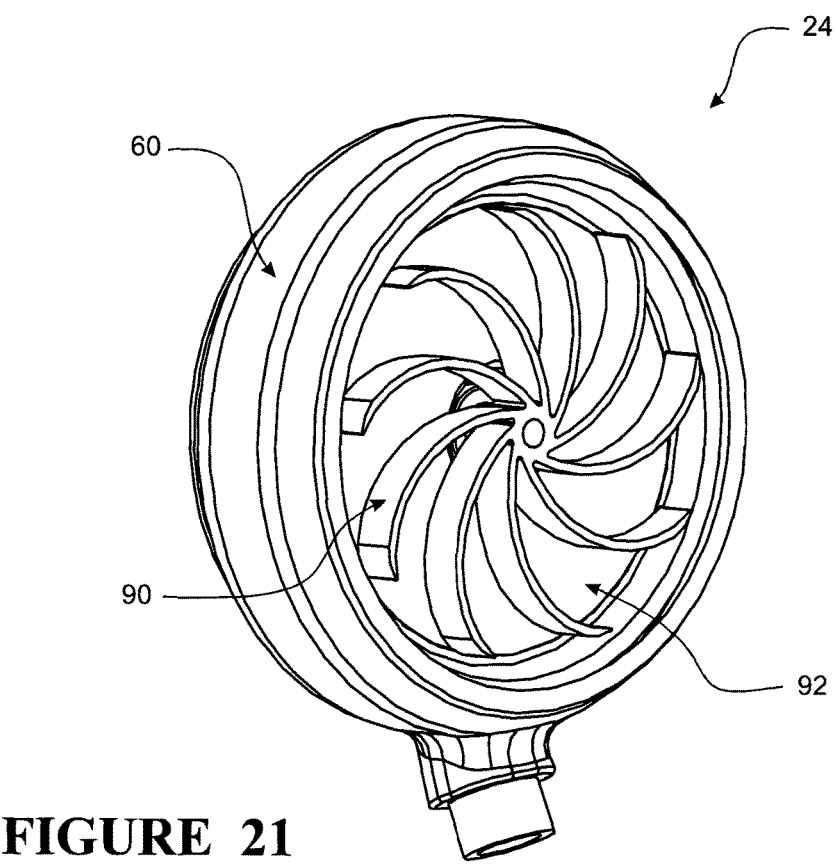
FIG. 21 shows a rear perspective view of the blower unit of FIG. 17 with a portion of the rear side of the casing cutaway to expose the impeller.

The impeller 90 is mounted in the lower region 92 of the casing 60 which is defined between the rear side of the casing and the divider 84 as shown in FIG. 21, which shows a cut-away view of the rear side of the casing to expose the impeller 90.

Figure 17:
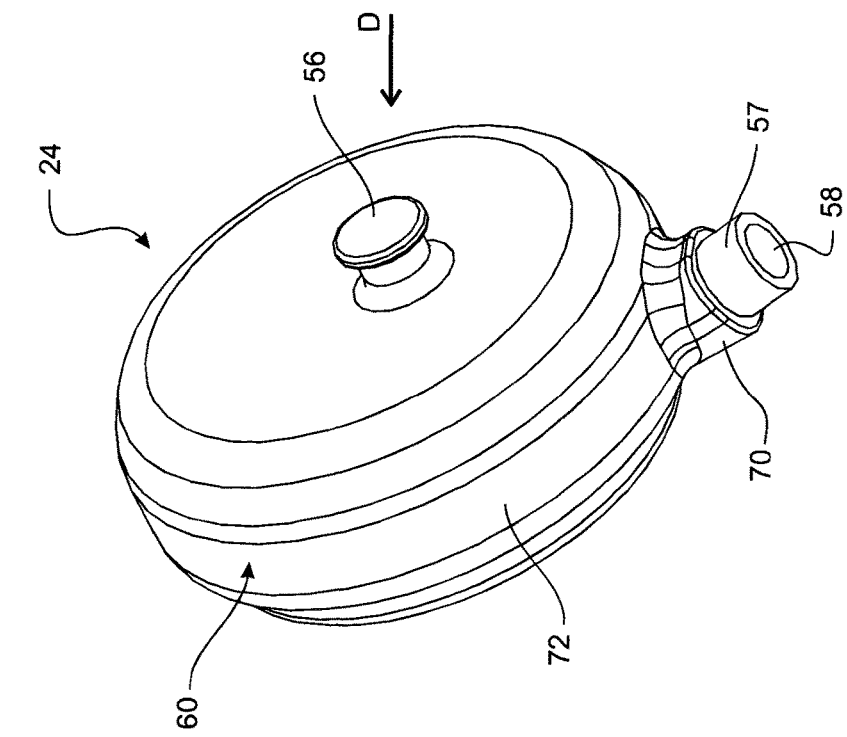
FIGS. 17 and 18 show front and rear perspective views respectively of the blower unit of the respiratory assistance apparatus of FIG. 7.
Figure 18:
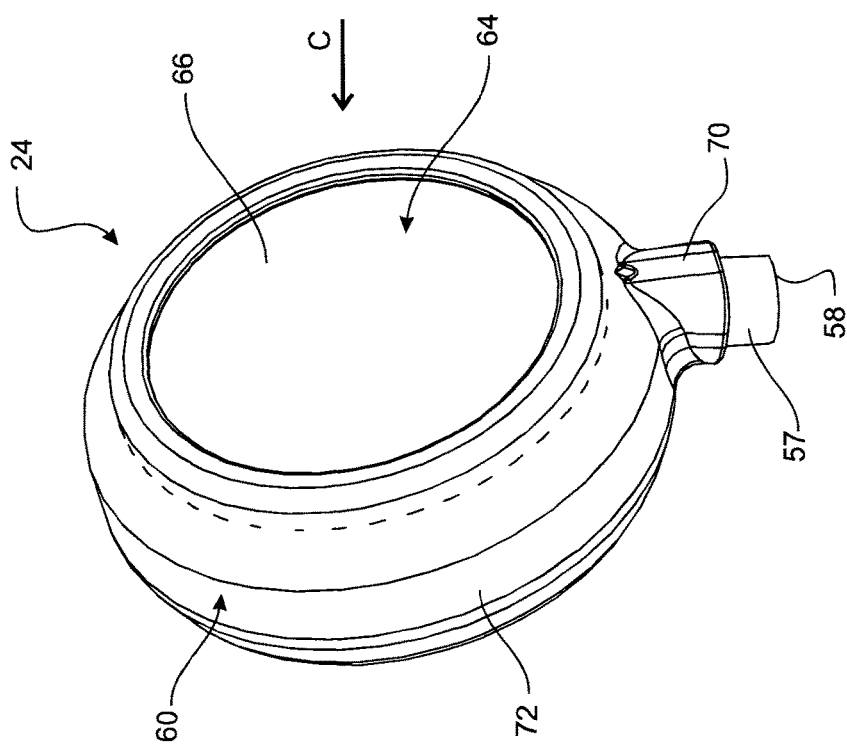

In this embodiment, the gases outlet of the blower unit 24 extends outwardly from the peripheral wall 72 of the casing. Referring to FIGS. 17, 18 and 22, the gases outlet comprises a gases outlet passage 70 that is connected to an interior region of the casing 60 and which extends outwardly from the peripheral side wall 72 of the casing at or toward the bottom of the blower unit. The gases outlet passage 70 is provided with a tubular connector 57 at its outer end, and the connector 57 terminates with an outlet aperture 58 through which a pressurised gases stream may flow. The connector 57 in this embodiment is circular in cross-section and is configured to connect or couple to the gases inlet 50 of the main body 22 so as to fluidly connect the blower unit to the main body 22 and mask 26 for the flow of gases. In this embodiment, the gases outlet passage 70 has a generally circular cross-section and extends radially outward from the centre of the casing. However, the outlet passage 70 could also be arranged to extend outwardly at any alternative suitable angle relative to the circular casing, for example aligned substantially tangentially to the side wall of the casing, or at any suitable angle between tangential and radial. It will be appreciated that the cross-sectional shape of the outlet passage 70 and connector 57 need not necessarily be circular, but could be any other desired or suitable shape. The outlet passage 70 causes the gases forced outwards by the impeller 90 to coalesce as a gases stream, and dictates the direction in which the gases stream flows from the blower unit.

Reverting to FIG. 22, the casing 60 is also provided with an interior formation 93 that forms or provides an air passage 94 or pathway from the lower region 92 to a volute 96 or transition region. The volute 96 collects the gases forced outwardly from the rotating impeller 90 before emission from the blower unit via the outlet passage 70, which is fluidly connected to the volute. In operation, gases circulating in the volute 96 are diverged into the outlet passage 70 which forms a pressurised gases stream. In this embodiment, the volute 96 is a channel or passage extending circumferentially within the casing around the outside of the upper region 82 of the casing. In this embodiment, the air passage 94 extends from the lower region up into the volute 96 and is also located circumferentially about the periphery of the interior of the casing 60.

It will be appreciated that the gases pathway from the gases inlet 64 of the casing 60 to the lower region 92 where the impeller 90 is situated may be provided in other ways and need not necessarily flow through the upper region 82 where the motor is located. For example, in an alternative embodiment the gases inlet may be provided on the rear side of the casing adjacent the impeller in the lower region 92.

Operation

During operation of the blower unit 24, rotation of the impeller 90 by the motor 80 draws gases through the gases inlet 64 and into the upper region 82 of the casing and through the motor assembly 80 to the central aperture 86 of the divider 84. The air drawn through the motor assembly 80 can also act to cool the motor. The shroudless impeller enables air to be drawn through the motor in this manner to thus providing cooling. The gases flow through the aperture 86 into the lower region 92 and through the blades of the impeller toward the peripheral side wall 72 of the casing in the lower region. The impeller blades impart strong rotational forces to the gases circulating in the lower region 92 of the blower casing to thereby create high circulating gas speeds. Gases in the lower region 92 will naturally flow through the air passage 94 into the volute 96 due to pressure differential between regions. When the gases in the lower region 92, having a high velocity and low pressure, enter the volute 96, the gas velocity drops and the pressure increases. Typically, the volute 96 has a greater volume than the lower region 92 to help facilitate this gases pressure increase.

By dividing the blower internal space into separate regions a number of advantages can be realised. In a conventional blower, high velocity gases leaving the impeller are incident to an edge, or tongue, that defines a physical boundary where gases are split from the volute to enter the outlet passage. High velocity gas flow incident at the tongue is turbulent and inefficient to blower performance. The turbulence caused by the tongue also introduces a source of noise. In contrast, dividing the casing of the blower unit into separate but connected gases regions reduces the impact caused by the tongue. The lower region 92 allows the gases to circulate at a high speed. The gases path or passage 94 provides a fluid path to the volute 96 that is free from aerodynamically turbulent edges. When circulating gases have entered the volute region 96, the enlarged volume of the volute encourages the gases to slow and increase in pressure. The reduced gases velocity reduces the impact of turbulence normally caused by the tongue to a low or negligible level. The blower unit is therefore able to operate across a wide pressure and flow range with substantially reduced noise output when compared to other blowers. A wider passage 94 increases the flow rate of the volute relative to the lower region. Therefore, the size of the passage 94 is selected according to the desired flow rate and pressure range of the blower unit.

Impeller

Figure 5:
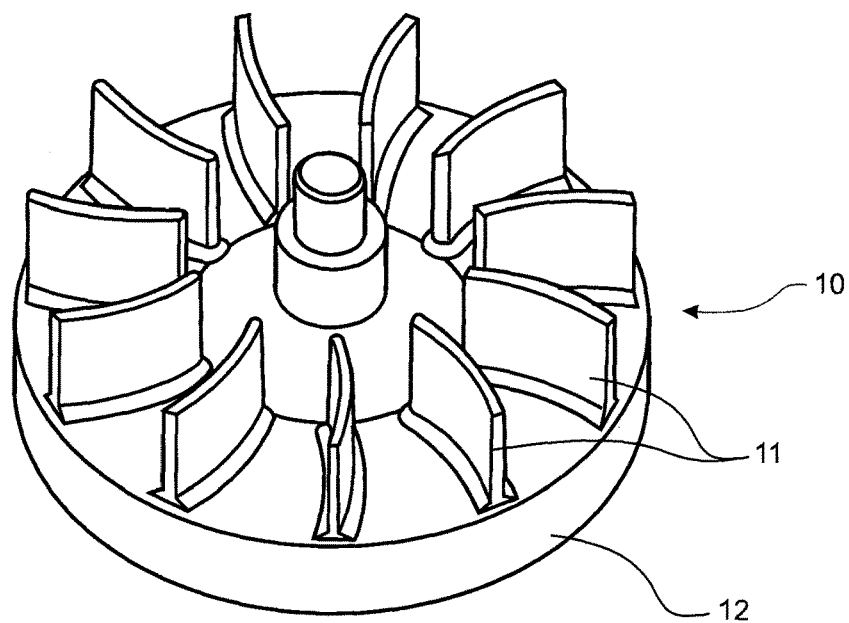
FIG. 5 shows a profile view of a known impeller.
Figure 6:
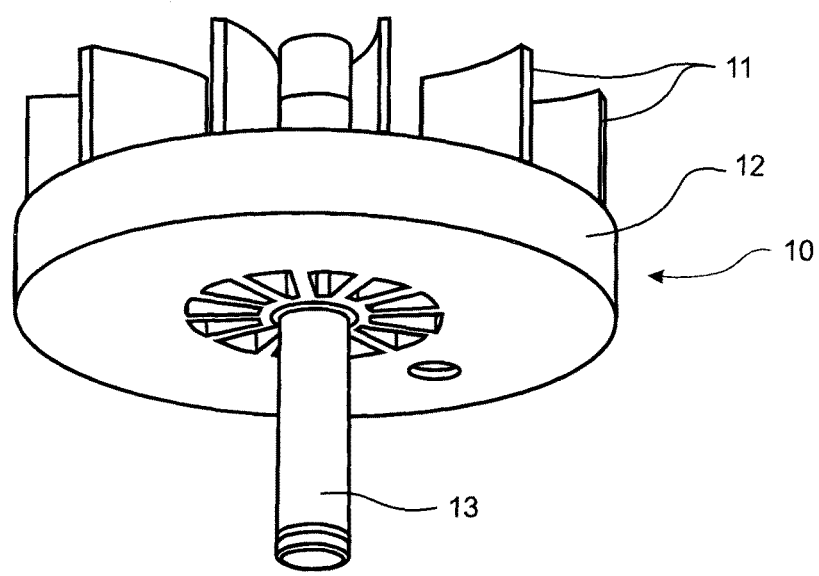
FIG. 6 shows another profile view of the impeller of FIG. 5.
Figure 7:
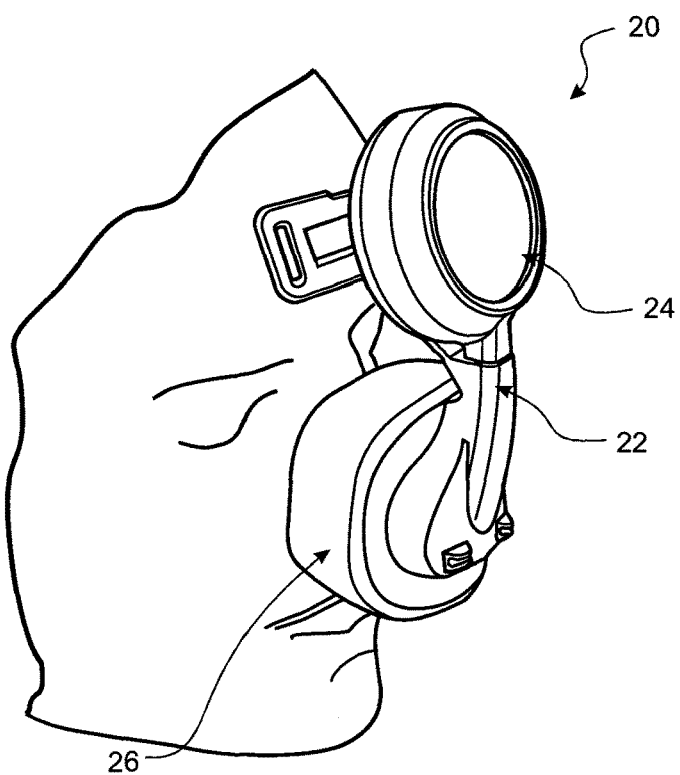
FIG. 7 shows a perspective view of a wearable respiratory assistance apparatus having a head-mounted blower unit in accordance with an embodiment of the invention and shown mounted to a user's head but with the headgear not shown.
Figure 8:
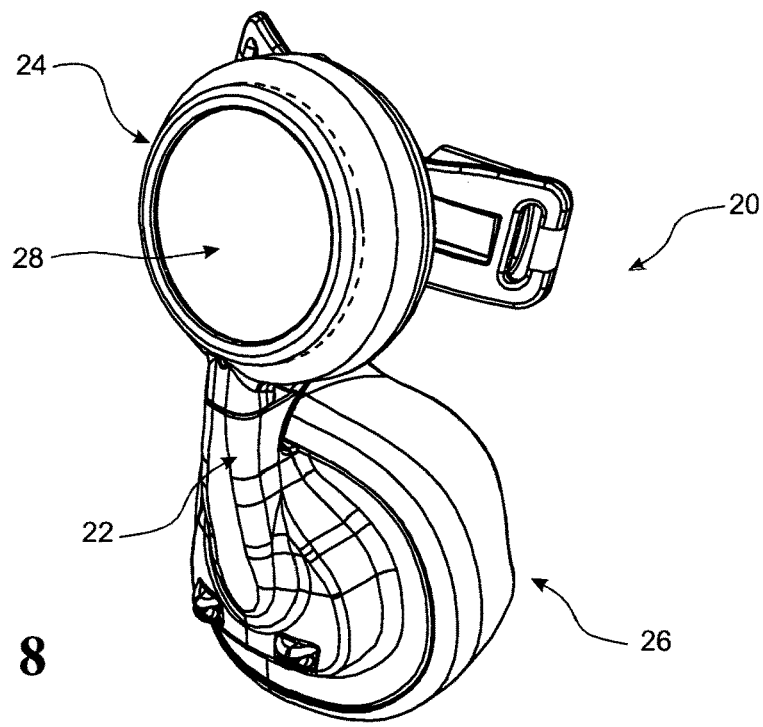
FIG. 8 shows an upper perspective view of the front of the respiratory assistance apparatus of FIG. 7 with the user omitted.
Figure 12:
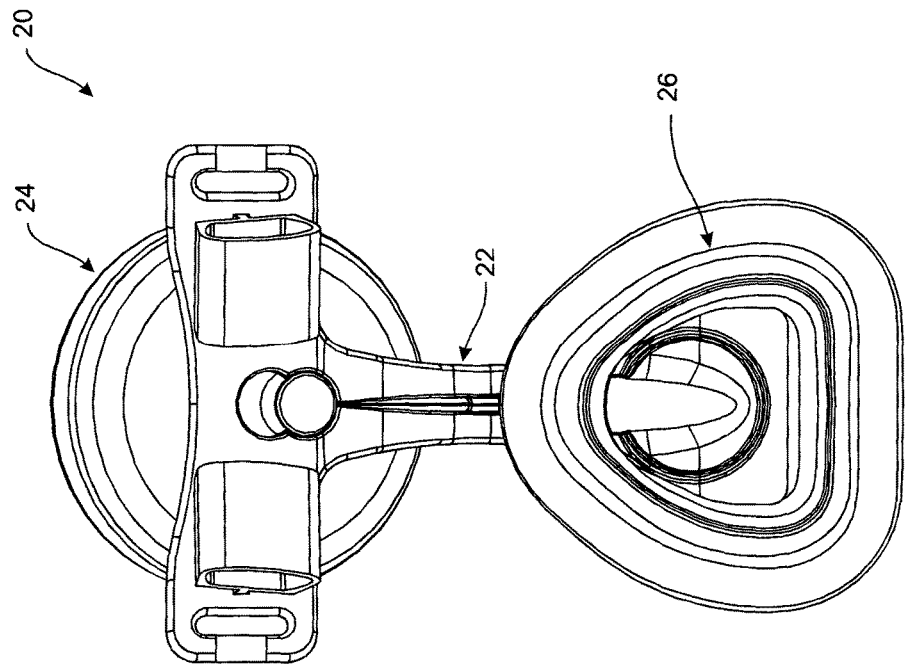
FIG. 12 shows a rear elevation view of the respiratory assistance apparatus of FIG. 7.
Figure 11:
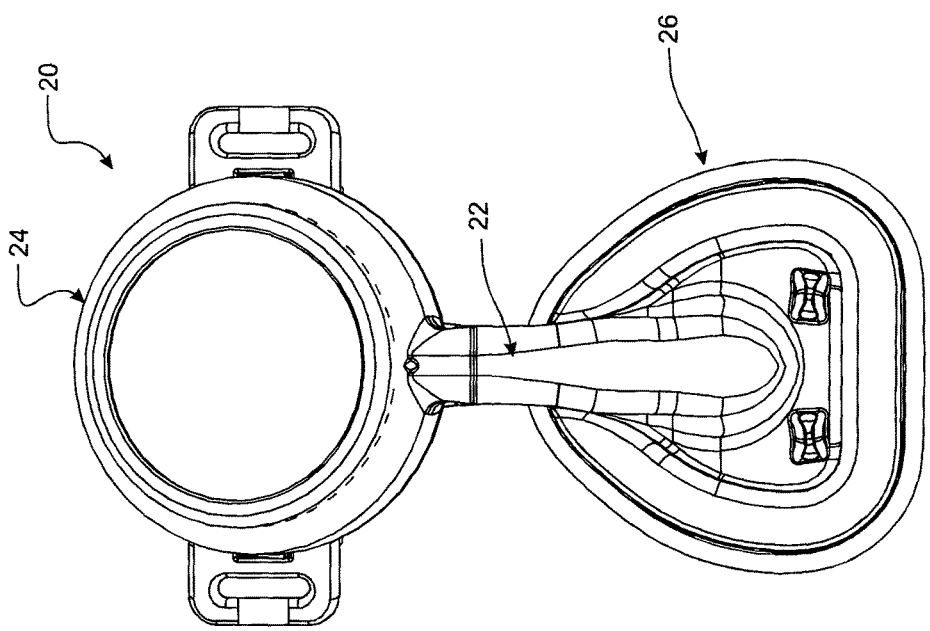
FIG. 11 shows a front elevation view of the respiratory assistance apparatus of FIG. 7.
Figure 24:
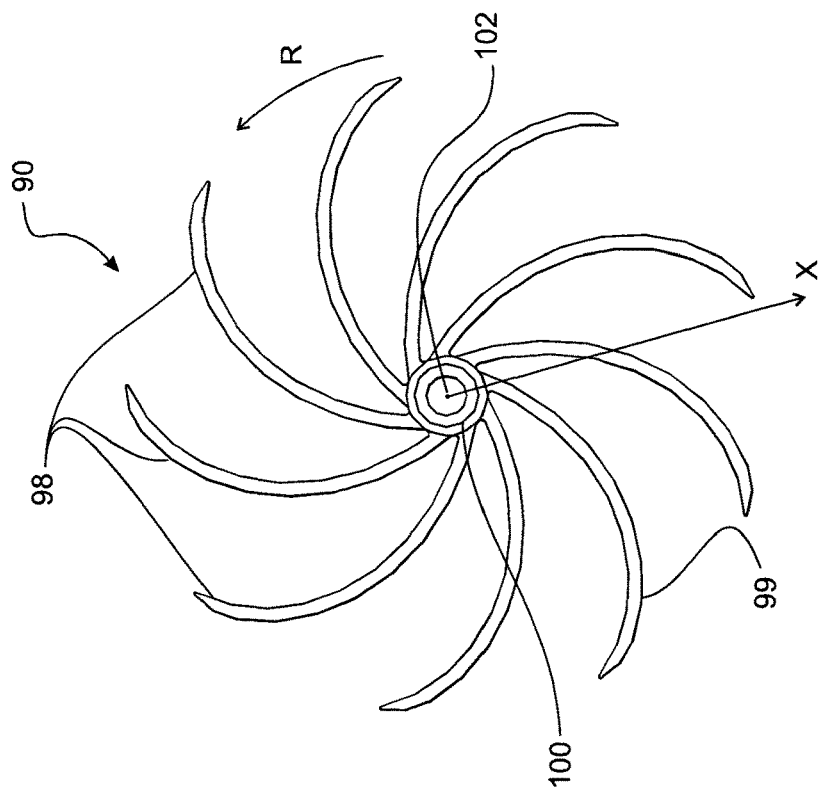
FIGS. 23 and 24 show perspective and plan views respectively of an impeller of the blower unit of FIG. 17 in accordance with an embodiment of the invention.
Figure 23:
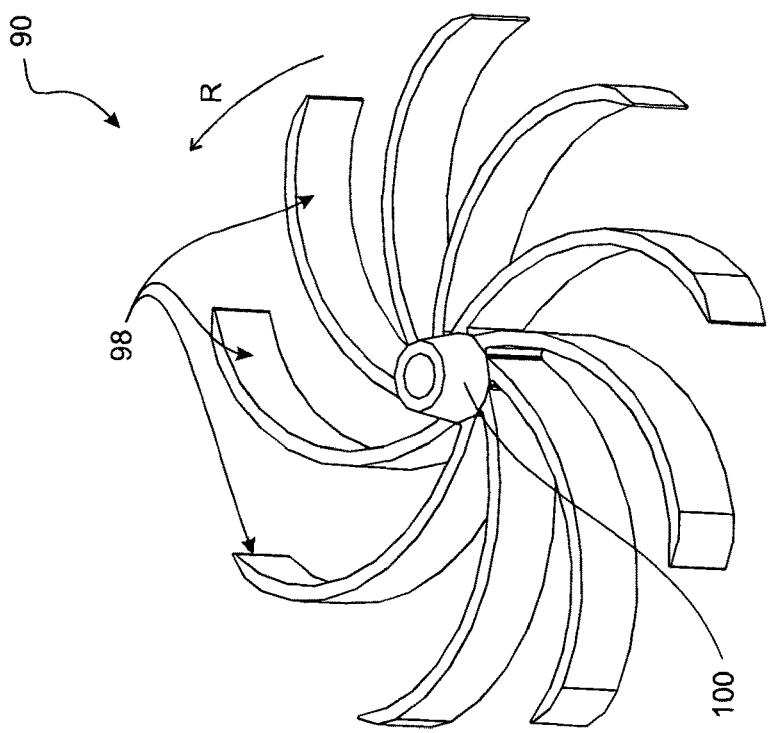

A first embodiment of the impeller 90 is shown in FIGS. 23 and 24. The impeller 90 has a plurality of blades 98 extending outward from a central hub 100. The impeller is a centrifugal impeller. The hub 100 defines the axis about which the impeller rotates. Preferably the hub 100 has an aperture 102 or recess to allow engagement with a rotatable drive shaft of the motor 80 which facilitates impeller rotation. However, other engagement mechanisms, such as over moulding of the hub with a shaft, could be used. When the impeller is rotated, air enters the impeller blades in the region proximate the hub 100, travels radially outward and exits the blades proximate the blade tips. The impeller is preferably made in one piece ("one piece construction"), as opposed to moulded in multiple parts and joined. This is possible when there is no shroud—or at most one shroud. This reduces misalignment of components that might lead to imbalance or other disadvantages. In the preferred embodiment there is no shroud (in contrast with for example the shroud 12 shown in FIGS. 5 and 6).

The blades 98 preferably provide a substantially flat surface, from the hub 100 to the blade tip, and incident the direction of rotation indicated by arrow R to thereby centrifuge gases. In this embodiment, the blades 98 are arcuate or curved from the hub 100 to the blade tips and the curve is preferably backward swept in the opposite direction of impeller rotation indicated by arrow R. The impeller is a backward facing impeller in that each blade 98 extends from the hub 100 in a direction backward of its associated radii extending from the hub, relative to the direction of the impeller rotation R. For example, blade 99 is shown extending backwardly relative to its associated radii X in FIG. 24.

Figure 25B:
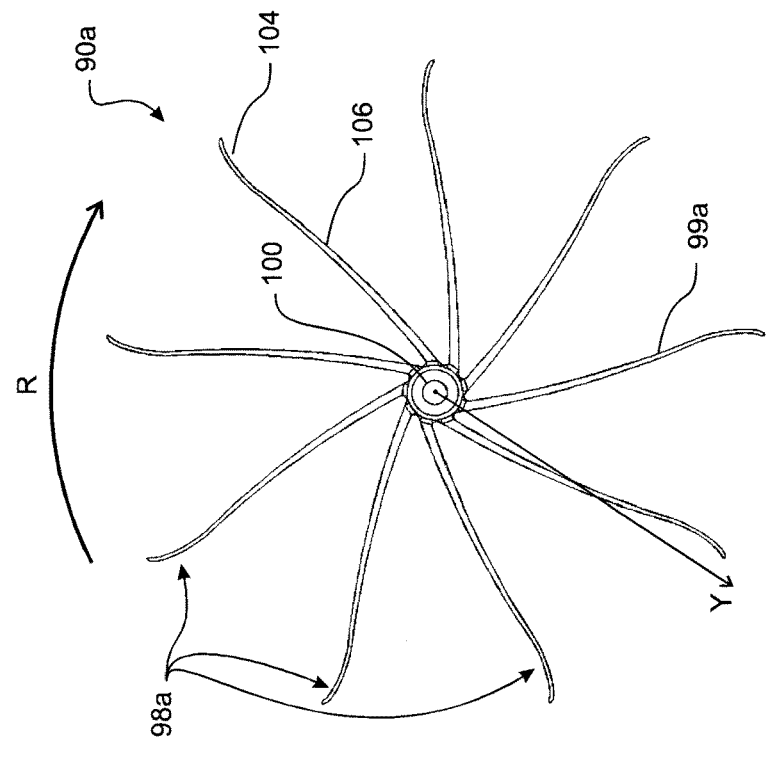
FIGS. 25A and 25B show perspective and plan views respectively of an impeller for the blower unit of FIG. 17 in accordance with another embodiment of the invention.
Figure 25A:
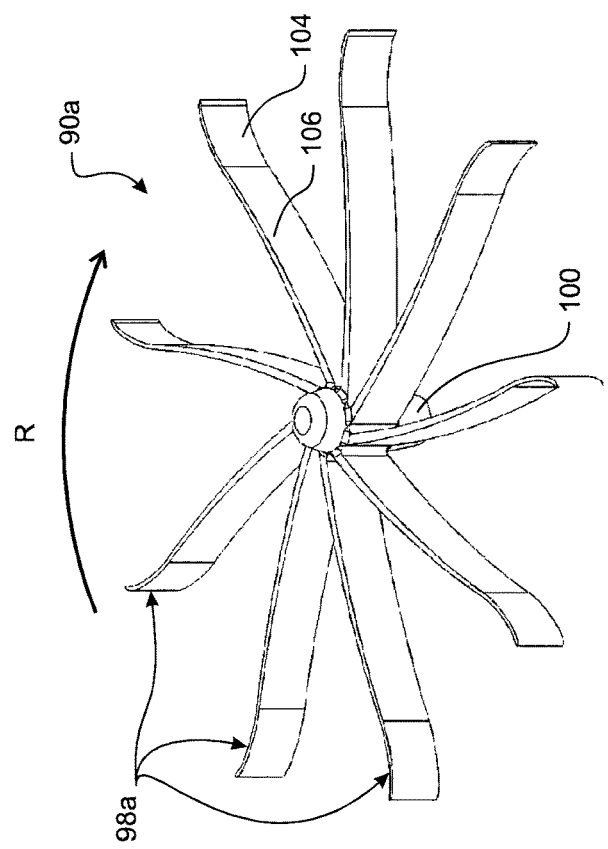

A second embodiment of the impeller 90*a* is shown in FIGS. 25A and 25B. The impeller 90*a* construction is similar to that of impeller 90, except the blade profile 98*a* is different. In this second embodiment, the blades 98*a* have a profile that comprises blade tips 104 that partially curve in the direction of the impeller rotation R. That is, the blade tips 104 are forward swept. Forward swept blade tips help to impart stronger rotational forces on the gases flowing through the impeller than straight or backswept blades. The forward swept blade tips help to produce a high pressure annulus beyond the tip of each blade. For example, the impeller generates a high pressure annulus between the blade tips and inner face of the peripheral side wall of the casing. The inner portion 106 of the impeller blades 98*a* between the hub 100 and blade tip 104 may be somewhat backswept. A backswept blade allows for some recirculation of gases on the blade surface itself. The backswept inner blade portion 106 may be beneficial to increase pressure generation and allow for stable low and reverse gases flow. In this embodiment, the impeller is a backward facing impeller in that each blade 98*a* extends from the hub 100 in a direction backward of its associated radii extending from the hub, relative to the direction of impeller rotation R. For example, blade 99*a* is shown extending backward of its associated radii Y in FIG. 25B.

It will be appreciated that the impeller of the blower unit may be implemented with any suitable blade profiles, whether forward, backward or radial blades, or any other suitable profile.

In either embodiment, the impeller 90, 90*a* is constructed to be lightweight. Preferably, this is by making the impeller shroudless, or at least partially shroudless, thereby removing weight. To achieve a lightweight impeller, as shown in FIGS. 23-25B, each of the blades of the impeller are open between the blades (that is, the upper and lower "faces" or "planes" of the impeller are open to the internal surfaces of the casing 60 of the blower unit 24) thereby defining a shroudless centrifugal impeller. By omitting a shroud on both the upper and/or lower faces of the impeller blades, the weight of the impeller can be substantially reduced. The weight of the impeller can also be reduced in other ways, in addition to or alternatively to omitting the shroud. For example, a lightweight material can be used. Also, thin blades with minimal material and large gaps between blades could be implemented to reduce weight.

Figure 26A:
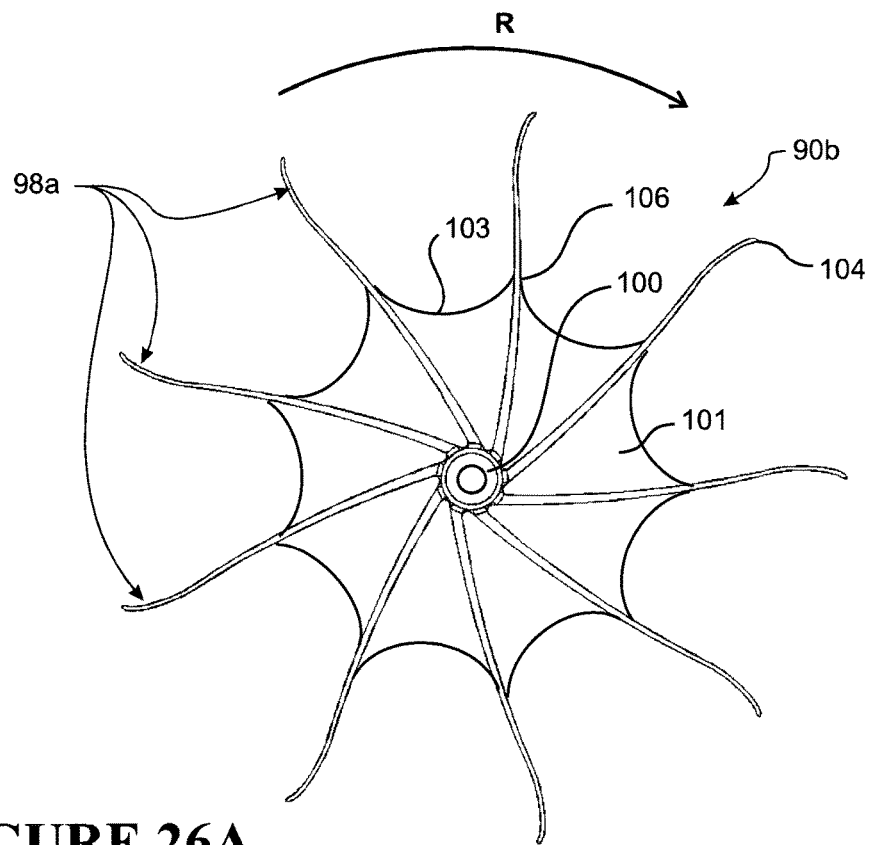
FIGS. 26A and 26B show plan and perspective views respectively of an impeller with reduced shroud material for the blower unit of FIG. 17 in accordance with another embodiment of the invention.
Figure 26B:
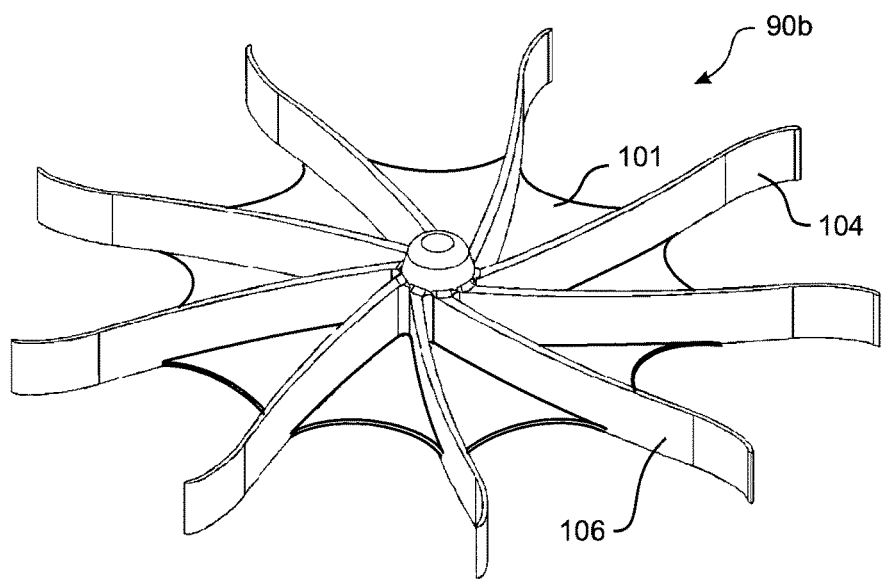
Figure 26C:
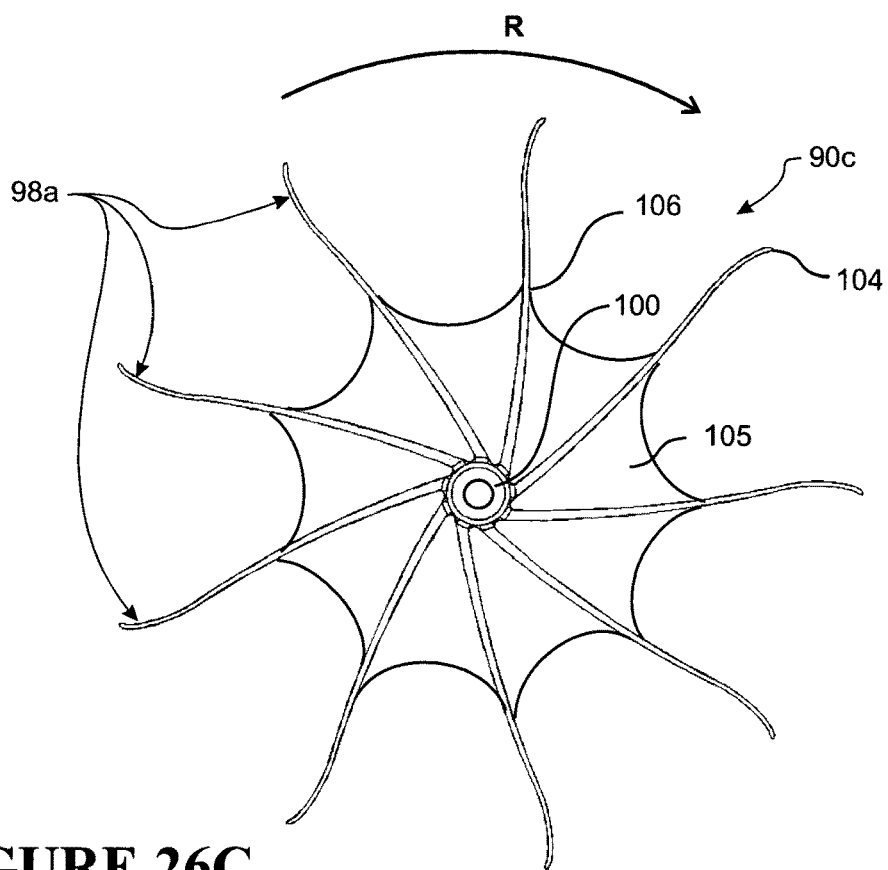
FIGS. 26C and 26D show plan and perspective views of an impeller with a web structure for the blower unit of FIG. 17 in accordance with another embodiment of the invention.
Figure 26D:
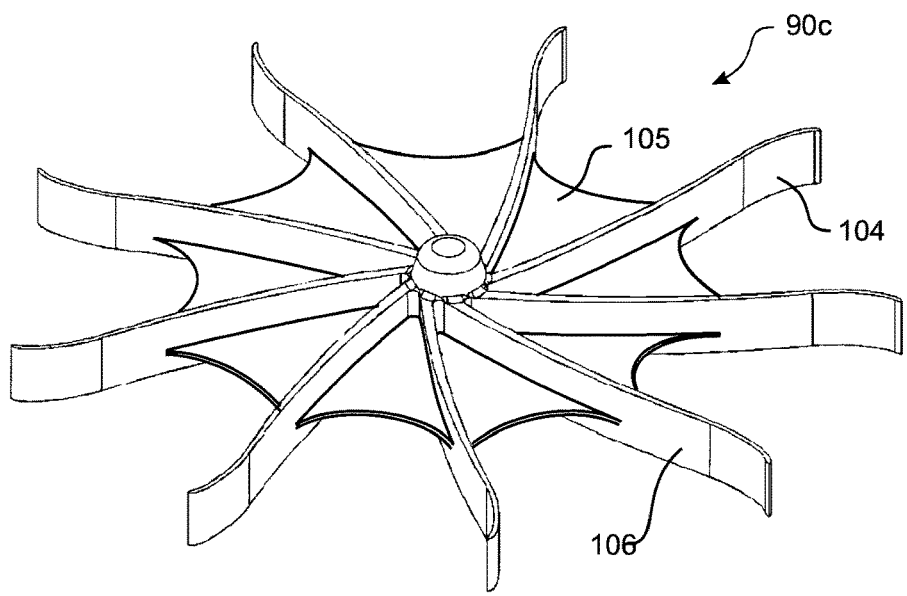

Alternatively, a shroud 101 with some of the material removed, such as shown in the third embodiment impeller 90*b* of FIGS. 26A and 26B could be used. A scalloped shaped 103 shroud is provided whereby some of the material between blades 98*a* is removed. Any suitable amount of material could be removed. A shroud channels air from the impellers. Where significant material is removed, the resulting structure may in fact no longer carry out this function of a shroud but rather just provide support for impeller blades 98*a*. In this case, the impeller 90*b* may still be considered shroudless, despite having some structure between impeller blades 98a. In yet a further, fourth embodiment impeller 90c shown in FIGS. 26C and 26D the structure between the impeller blades 98a is a webbing 105 that is disposed centrally between the upper and lower planes of the impeller. Such a structure does not function as a shroud. The reduced material structure or webbing 105 can be of any shape (not just scalloped) or extent, of which FIGS. 26A-26D show two examples.

A lightweight impeller provides benefits such as manufacturing cost, low rotational inertia and is balanced or requires little effort to rotationally balance once manufactured. An impeller with low rotational inertia can be quickly accelerated and decelerated. A lightweight, shroudless impeller is therefore suited for quickly responding to fluctuating pressure requirements, such as the normal inhalation and exhalation cycle of a patient connected to the breathing assistance device in which the impeller operates. In other embodiments, the impeller need not necessarily be lightweight.

Figure 40:
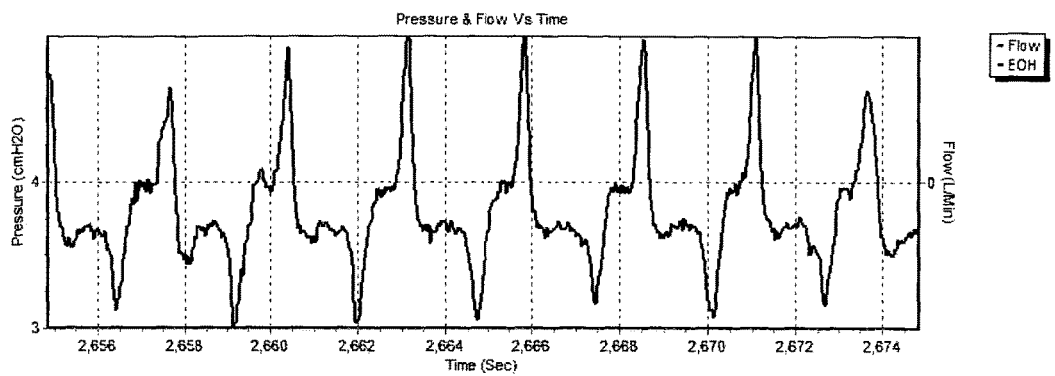
FIG. 40 shows a pressure response graph of a conventional blower unit.
Figure 41:
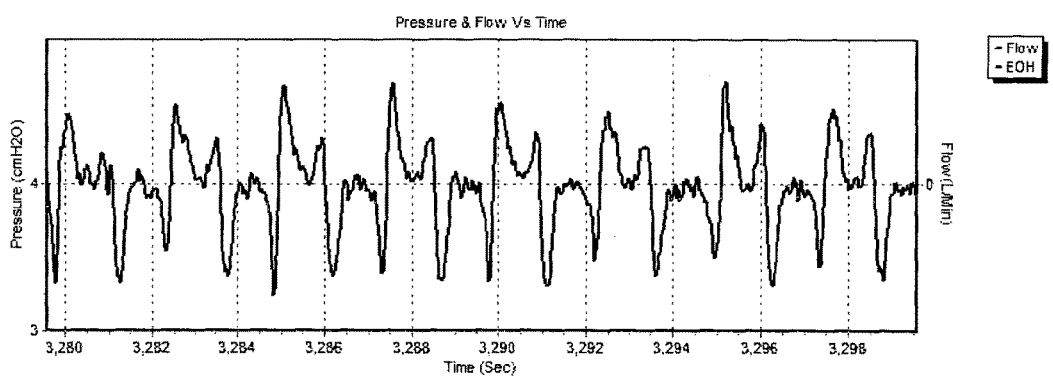
FIG. 41 shows a pressure response graph of a blower unit in accordance with an embodiment of the invention.

For example, a conventional shrouded impeller commonly used on a breathing assistance device, weighing approximately 17 grams and having inertia of 6 kg·mm2, can respond to pressure fluctuations of 10 cmH2O in approximately 2 seconds. By contrast, an impeller in accordance with either embodiment 90,90a, weighing approximately 1.7 grams and inertia of 0.5 kg·mm2, responds to pressure fluctuations of 10 cmH2O in approximately 100 ms. FIG. 40 shows a graph of pressure verses time for a conventional shrouded impeller weighing 17 grams. The impeller is operated to attempt to maintain a constant pressure of 4 cmH2O during the normal inhalation and exhalation cycle of a patient. In comparison, FIG. 41 shows a graph of pressure verses time for the preferred impeller 90, 90a. It can be seen that the decrease in mass and rotational inertia over the earlier impeller exhibits much less pressure fluctuation than a conventional impeller of FIG. 40. The reduced pressure fluctuation is less disruptive to a patient's breathing process, and therefore advantageously increases patient comfort.

As mentioned, the lightweight can be achieved by omitting a shroud. However, it is not necessary to omit the entire shroud—rather just sufficient shroud to bring the weight of the impeller to a suitable level—such as shown in FIGS. 26A-26D. Therefore, lightweight can be achieved by having as much open space (area or volume) between the blades as possible. The open space can be defined in terms of the blade volume to blade sweep volume ratio/percentage. That is, the blades sweep a volume X when rotating and the blades themselves have a combined volume Y (which is the volume of each blade combined). Alternatively, from a plan perspective, the open space can be defined in terms of the blade area to the blade sweep area. The ratios should be kept as low as possible. In one embodiment, for example the swept volume of the impeller is approximately 19,000 mm3, where the blades constitute a volume of approximately 1,200 mm3. The ratio of swept volume to blade volume is therefore approximately 16:1, thereby defining an impeller that is lightweight compared to the smaller, more densely designed and heavier impellers used in conventional blower units.

The lightweight impeller can have a weight for example of less than 2 grams and preferably between 0.8 and 1.8 grams, or more preferably, between 1.2 and 1.7 grams, or even more preferably 1.7 grams. These are just examples of a preferred embodiment and the impeller need not be this weight, but some other weight that renders it lightweight.

Alternatively, a lightweight impeller can be designed to remove as much of the shroud as necessary to bring the moment of inertia to radius ratio down to preferably less than 15 gram*mm, and more preferably between 8-12 gram*mm and in one possible embodiment approximately 11 gram*mm. For example, in one possible embodiment, such an impeller can have a radius of 35 mm, a circumference of 219 mm, and at 15,000 rpm a moment of inertia of 344.22, a tip speed of 54.98 m/s, a pressure of 1,800 Pa and a tip speed to inertia to radius ratio of 3.5 or more and for example 5.59. More generally, a lightweight impeller could have dimensions/parameters within the following ranges (note these ranges are indicative—not limiting): Radius: 15 mm-60 mm; Weight: less than 2 grams; A pressure ratio to inertia to radius ratio of greater than 50:1 Pascals per gram*mm and preferably 80:1 Pa per gram*mm or more at 1,000 Pa.

The lightweight nature of the impeller can be achieved through removing mass through any suitable means, such as removing the shroud and/or material from the impeller and/or using lighter materials. One possible manner in which to reduce impeller mass is to reduce the number of blades.

Motor

Referring to FIGS. 27-31B, a first embodiment of the motor 80 will now be described with reference to the first impeller 90 embodiment by way of example only, although it will be appreciated the motor could alternatively drive the second embodiment impeller 90a or any other suitable impeller design. The motor used to drive the impeller 90 is shown in cross section in FIG. 31A, and various views of the motor components to be described can also be seen in FIGS. 27-30 and 31B. Preferably the motor is a brushless DC motor, or permanent magnet synchronous motor. The controller preferably contains a microcontroller, microprocessor or similar which utilises a sensorless vector control (also termed "field oriented control method"). The central hub 100 of the impeller 90 is engaged with a drive shaft 110 that extends from the motor 80. Mounted to the shaft is a plurality of, preferably small, magnetic segments that form a rotor 112. In one embodiment, the magnet 112 is 20 mm in diameter, but more generally the diameter could be less than 20 mm and preferably between 10 mm to 15 mm. Typically, the magnet volume is less than 1600 mm3 and can be between 500 mm3 and 1600 mm3. Surrounding the rotor 112 is a laminated stator 114 (also see FIG. 30) having a plurality of poles and windings. The windings are selectively energised by the controller via a connector coupled to the winding to facilitate rotation of the rotor 112, and therefore the drive shaft 110 and impeller 90, about the central axis defined by the centerline of the shaft.

The drive shaft 110 is held within the motor by a bearing structure. Preferably the bearing structure has one or more bearings 116 and one or more bearing mounts 118. The bearing mounts 118 as shown engage with the bearings 116 on an inner surface and with the stator assembly on an outer surface. The preferred engagement of the bearing mounts to the bearings and the stator assembly is frictional. To promote a frictional engagement, the bearing mounts 118 are made of a soft, yet resilient and/or flexible material such as silicone rubber or other elastomeric material. The material can be low creep, temperature stable, low compression set with a high tan delta (highly viscous), highly damped. Examples comprise:

Dough Moulding Rubbers like—NBR, Nitrile and Flouro silicone;

Thermo Plastic Elastomers (TPE's) like Santoprene by Exxon;

Thermo Plastic Urethanes like Dynaplast by GLS Corporation;

Heat Cured Casting Urethanes like 10T90 by National Urethanes; and

Multiple other cold cast rubbery compounds like RTV (Room Temperature curing Vulcanites) by Dow Corning, Whacker and others.

Such materials allow the bearing mounts 118 to compress when installed, then expand into their chosen location to be held in place by engagement expanded dimension with a restriction. The mounts 118 are optionally restrained by respective overhangs 119 provided on upper 120a and lower 120b stator mounts (bobbins) of the stator assembly or stator frame between which the stator 114 is sandwiched. The stator frame may be configured as an electrical insulator/isolator. Similarly, the bearings 116 may be restrained by an overhang 118a formed as part of the bearing mounts 118. Either or both of the overhangs may be discretely positioned about the inner and outer annulus of the bearing mounts, or alternatively, extends around the circumference of the mount to define a recess in which the mount is located.

The bearing mounts 118 provide compliance to the rotatable drive shaft 110. As rotatable objects, such as the rotor 112, shaft 110 and impeller 90 usually suffer from some degree of rotational imbalance, the bearing mounts are able to isolate inherent rotation induced vibration from the motor rotor. It has been found that the combination of the lightweight, shroudless impeller having a low rotational inertia, as described above, together with the given compliance of the bearing mounts enables the rotor 112, shaft 110 and impeller 90 to be manufactured and any post manufacture balancing process for the rotating components entirely omitted. These advantages benefit manufacturing costs and time. The lightweight nature of the impeller allows any imbalances to be compensated by the bearing mounts. A lightweight impeller also allows faster speed response of the impeller to changing conditions. Any unwanted fluctuations in pressure due the lack of shroud can be compensated for by quickly changing the impeller speed to return pressure to the desired level.

Figure 31A:
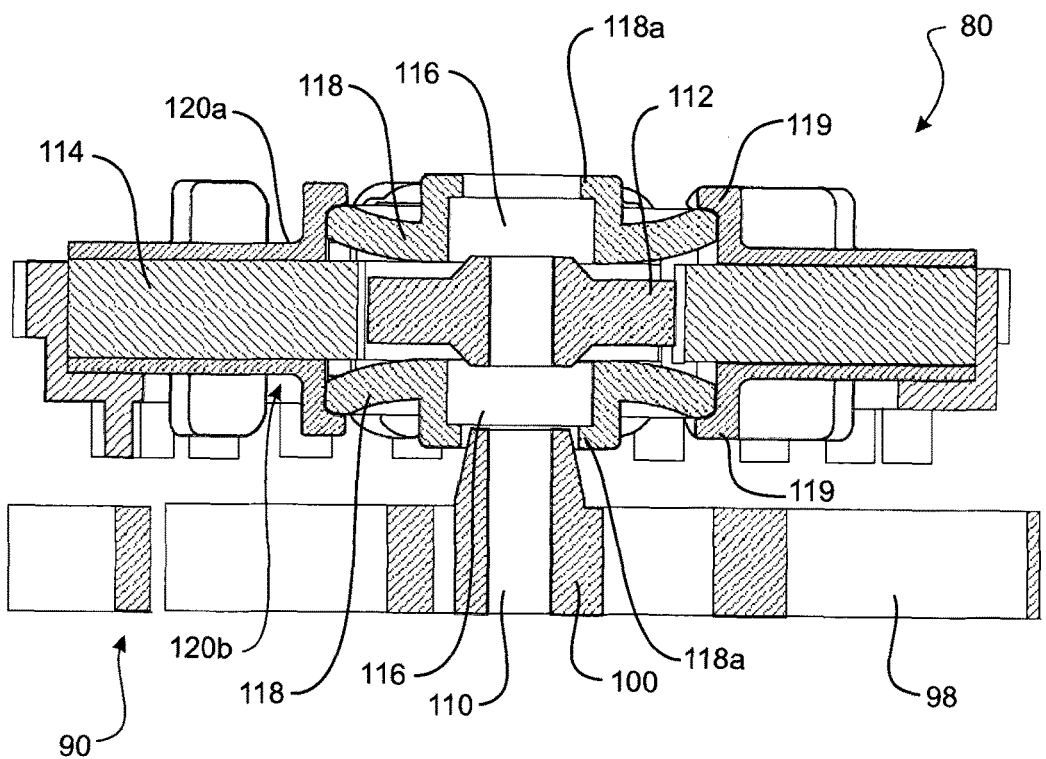
FIG. 31A shows a central cross-sectional view through the motor and impeller assembly of FIG. 27.
Figure 31B:
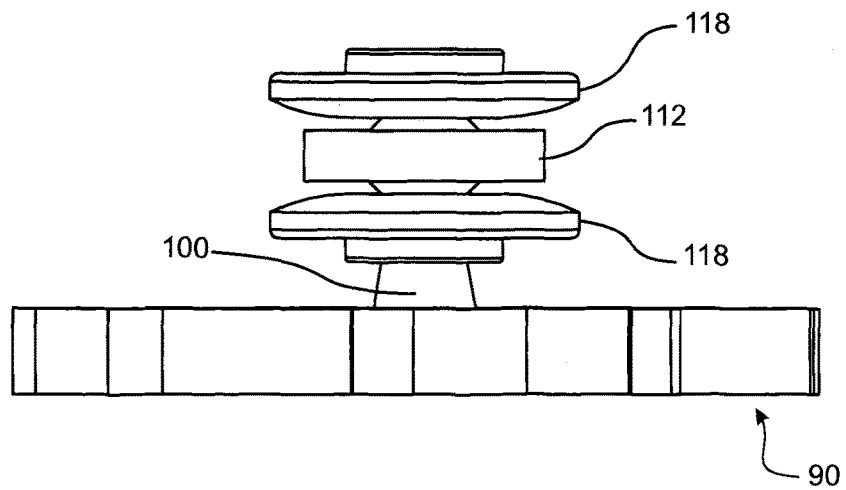
FIG. 31B shows a side elevation view of the upper and lower bearing mounts, magnets, and impeller of the motor and impeller assembly of FIG. 27.

It should be noted that while FIG. 31A shows the bearing mounts 118 mounted within the stator assembly, they may equally be housed externally to the motor. For example, the mounts 118 may instead be mounted within journals formed within the blower casing. FIG. 31B shows the bearing mounts 118 in their compressed form, not their rest form.

Figure 27:
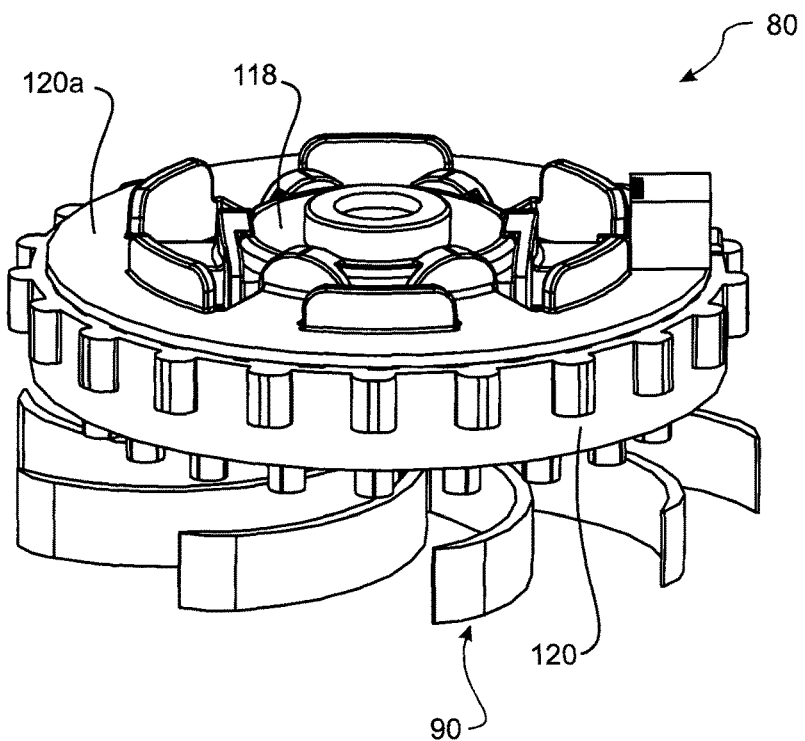
FIG. 27 shows an upper perspective view of the motor and impeller assembly of the blower unit of FIG. 17 in accordance with a first embodiment of the invention.
Figure 28:
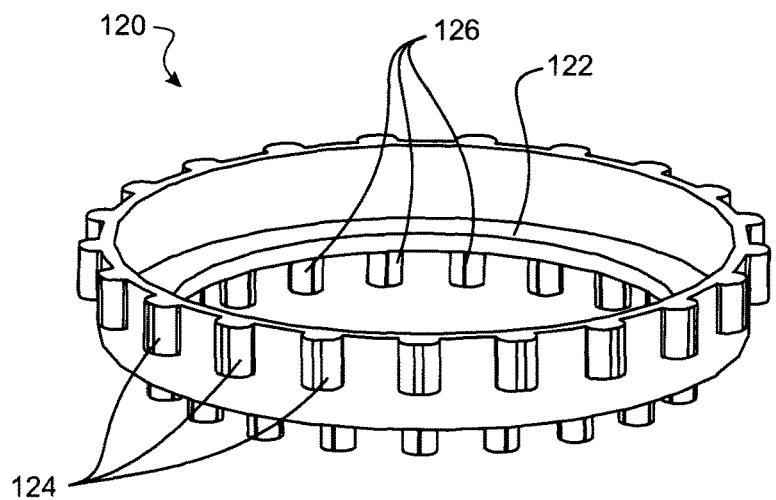
FIG. 28 shows an upper perspective view of a stator isolator of the motor assembly of FIG. 27 in accordance with an embodiment of the invention.
Figure 29:
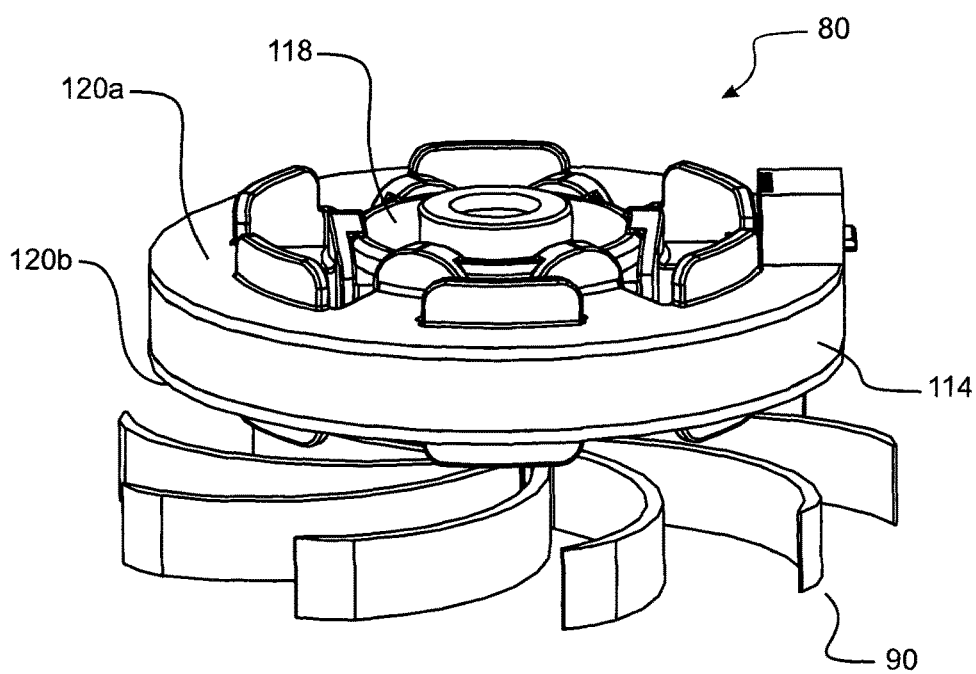
FIG. 29 shows an upper perspective view of the motor and impeller assembly of the blower unit of FIG. 27 with the stator isolator component omitted from view.
Figure 30:
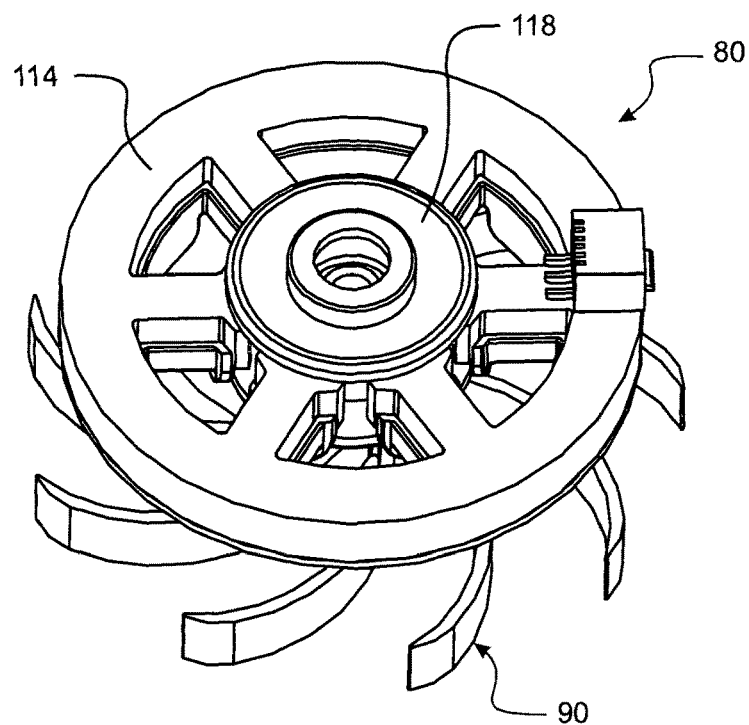
FIG. 30 shows an upper perspective view of the motor and impeller assembly of FIG. 29 but with the upper stator mounting part omitted from view.

To provide further vibration damping of the rotational components of the blower, the motor and impeller, can optionally be mounted on a compliant mounting device. FIG. 28 shows one embodiment of such a mounting device 120. In accordance with an embodiment of the invention, the mount 120 is most preferably made from a soft, flexible yet resilient material such as silicone rubber and may operate as a stator isolator. The mounting device 120 has an internal recess or seat 122 in which the stator is received and retained. Preferably the internal recess is smaller than the outer surface of the motor to encourage an interference fit between these components. FIG. 27 shows the motor 80 positioned within the mounting device 120. In this embodiment, a first set of a plurality of projections 124 extends from the outer peripheral wall of the mounting device 120. Additionally, a second set of a plurality of projections 126 extends beneath the lower surface of the mounting device 120. The projections 124, 126 provide supporting leverage to the mount and motor assembly. During operation of the motor, vibration caused by any imbalance of the rotational components is absorbed by each of the projections 124, 126 by allowing the body of the mount 120 to move relative to the surface on which or against which the projections 124, 126 are supported or are engaged. The first set of projections 124 is configured to abut or engage the inner surface of the peripheral side wall in the upper region 82 of the casing 60. The second set of projections 124 is configured to rest upon or engage with the upper surface of the divider 84 of the casing.

Figure 43:
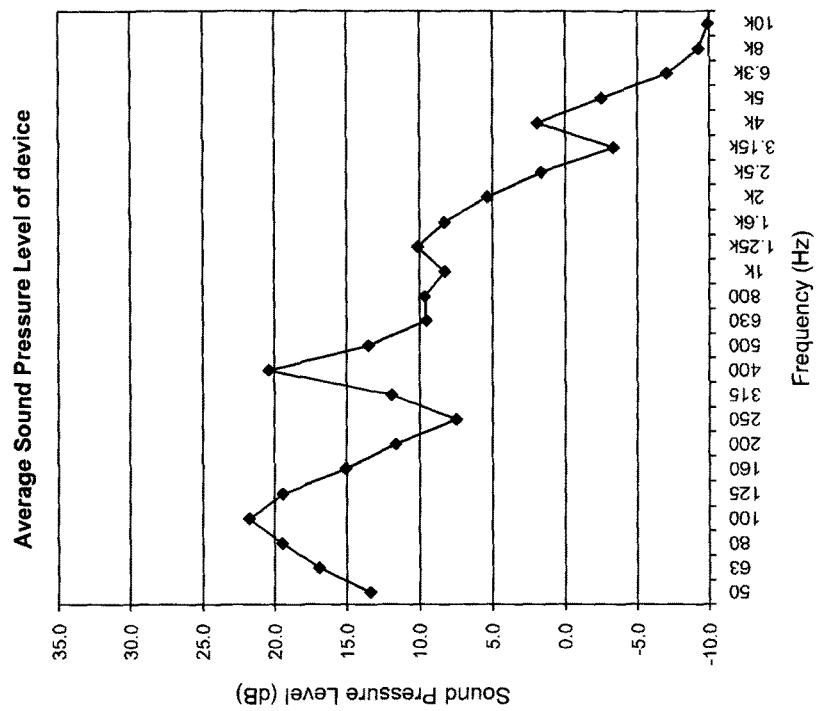
FIG. 43 shows a graph of average sound pressure levels of a blower unit in accordance with an embodiment of the invention.
Figure 42:
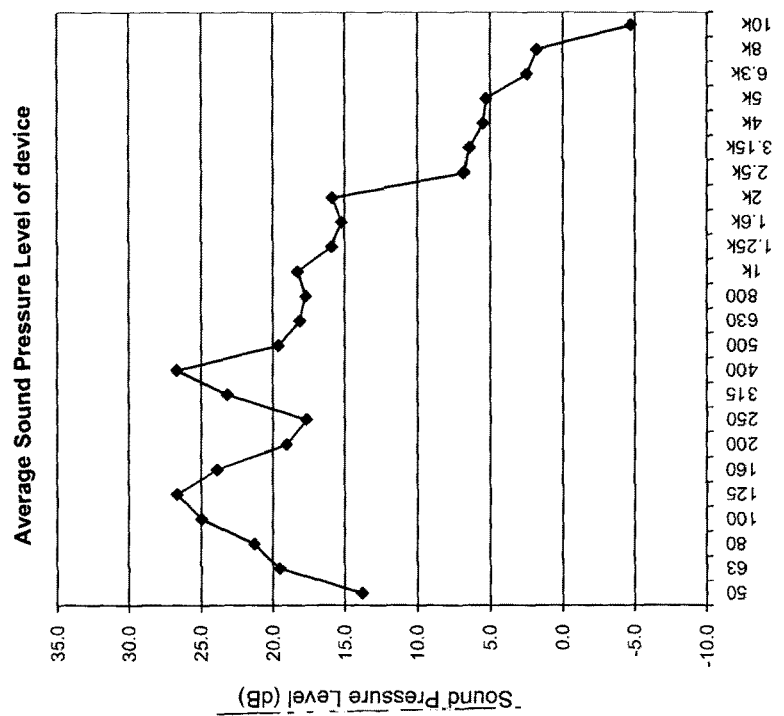
FIG. 42 shows a graph of average sound pressure levels of a conventional blower unit.

FIG. 42 is a graph of the sound pressure level of a conventional blower unit tested in an anechoic chamber. FIG. 43 is a graph of the sound pressure lever of a blower unit according to the embodiment described above. It can be seen that the lightweight and shroudless impeller 90,90a, the flexible bearing mounts 118 and flexible motor mount 120 contribute to a significantly reduced noise output across the tested spectral range of 50 Hz to 10 kHz.

Figure 32A:
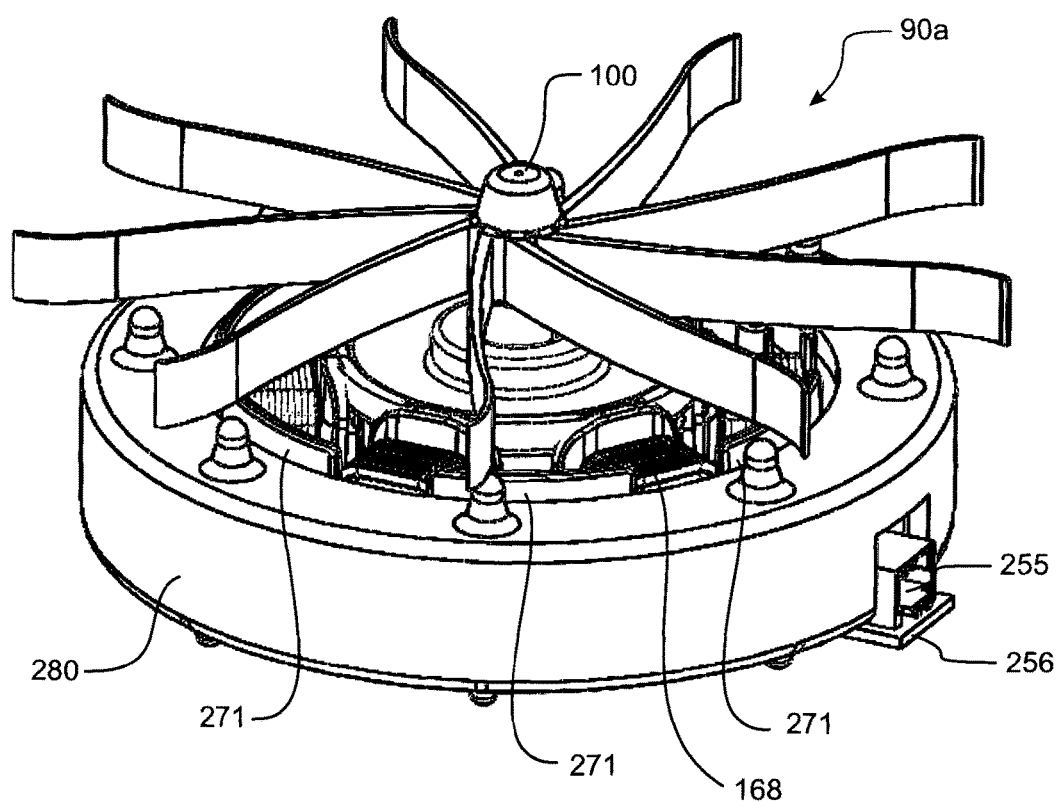
FIG. 32A shows a perspective view of the motor and impeller assembly of the blower unit of FIG. 17 in accordance with a second embodiment of the invention.
Figure 32B:
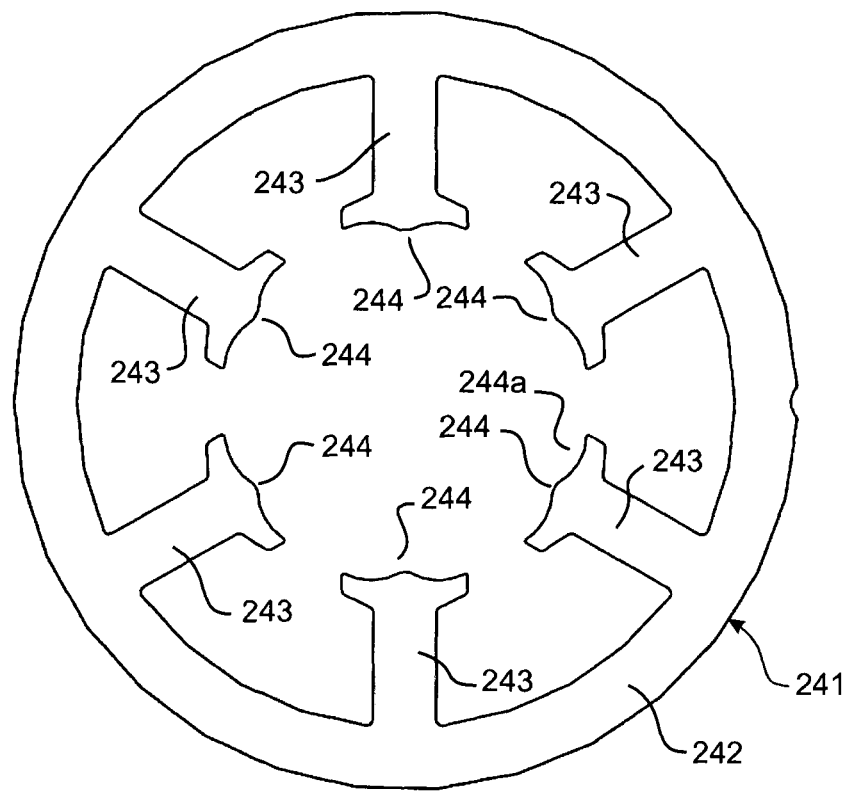
FIG. 32B shows a stator lamination of the second embodiment motor.
Figure 32C:
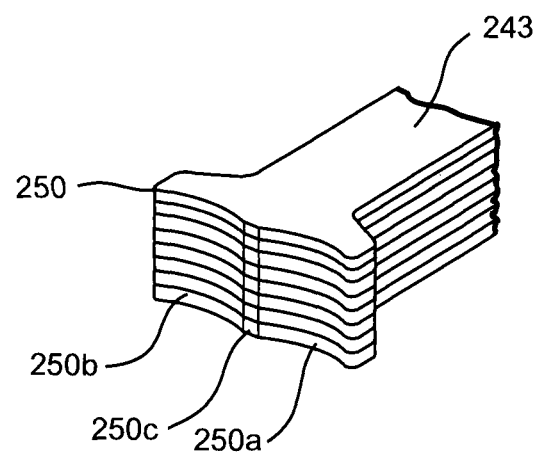
FIG. 32C shows a pole face of the second embodiment motor.
Figure 32D:
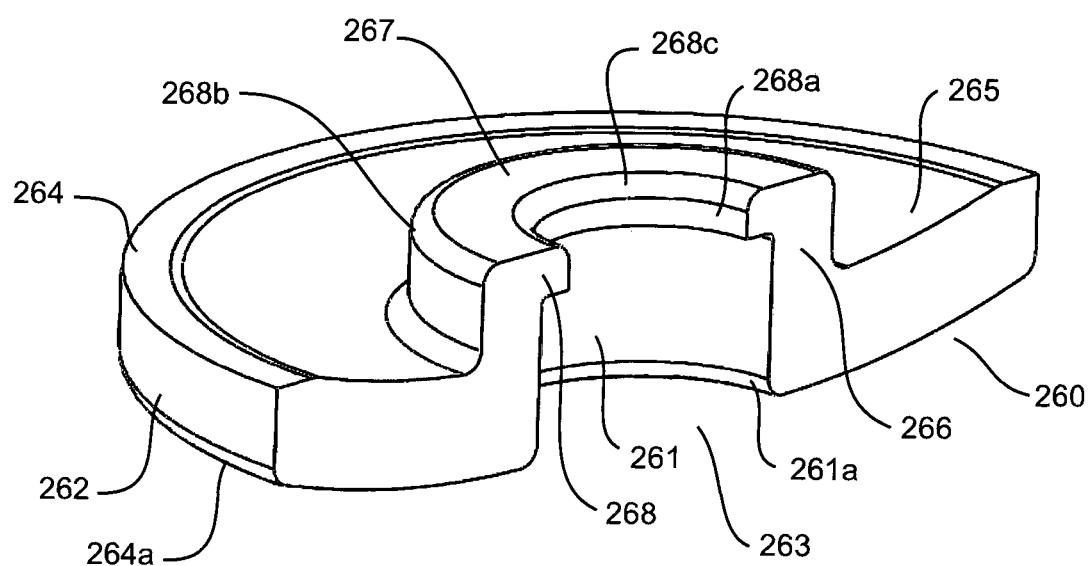
FIG. 32D shows a bearing mount of the second embodiment motor.
Figure 32E:
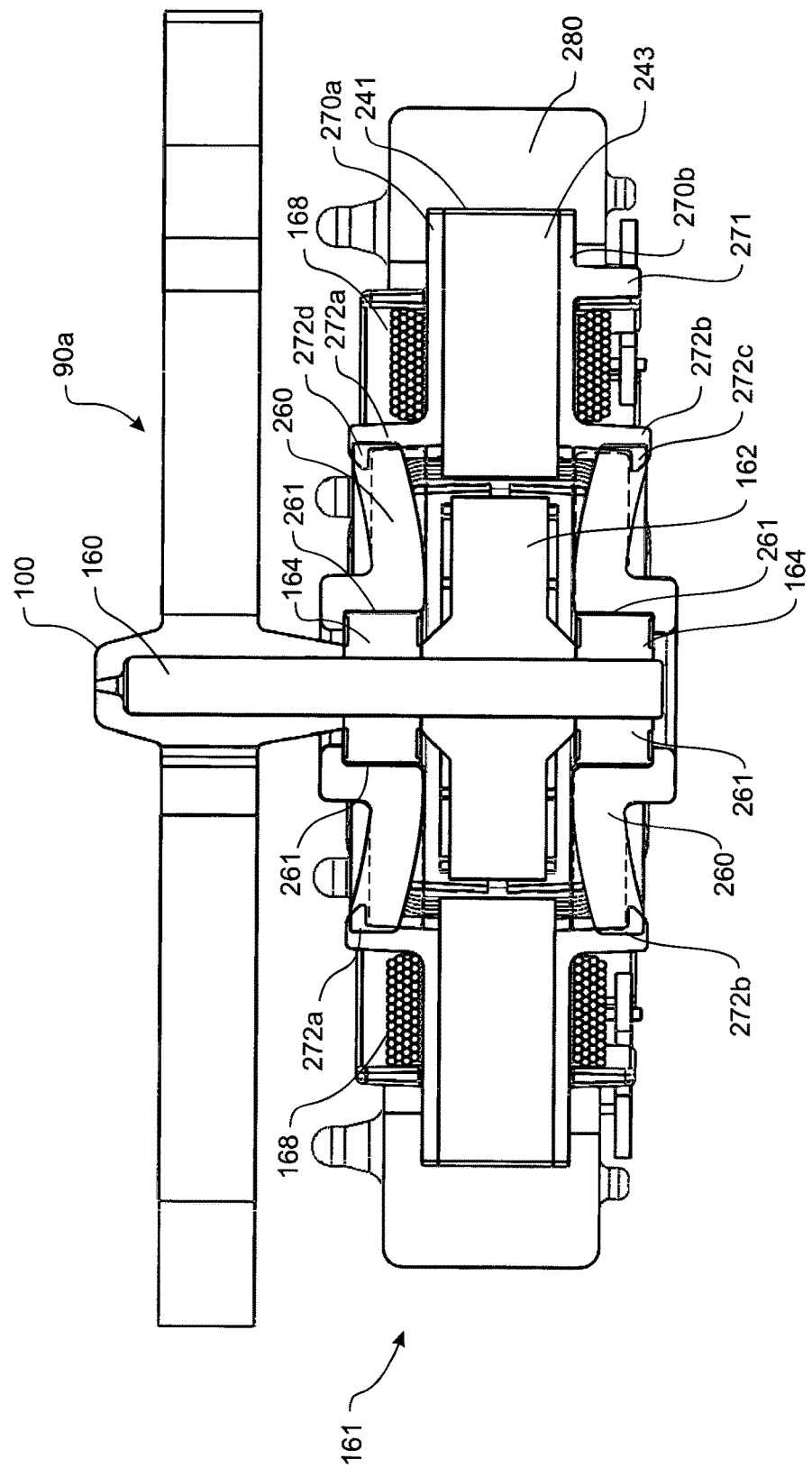
FIG. 32E shows a cross-sectional view of the motor and impeller of the second embodiment.

A second embodiment of the motor and impeller assembly is shown in FIGS. 32A-32F. Many aspects of this embodiment are the same as those in the previous embodiment. Features described in relation to the previous embodiment not described in this embodiment can be assumed to exist in this embodiment where appropriate. Like features will use the same reference numerals as the previous embodiment. The motor used to drive the impeller 90a is shown in cross-section in FIG. 32E. This embodiment of the motor is shown driving impeller 90a, but it will be appreciated that any of the other impeller embodiments described may alternatively be used. Preferably the motor is a brushless DC motor operated using sensorless vector control ("field oriented control") controlled by a microcontroller, microprocessor or similar controller, for example, via a connector 255 mounted to a PCB/substrate 256 (such as shown in FIG. 32A). The control can be tuned to suit a low inertia impeller. Referring to FIGS. 32A, 32B and 32E, the central hub 100 of the impeller 90a is engaged with a shaft 160 that extends from the motor 161. Mounted to the shaft is a plurality of, preferably small, magnetic segments to form a rotor 162. Surrounding the rotor 162 is a laminated stator 241 having an annular outer portion 242 and a plurality of poles 243 and windings 168. The stator is mounted to the PCB or other substrate 256 and the windings 168 coupled to the connector 255. The stator 241 has an electrical insulator/isolator (forming a stator frame) 270a, 270b covering the top and bottom of the annular portion 242 and the poles 243. Each winding 168 is preferably assembled on the insulator 270a, 270b over each pole 243. Protrusions for engagement and retainment are provided around the circumference 271 extending upwards and at the end of the poles extending upwards 272a and downwards 272b.

Referring to the plan view of one of the laminations 240 in FIG. 32B, each lamination comprises an annular outer portion 242 and a pole portion 243 extending radially inwards. The edge 244 of each pole portion 243 includes a wave shape. The wave shape comprises two concave portions 244a, 244b meeting at a central apex 244c. Referring to FIG. 32C, when a plurality of the laminations 240 are stacked to create the stator 241, each pole 243 has an inner radial face 250 with a wave shape as shown in FIG. 32C. The face 250 comprises two concave portions 250a, 250b meeting at a central apex 250c. This arrangement reduces cogging. The stator and/or rotor can have a skewed magnetisation. The windings are selectively energised using the controller via the connector 255 to facilitate rotation of the rotor, and therefore the shaft 160 and impeller 90a, about the central axis defined by the centerline of the shaft 160.

The shaft 160 is held within the motor by a bearing structure. Preferably the bearing structure has one or more bearings 164 and one or more bearing mounts 260 (see FIG. 32D). The bearing mounts 260 as shown engage with the bearings 164 on an inner surface 261 and with the stator 241/insulator 270a/270b on an outer surface as shown in FIG. 32E. The bearing mount 260 comprises a main annular body 265 that curves from a low point at a central aperture 263 to a higher point at the outer circumference 262. The outer circumference comprises an engaging lip 264, preferably with a chamfer 264a on the intersection of the outer circumference 262 with the main annular body 265. The intersection of the inner aperture 263 with the inner circumference 261 of the main body 265 also preferably has a chamfer 261a. An annular wall/boss 266 extends upwardly from the main annular body 265 at the inner aperture 263. The top portion 267 of the annular wall 266 has an overhanging engagement lip 268. The intersection of the lip 268 with the annular wall 266 and with the overhanging lip side wall 268a are preferably chamfered 268b, 268c. The preferred engagement of the bearing mount 260 to the bearings 164 and the stator 241 is frictional. To promote a frictional engagement, the bearing mounts 260 are made of a soft, yet resilient and/or flexible material such as silicone rubber or other elastomeric material. The material can be low creep, temperature stable, low compression set with a high tan delta (highly viscous), highly damped. Possible materials were described in relation to the previous embodiment. Such materials allow the mounts 260 to compress when installed, then expand into their chosen location to be held in place by engagement expanded dimension with a restriction. They also provide compliance.

FIG. 32E shows the bearing mounts in solid lines in the uninstalled/unassembled state, with an upward curvature. The dotted lines show the bearing mounts 260 in the installed/assembled state, clipped in to the stator/insulator 279a, 270b. In the installed state (also called engaged state or configuration) the annular body is engaged with the stator 241 and/or stator frame 270a, 270b and the annular body 265 is coerced from the curved state (shown in solid lines) into an engaged (flat) configuration (shown in dotted lines) that provides preload to the one or more bearings by action of the bearing mount providing bias provided by the resilient/flexible body acting on the stator and/or stator frame and the bearings. The mounts 260 are optionally restrained by an overhang 272c, 272d formed on the insulator 270a, 270b. Similarly, the bearings 164 may be restrained by an overhang 268 formed as part of the boss 266 on the bearing mount 260. Either or both of the overhangs may be discretely positioned about the inner and outer annulus of the bearing mounts, or alternatively, extends around the circumference of the mount to define a recess in which the mount is located. The impeller/shaft/rotor is assembled into the stator 241 by assembling the bearings 164 on the shaft 160, assembling the bearing mounts 260 on the bearings 164 and manipulating the bearing mounts 260 (by hand, jig or other means) so they engage with the stator insulator 270a, 270b at each pole 243. In an alternative embodiment, the bearing mounts 260 are not coupled directly to the stator or insulator 270a/241 but rather are coupled to another structure such as a housing. Any coupling arrangement with any suitable structure can be provided which provides the required functions as set out below.

The bearing mounts 260 provide compliance to the rotatable shaft 160. As rotatable objects, such as the rotor 162, shaft 160 and impeller 90a usually suffer from some degree of rotational imbalance, the bearing mounts are able to isolate inherent rotation induced vibration from the motor rotor. It has been found that combination of the lightweight, shroudless impeller having a low rotational inertia, as described above, together with the given compliance of the bearing mounts enables the rotor 162, shaft 160 and impeller 90a to be manufactured and any post manufacture balancing process for the rotating components entirely omitted. These advantages benefit manufacturing costs and time. The lightweight nature of the impeller 90a allows any imbalances/misalignment to be compensated by the bearing mounts 260—the arrangement is self aligning due to the bearing mount compliance (due to resilience and/or flexibility, for example). The bearing mount construction, including the geometry and material, also provides axial preload on the bearings, e.g. of up to 7 Newtons. The annular nature of the bearing provides consistent/even preload around the bearing 164. The resilient/flexible curved annular body allows the bearing to be installed in place and provide the preload. The annular nature of the bearing mount 260 provides for even preload around the bearing, while the low creep construction material maintains preload. The material of the bearing mounts 260 is also preferably a viscoelastic damping material that provides damping, which reduces the likelihood of resonance during operation of the motor. Such a viscoelastic material can also provide the required resilience/flexibility to provide the preload. An example of such a material is a Thermo Plastic Urethane like Dynaplast by GLS Corporation. Other materials resilient and/or flexible materials mentioned above for the bearing mount 260 could be adapted to provide the required damping by adding mica. A lightweight impeller also allows faster speed response of the impeller to changing conditions. Any unwanted fluctuations in pressure due the lack of shroud can be compensated for by quickly changing the impeller speed to return pressure to the desired level. The bearing mounts also provide vibration isolation.

Figure 32F:
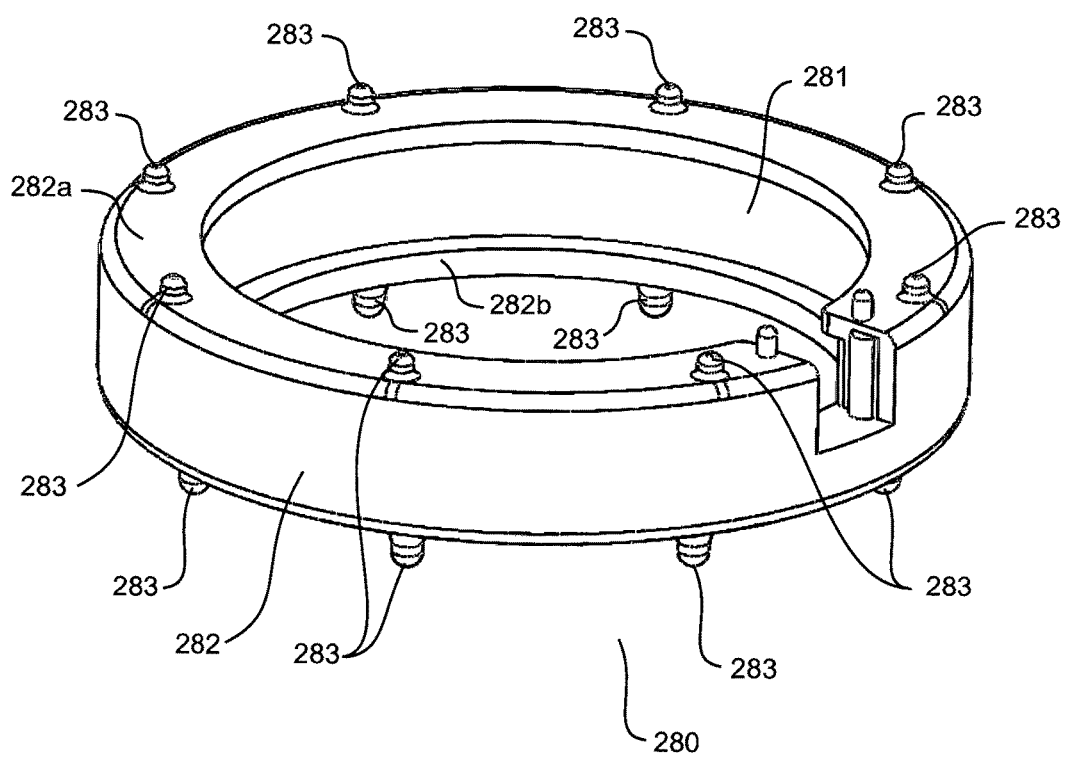
FIG. 32F shows a motor mounting structure of the second embodiment motor.

To provide further vibration damping of the rotational components of the blower, the motor and impeller, can optionally be mounted on a compliant mounting device (motor mount) 280. FIGS. 32A, 32E and 32F show one embodiment of such a mounting device 280. In accordance with an embodiment of the invention the mount is most preferably made from a soft, flexible yet resilient material such as silicone rubber. The mounting device 280 has an annular body 282 with upper and lower engaging lips 282a, 282b that define an internal recess 281 in which the stator 241 is disposed. Preferably the internal recess 281 is smaller than the outer surface of the stator to encourage an interference fit between these components. FIG. 32E shows the motor positioned within the mounting recess 281.

A plurality of projections 283 encircles the upper and lower surfaces of the mount 280. The end of projection extends past the upper and lower surfaces of the mount to provide supporting leverage to the mount and motor assembly. During operation of the motor, vibration caused by any imbalance of the rotational components is absorbed by each of the projections by allowing the body of the mount 280 to move relative to the surface on which the projections 283 are supported.

The description above describes embodiments of a blower unit comprising a lightweight impeller assembly. FIGS. 31A and 32E show embodiments with a metal (e.g. steel) shaft 110,160 assembled on a magnet rotor 112,162. The metal shaft is press fit into an aperture in the magnet rotor. This requires fine tolerance control to ensure a good tight fit to reduce slipping. However, the fit should not be so tight as to risk cracking the magnet rotor.

Alternative shaft and magnet rotor assemblies are shown in FIGS. 33A to 33F, which can be used in the stator in place of the assembly shown in FIG. 31A or 32E.

FIGS. 33A, 33B1-33B3 and 33C1-33C4 show a possible alternative rotor assembly of the embodiments described above. The assembly comprises a metal shaft 400 (see FIGS. 33C1-33C4) and a magnet rotor 401. The magnet rotor 401 has a central opening 402. The central opening 402 comprises a central portion with indents 403*a* to 403*d*. The central opening also comprises a profiled edge through a central cross-section providing a stepped ledge 408 (see FIGS. 33B1-33B3).

Figure 33A:
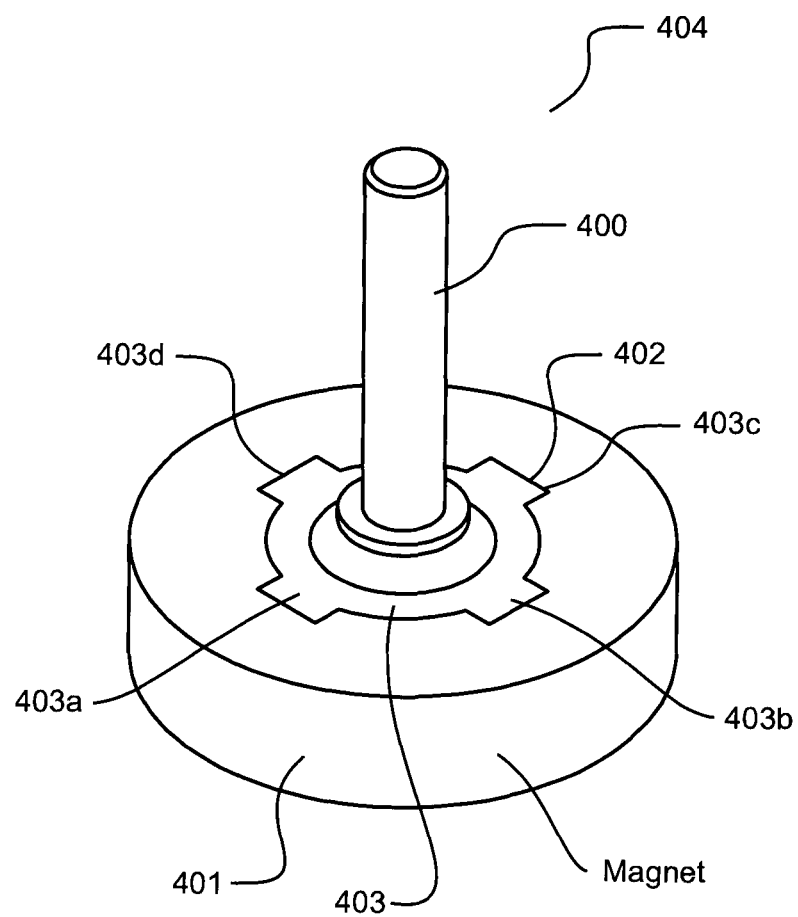
Figure 33E:
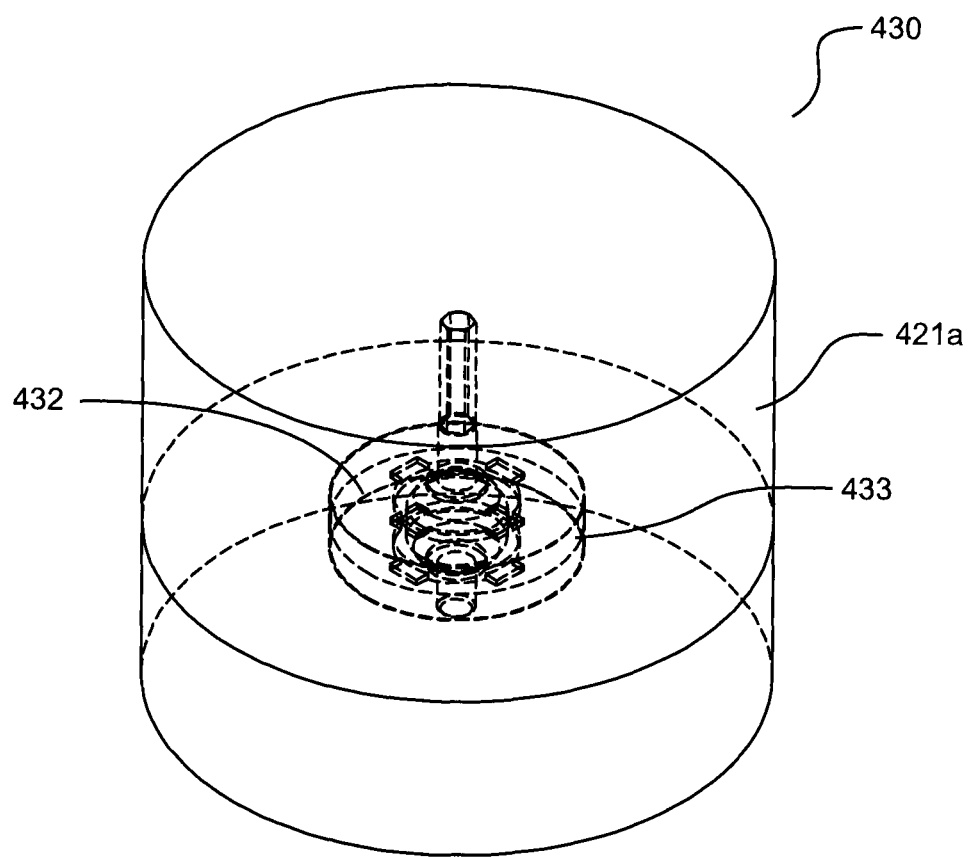
Figure 33G:
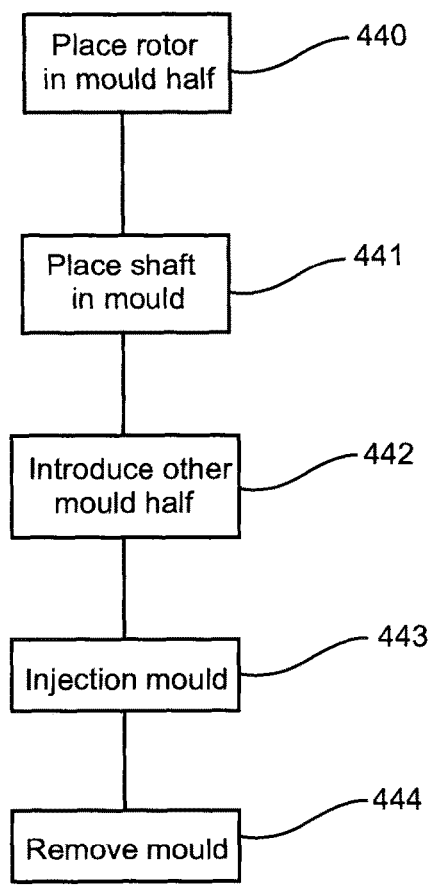
FIG. 33G shows a flow diagram of an injection moulding process for the metal shaft/insert rotor assembly.

The metal shaft 400 has a knurled section 409*b* in its exterior and extends through the central opening 402. A plastic insert 403 is injection moulded between the shaft 400 and the magnet rotor 401 in the central opening 402. The plastic insert 403 is overmoulded onto the stepped ledge 408 of the magnet rotor. This provides an insert 403 with a similar exterior shape to the central opening 402. An interlocking (cog dog) is formed between the shaft 400 and overmoulded (insert) material 403, so that the metal shaft knurled section 409*b* engages with the overmoulded insert 403 to couple the shaft 400 to the magnet rotor 401. The assembly 404 can be used in the embodiments described above such as in FIGS. 31A and 32E, wherein the shaft 110,160 and magnet rotor 112,162 of those embodiments are replaced with the metal shaft 400/plastic insert 403/magnet rotor 401 assembly 404 as described in FIGS. 33A, 33B and 32C. The assembly can be created as shown in FIG. 33G. The rotor is placed in a mould, step 440, the shaft is introduced, step 441, the other mould half is introduced, step 442, the insert is injection moulded between the shaft/rotor, step 443, and then the mould removed, step 444.

Figure 4:
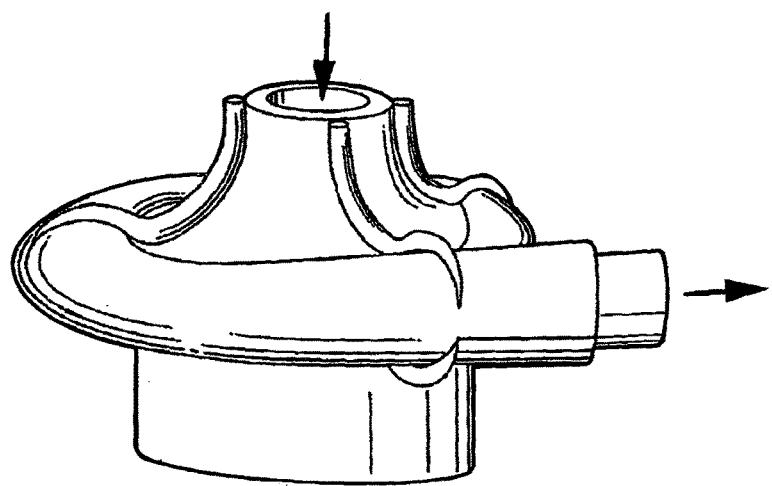
FIG. 4 shows a side view of the blower unit of FIG. 3.

FIGS. 33D1-33D4 show plan, elevation and isometric views of a magnet rotor and shaft assembly 420 according to another alternative embodiment. The assembly 420 comprises a rotor 401 formed from a magnet material. The magnet rotor 401 has a central opening 402. The central opening 402 comprises a central portion with indents 403*a* to 403*d*. The central opening also comprises a profiled edge through a central cross-section providing a stepped ledge 408.

The assembly 420 also comprises a plastic shaft 421 that extends through the centre of the insert opening 410 and is overmoulded onto the magnet rotor 401 as will described below. When overmoulded, the shaft comprises an integral overmould magnet insert portion 423. The shaft 421 can be formed to comprise a hex 422 or other location profile for press fit coupling with the impeller. The plastic shaft 421 comprises any suitable plastic or combination thereof, such as acety or polypropylene, although any suitable injection moulding or other plastic could be used.

The assembly 420 can be used in the embodiments described above such as in FIGS. 31A and 32E, wherein the shaft 110,160 and magnet rotor 112,162 of those embodiments are replaced with the plastic shaft 421/magnet rotor 401 assembly 420 as described in FIGS. 33D1-33D4.

Figure 33H:
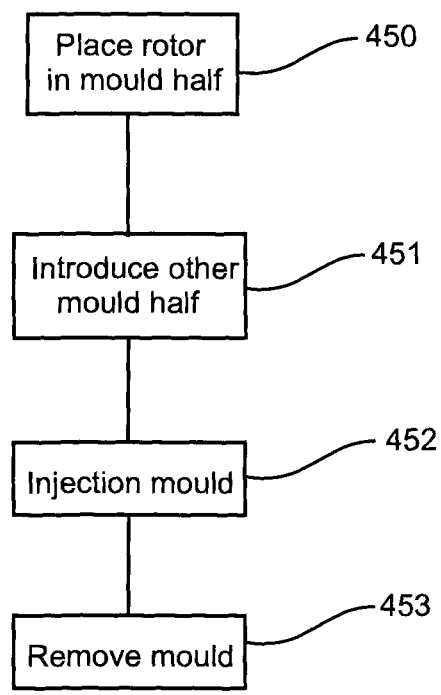
FIG. 33H shows a flow diagram of an injection moulding process for the plastic shaft rotor assembly.

FIGS. 33E and 33F1-33F3 show an injection moulding tool that can be used to manufacture the shaft/rotor assembly 420, and FIG. 33H is a flow diagram of a method of manufacture. The tool 420 is an open and close two-part mould tool comprising a first mould part/portion 431*a* and a second mould part/portion 431*b* that come together to form a mould/cavity 432 comprising a magnet jig 433. The mould comprises a cavity to form the shaft 421, hex fit shape 422 and overmould portion 423. During manufacture of the assembly 420, a magnet rotor 401 with an opening 402 as described above is introduced into the mould and placed in position in one half of the mould forming the jig 433, step 450. The top portion 421*a* of the mould is placed in position to create the mould cavity 432 with the bottom portion 421*b*, step 451. An injection moulding process starts, step 452, to injection mould plastic to create the shaft 421 overmoulded onto the magnet rotor 401. The injection moulding process overmoulds plastic over the stepped ledge 408 portion of the rotor magnet 401 to create the insert portion 423. Once the injection moulding process is complete, the mould portions 421*a*, 421*b* are removed leaving the assembly 420, step 453. The assembly 420 can then be used in the motor of FIG. 31A or FIG. 32E, for example.

Previously, it has not been possible to use a plastic shaft/rotor assembly in the motor of a blower of a CPAP machine or similar. A plastic shaft is not sufficiently strong to withstand the forces involved in such motors. However, in the lightweight impeller embodiments described above, the forces are such that a plastic shaft rotor becomes a possibility. The lightweight and low inertia nature of the rotor along with the compliant bearing mount and other features that reduce unbalancing forces and other forces enable the use of a plastic shaft. Both the plastic rotor assembly and the method of manufacture provide advantages over existing metal shaft rotors.

The combination of various features of the motor and impeller provide advantages, which can be achieved using a single impeller. Using a lightweight/low inertia impeller (e.g. by removing some or all of the shroud and/or reducing blade material) reduces imbalance of the impeller due to manufacturing tolerances. Previously, after manufacture and during assembly of a blower, it has been necessary to remove/add material to the impeller to improve balancing. The lightweight nature of the impeller means that any small imbalance can be tolerated without requiring rectification. Coupled to this, where the imbalance is not small enough, the resilient/flexible bearing structure mounts 118 and/or stator mount 120 can compensate for any imbalance in the impeller. As the impeller is lightweight enough, any imbalance is of a small enough magnitude to be compensated for by the bearing structure mounts 118, without the need for altering the weight of the impeller during assembly. In addition to this, small magnets in the motor (combined with the bearing structure) remove the need for balancing during assembly, and improve dynamic performance.

The resilient/flexible bearing structure allows for self-alignment, compliance, damping and preload of the impeller and shaft assembly. This makes assembly easier, and in combination with the lightweight/low inertia impeller reduce or negates the need for balancing modifications during assembly, as mentioned previously. The bearing structure provides for relaxed tolerances during manufacture as it compensates for larger tolerances. The bearing structure also isolates and/or damps vibrations, also allowing high RPM speeds of the impeller where necessary. The stator frame/motor mount also provides vibration isolation.

The configuration of the casing that separates the blower into different interior regions separates out the high velocity region to reduce noise. This allows for and maintains a constant high velocity of flow while diffusing the velocity to pressure.

The use of a plastic shaft also provides a number of benefits over a metal (e.g. steel) shaft, including (but not limited to) the following:

The reliability risks associated with dissimilar materials are reduced.

The knurled interface between the cog/dog insert and the shaft does not have to be monitored for cracking, slipping, run out, shrinkage, fluid ingress/corrosion.

The impeller to shaft interface is improved and carries similar reduced reliability risks. It is less prone to cracking because of similar thermal expansion (due to plastic on plastic press fitting). There is reduced chance of slipping because of the opportunity to add some keying feature like a hex or grooves.

The plastic shaft assembly is a press fit rather than a sliding fit so is more stable with less chance of rattles.

The cost relative to a metal shaft is reduced. This is because of the following:

Manufacturing the shaft to the tolerance for a sliding fit is not required because the plasticity of the plastic shaft allows for much wider tolerance or inaccuracy to press fit the bearings.

The need for grinding of the shaft after knurling to re-establish straightness is not required.

The handling and inserting the shaft into the mould is not required.

It is possible to use materials with better vibration absorption properties than steel.

Ease of assembly can be improved by reducing the length of the bearing press fit engagement by reducing shaft diameter with a hex, undercutting the impeller side of the shaft.

In general, the following advantages of the motor and impeller in this embodiment are provided for by the combination of one or more features as follows:

| Advantage | Features providing advantage |
| --- | --- |
| Low noise impeller | Provide different regions in the casing, one containing the impeller |
| | Low cogging torque |
| | Sensorless vector drive/field oriented control |
| Fast responding blower | Low inertia impeller (achieved through shroudless/lightweight construction) |
| | Small magnet with diameter less than 20 mm |
| | Sensorless vector drive |
| Lower cost | No balancing required during assembly |
| | Small volume magnet |
| | Simple bearing mount |
| | One piece impeller |
| Assembly without balancing | Low inertia impeller/lightweight |
| | Flexible/resilient bearing structure |
| | Motor mount/stator frame isolator |
| | Low RPM impeller |
| | Small magnet with diameter less than 20 mm |
| | One piece impeller |
| Large diameter impeller/Low RPM | Low inertia impeller |
| Simplified manufacture, lower costs, better reliability | Use of plastic shaft which becomes possible due to lightweight impeller, balancing advantages and other features |

Headgear

Referring to FIGS. 34-39, embodiments of various headgear configurations for securing the respiratory device 20 to the user's head will be described in further detail. These embodiments are provided by way of example only and it will be appreciated by those skilled in the art of respiratory device patient interfaces that various alternative headgear configurations could alternatively be used. Typically, the headgear comprises one or more headstraps that are connected to the respiratory device and which extend around the user's head to secure or mount the respiratory device to the user's head.

Figure 34:
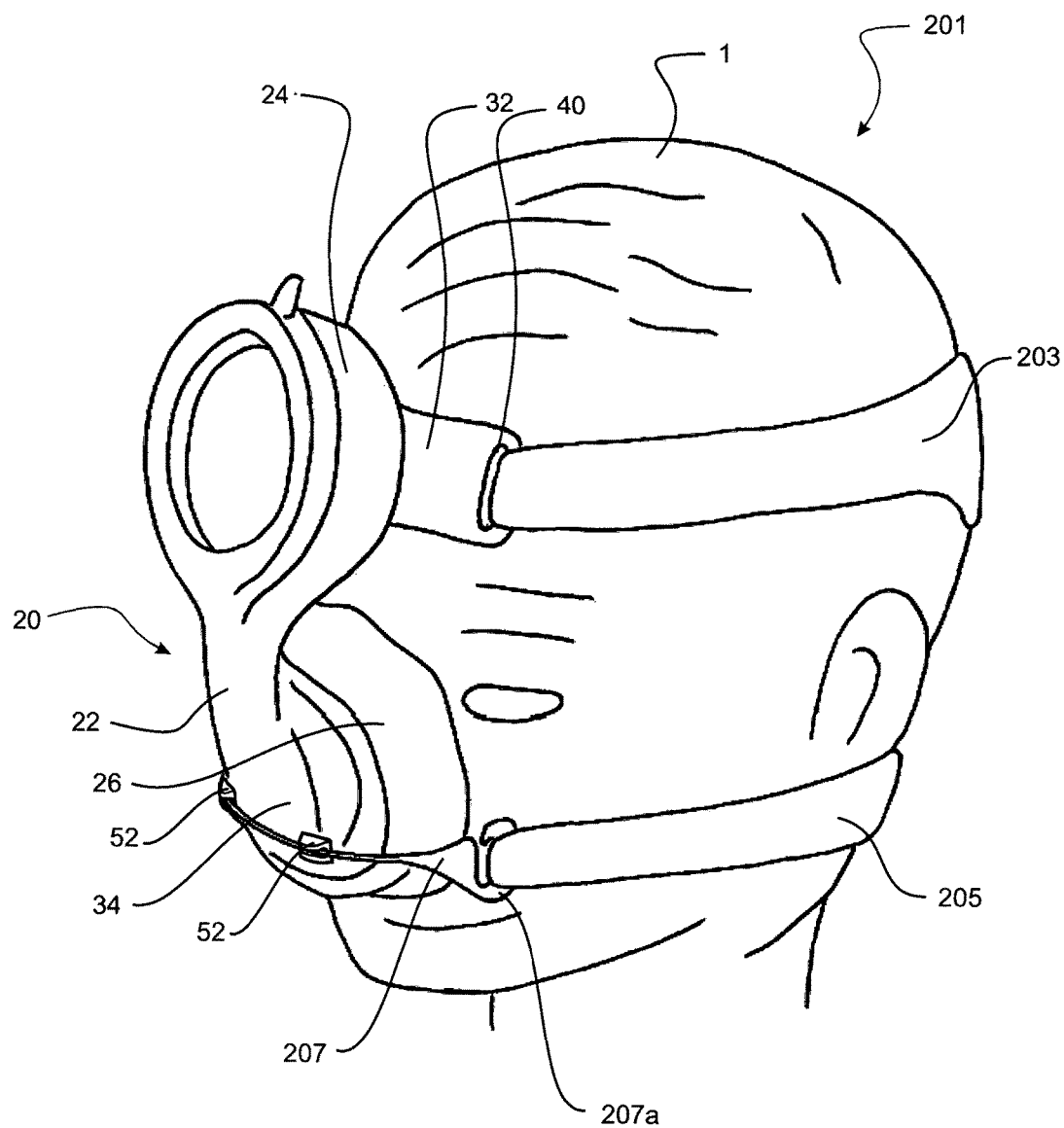
FIG. 34 shows a perspective view of the respiratory assistance apparatus of FIG. 7 worn by a user and mounted to the user's head by headgear in accordance with an embodiment of the invention.

Referring to FIG. 34, a first embodiment of the headgear 201 for securing the respiratory device 20 to a user's 1 head is shown. In this embodiment, the headgear comprises an upper headgear strap 203 that is coupled at each end to a respective side of the forehead support 32 and which extends around the back of the user's head at a height that is in the forehead region of the user's head above their ears. In particular, each end of the headgear strap 203 is coupled or connected to a respective connection aperture 40 provided in forehead support 32 of the main body 22. The headgear 201 also comprises a lower headgear strap 205 that is configured to secure or hold the lower part of the respiratory device 20 in the region of the mask 26 against the user's face and is primarily configured to hold the mask 26 in a sealed engagement with the user's face around their nose. The headgear straps 203,205 in this embodiment are formed from a laminated sheet of open cell foam sandwiched between two sheets of textile fabric, although any other suitable material could be used.

In this embodiment, the lower headgear strap 205 is connected to the mask body 34 of the main body 22 of the respiratory device by an elongate glider member 207. In particular, the elongate glider member extends across the front of the mask body 34 and attaches to the mask body via at least one clip 52. In this embodiment, the elongate glider member 207 may slide or glide within the clips 52 so that the mask assembly may move laterally with respect to the headgear strap 205. The lower headgear strap 205 is coupled at either end to a respective end of elongate glider member 207. In this embodiment, each end of the lower strap 205 is coupled or looped about a hook formation 207a formed at each end of the elongate glider member 207. In alternative embodiments, it will be appreciated that a fixed or static arrangement for the connection of the lower strap to the mask body may be employed.

Integrated Battery Headgear

Figure 35A:
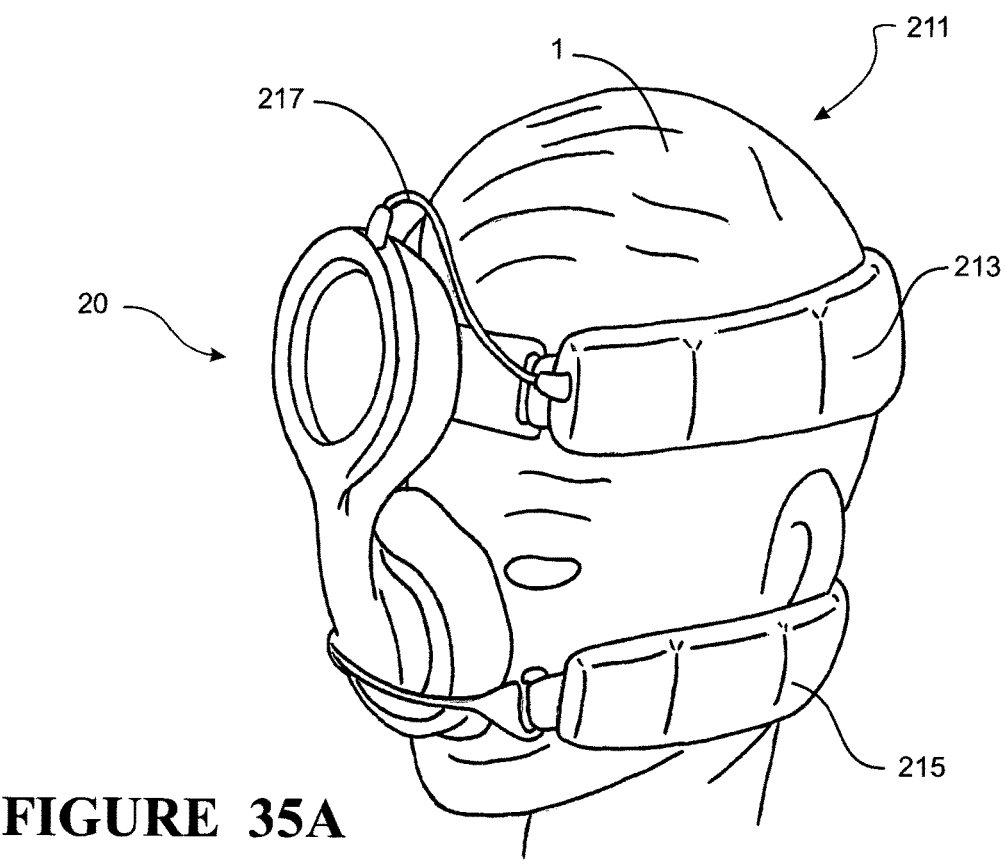
FIG. 35A shows a perspective view of the respiratory assistance apparatus of FIG. 7 worn by a user and mounted to the user's head by headgear in accordance with another embodiment of the invention in which the headgear has batteries integrated into the upper and/or lower head straps.

Referring to FIG. 35A, a second embodiment 211 of the headgear for mounting the respiratory device 20 to the user's 1 head is shown. In this embodiment, the headgear 201 comprises upper 213 and lower 215 headgear straps that are coupled to the respiratory device in a similar manner to the upper and lower headgear straps described with respect to the headgear embodiment 201 of FIG. 34. However, in this embodiment the power supply module or modules of the respiratory device, which may be in the form of one or more battery packages that are integrated, fixed or mounted to the headgear. In this embodiment, either or both of the upper 213 and lower 215 headgear strap comprise integrated battery packs or battery modules that are connected together and configured to supply power to the respiratory device 20 via a power loom or cable 217 which is connected to the batteries.

The batteries may be integrated within the straps 213, 215 in various ways. In one embodiment, the straps may be formed of material comprising internal pouches, pockets or chambers within which the batteries are retained. The recesses or cavities in the head straps may be sealed or openable for the removal and replacement of batteries if desired. The battery packs need not necessarily be mounted within or inside the headgear. For example, the one or more battery pack or packages may be releasably mounted to any part of the headgear such that they are detachable from the headgear.

Typically the type and configuration of the batteries will be selected based on parameters such as energy density per volume and mass, ie, Watt-hours per kilogram, and Watt-hours per cubic centimeter. Some embodiments may employ high density batteries such as Lithium-polymer and Lithium-Ion batteries. Alternatively, it will be appreciated that non-rechargeable or disposable batteries may alternatively be employed if desired.

Figure 35B:
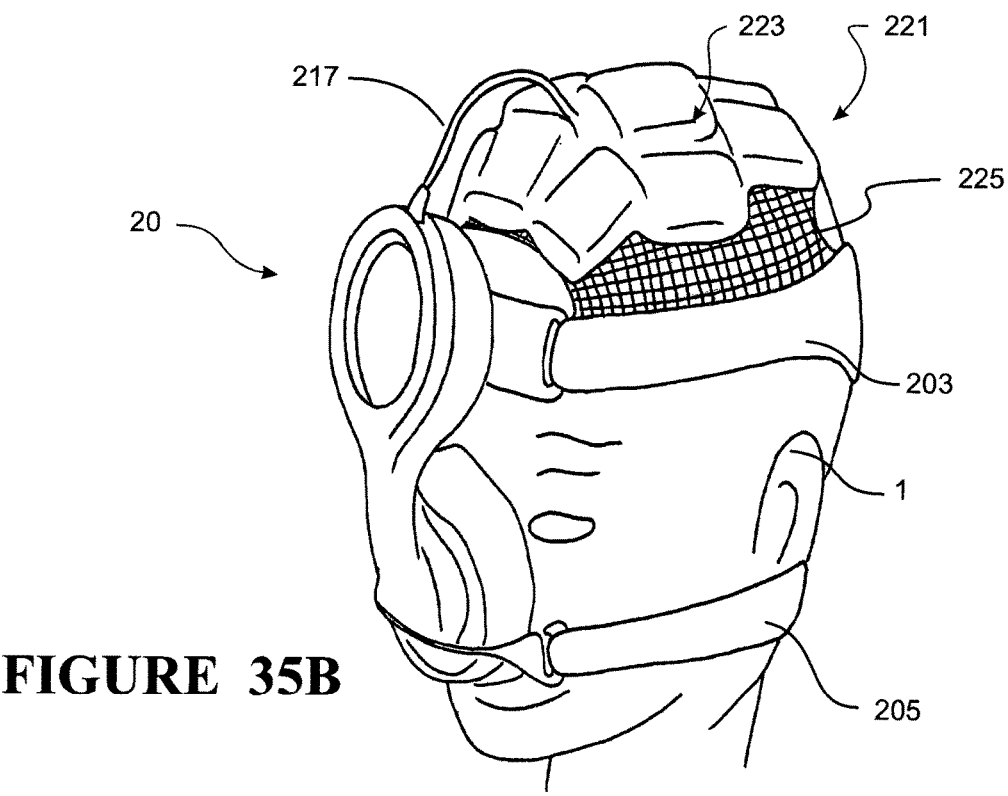
FIG. 35B shows a perspective view of the respiratory assistance apparatus of FIG. 7 worn by a user and mounted to the user's head by headgear in accordance with another embodiment of the invention having upper and lower head straps and battery module mounted to the top of the user's head.

Referring to FIG. 35B, a third embodiment of the headgear 221 is shown for mounting the respiratory device 20 to the user's head. Again, the headgear 221 is provided with an upper 203 and lower 205 head straps of the type described with respect to the first embodiment headgear 201 in FIG. 34. Additionally, a flexible battery package module 223 is provided which is configured to extend at least partially over the top of the user's head and with the battery package module 223 being secured to the upper strap 203 of the headgear via webbed or mesh material. In particular, a base layer of material, whether webbed, mesh or other flexible material, is configured to extend over at least a part of the top of the user's head and which is secured on either side of the user's head to the upper strap 203. The battery package module 223 may comprise one or more batteries that supply power to the respiratory device via power cable 217 as described with reference to FIG. 35A. The battery package module 223 may comprise flexible material which has internal pouches, pockets or recesses for securely receiving and retaining one or more batteries.

In these embodiments in which the battery packs are provided in or otherwise mounted to the headgear, the headgear may also comprise one or more shielding plates that are located between the batteries and the user's head when the headgear is being worn. The shielding plate or plates provide a physical and electromagnetic shield for the user. In some embodiments, the shielding plates may be formed from a metallic material. In some embodiments, the shielding plates may be embedded inside or integrated with the headgear material for user comfort. Alternatively, the shielding plates may be fixed or releasably mounted to the headgear in other suitable ways.

Further Alternative Headgear Configurations

FIGS. 36-39 show various other respiratory device configurations and alternative headgear configurations, although the operation and functionality is similar to that previously described in regard to the respiratory device 20.

Figure 36:
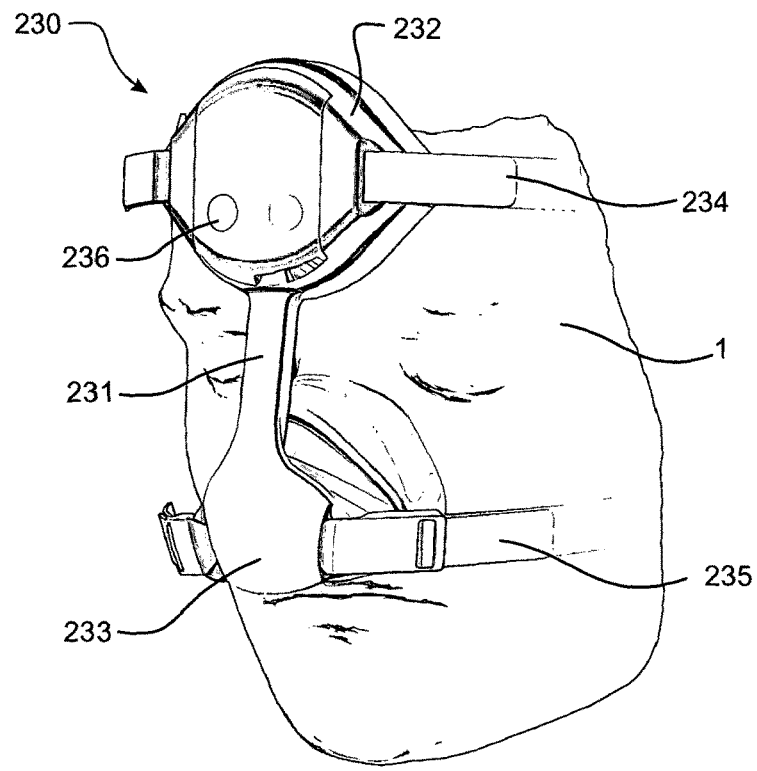
FIG. 36 shows a perspective view of a wearable respiratory assistance apparatus mounted to a user's head in accordance with an alternative embodiment of the invention.
Figure 37:
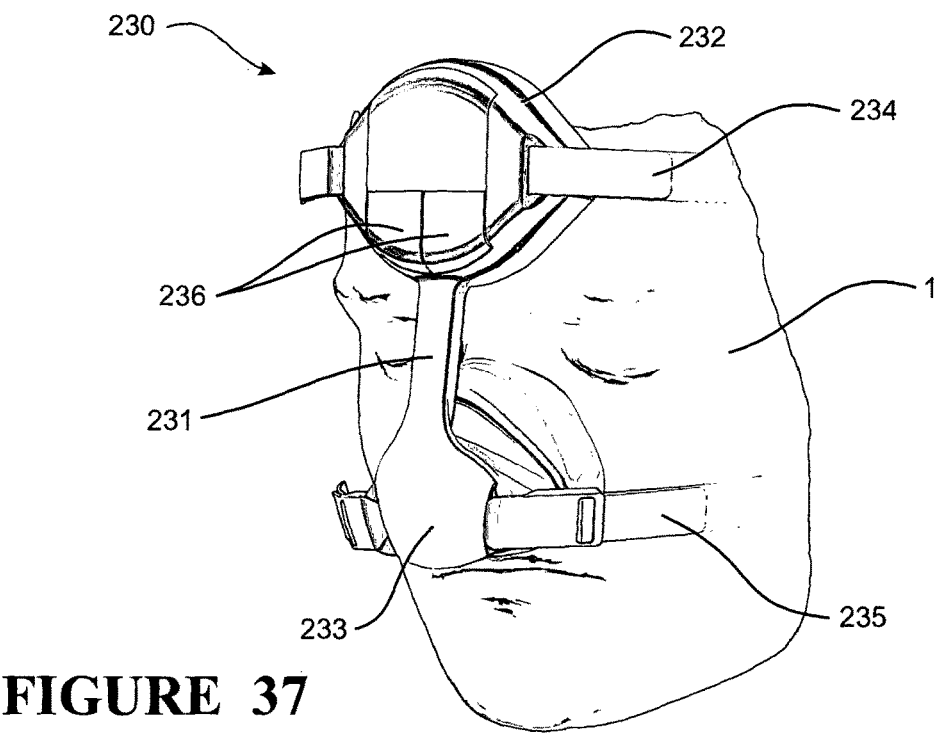
FIG. 37 shows a perspective view of a wearable respiratory assistance apparatus mounted to a user's head in accordance with another alternative embodiment of the invention.
Figure 38:
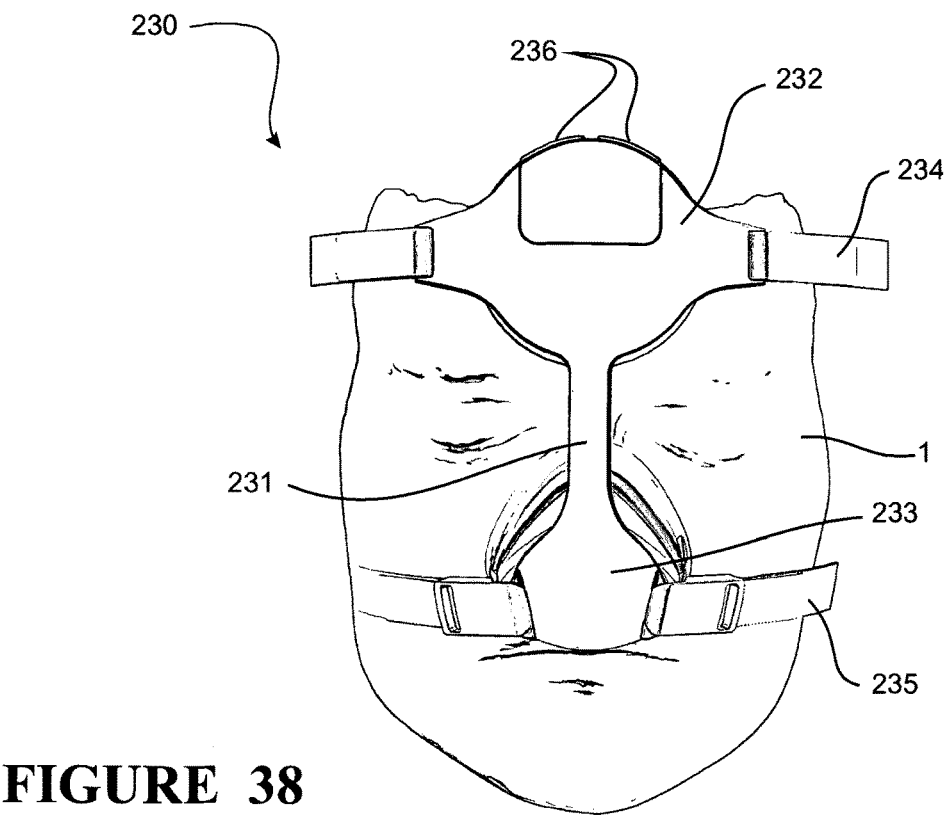
FIG. 38 shows a front view of a wearable respiratory assistance apparatus mounted to a user's head in accordance with another alternative embodiment of the invention.
Figure 39:
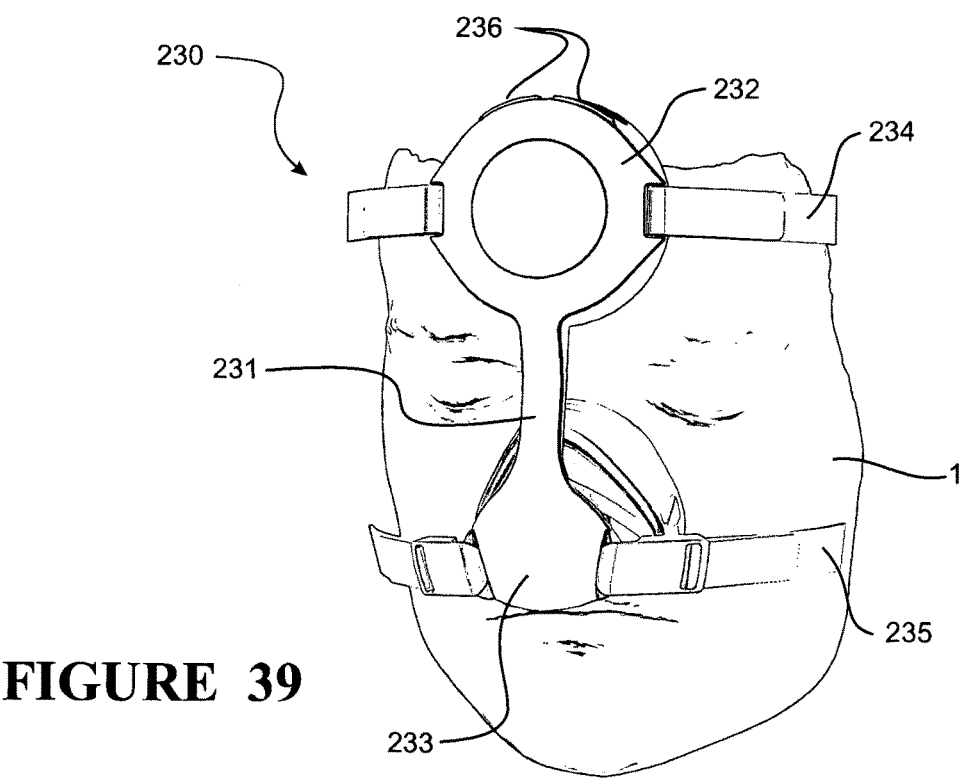
FIG. 39 shows a perspective view of a wearable respiratory assistance apparatus mounted to the head of a user in accordance with another alternative embodiment of the invention.

FIG. 36 shows a respiratory device 230 comprising a main housing 231 having a blower unit 232 located at the top of the respiratory device and which is configured to be mounted in the forehead region of the user 1, a mask assembly 233, and main body 231. The headgear of the respiratory device comprises upper 234 and lower 235 headgear straps that are configured to secure the respiratory device to the user in a manner described with reference to FIGS. 34-35B. In this embodiment, the blower unit 232 is provided with one or more user operable control buttons 236 for the user interface, and which may be configured to switch the blower unit on and off, and/or control one or more operational modes. FIGS. 37-39 show the respiratory device 203 with various different control button 236 configurations. The user interface may comprise a single button, 2 buttons, or multiple buttons, which may act independently or interactively to control one or more operational modes and/or functions of the device. It will be appreciated that the control button or buttons may be any form of tactile switch, dial, or knob, or a touch-sensitive or any other operable user interface mechanism. In some embodiments, the control button or buttons are located on the front face of the blower unit in the forehead region of the respiratory device, but may alternatively be located on the main body or patient interface or other regions of the respiratory device if desired.

Base Station Configurations

With reference to FIGS. 44-50, various base station configurations for a wearable respiratory device of the type or types previously explained will be described in further detail by way of example only. Various wireless power transfer configurations are explained, and the typical connectivity range between the transmitter and receiver of such systems may be in some embodiments upto 2 m, but it will be appreciated that higher ranges may be achieved depending on the hardware employed. It will be appreciated that the features of the various base station embodiments may be combined and interchanged as desired to form further configurations.

In overview, in various embodiments, the base stations may comprise any one or more of the following modules or systems: a power supply system that is operable to supply power to the head-mounted respiratory device; a data transfer system that is operable to send and receive data to and from the head-mounted respiratory device; and a control system that is operable to control the head-mounted respiratory device via control signals. The control system may operate automatically and/or may comprise an operable user interface to enable a user to control the head-mounted respiratory device. Each of these systems may operatively connect to the head-mounted respiratory device via hard-wiring, such as a connection cable, and/or wirelessly over a wireless medium.

In some embodiments, the base station is additionally configured as a physical docking station upon which the head-mounted respiratory device may be stored and/or mounted when not in use. However, in other embodiments the base station carries out the power supply, data transfer, and/or control aspects when connected via hardwiring or in wireless connectivity range.

First Embodiment Base Station—with Separate Wireless Power Transfer Mat

Figure 44:
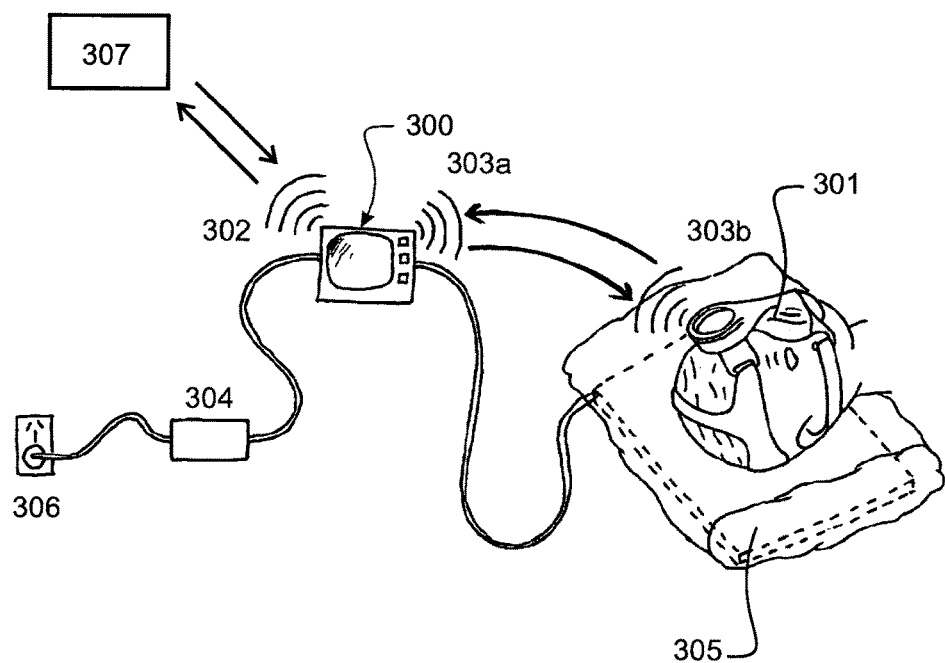
FIG. 44 shows a schematic view of a first embodiment base station in communication with a wearable respiratory assistance apparatus, and which drives a separate power supply mat for loose-coupled wireless power transfer to the respiratory assistance apparatus.

Referring to FIG. 44, in this first embodiment the base station 300 is in the form of a bedside module that is configured to be locatable near the user's bed, although it will be appreciated that the base station is portable such that is locatable in any suitable position that is in range of the respiratory device when being used. The base station comprises a data transfer system having one or more communication modules for communicating with the respiratory device 301 and other external devices or systems over any type of wireless communication medium, protocol or network, including, but not limited to Wi-Fi, Bluetooth, 3G cellular or similar, or alternatively using hardwired communication links. In this embodiment, the base station comprises a first communication module 302 that is configured to communicate with an external system 307 or network for transmitting compliance data to health service providers or other related parties regarding the user's use of the respiratory device. In this embodiment, the first communication module 302 of the base station communicates over a wireless medium with the external system 307, but alternatively a hardwired communication link or connection could be employed. For example, the base station may be connected to an external system, such as a Personal Computer, server, network such as a LAN or the like via a communication cable link using USB or Ethernet or similar. It will also be appreciated that the base station may alternatively be connected, wirelessly or via a hardwired connection, to a standalone communication or transmission device for sending data to another device or system.

The base station also comprises a second communication module 303a, which communicates, either wirelessly or via a hardwired connection, with a complementary communication module 303b onboard the respiratory device. The second communication module can be used to retrieve usage compliance data from the respiratory device for storage in the base station on an integrated data storage medium and/or further transmission to an external system as above. The second communication module 303a is also operable to send control signals to configure operating parameters or settings of the respiratory device. The base station comprises a control system for generating the control signals either automatically or in response to signals generated by a user interface that is operable by a user to control such operating parameters or settings via the second communication module 303a. By way of example, the control signals may be used to initiate various operational modes of the respiratory device including, but not limited to, on/off mode in which the device is switchable between on and off, charging mode in which the onboard power supply is charged, drying mode in which the blower unit is run for a predetermined time to dry the gases flow path after use, and data transfer mode when user usage data and/or sensor data is transferred to the base station.

In some embodiments, the control system may be configured to automatically send control signals to the respiratory device to control one or more of the operational modes based on whether an operative connection (wired or wireless) between the base station and respiratory device is detected, including initiating, halting or otherwise controlling the operational modes.

The second communication module 303a may optionally be configured to receive sensor signals and/or sensor data directly from any wireless sensors onboard the respiratory device.

Removable data storage media may also be provided on either or both of the respiratory device 301 and base station 300 to enable compliance data to be transferred.

The base station may be powered by a power supply such as a standalone AC power adaptor 304 that is coupled to a mains AC voltage supply 306. It will be appreciated that AC power adaptor circuitry may be integrated into the base station in alternative embodiments.

In this embodiment, the base station provides a power supply system in the form of a connected power supply mat 305 that is configured to transfer power to the un-tethered respiratory device 301 via wireless power transfer. In use, the power supply mat 305 is located under the user's pillow when they are wearing the respiratory device while sleeping for loose-coupled power transfer. The power received from the power supply mat may be used to power the respiratory device and/or charge any energy storage device onboard the respiratory device, such as battery packs, super-capacitors, or the like. In this embodiment, power is transmitted to the respiratory device 301 from the power supply mat 305 using magnetic resonance power transfer or similar methods.

The power supply system may also optionally be configured to directly power any wireless sensors onboard the respiratory device.

Second Embodiment Base Station—with Integrated Wireless Power Transfer

Figure 45:
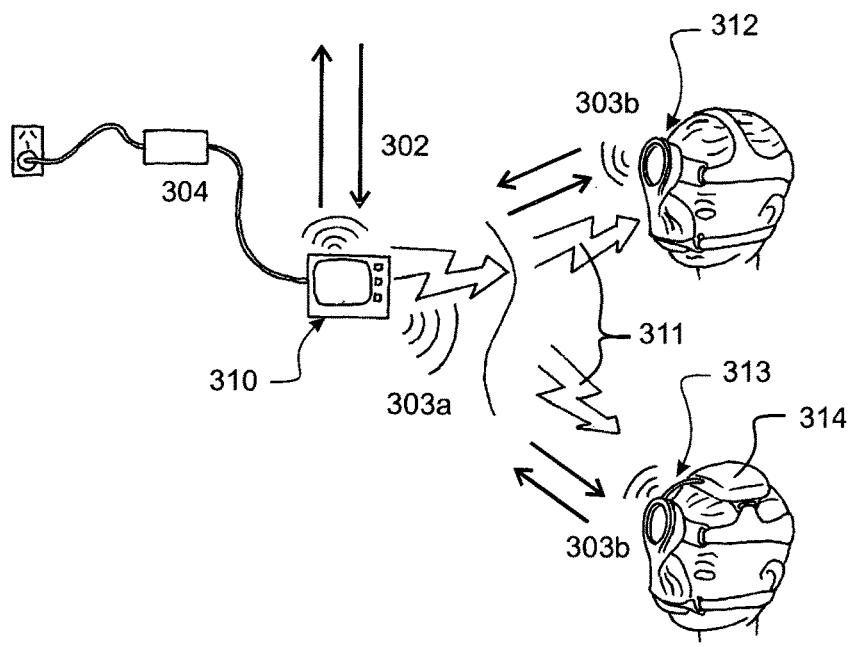
FIG. 45 shows a schematic view of a second embodiment base station providing direct data communication and wireless power transfer to a wearable respiratory assistance apparatus, and which shows by way of example two different embodiments of the wearable respiratory assistance apparatus, one with an onboard battery and one without.

Referring to FIG. 45, the second embodiment base station 310 is similar to the first and similar reference numerals represent similar features and functionality. The primary difference with the second embodiment is that the wireless power transfer hardware is integrated into the base station such that the data communications and power transfer can occur simultaneously across the same connection, i.e. the wireless connection medium between the base station and wearable respiratory device. As shown, the base station may wirelessly power 311 a wearable respiratory device 312 which does not have onboard energy storage (such as a battery pack or super-capacitors) or power and/or charge a wearable respiratory device 313 which does have onboard energy storage. As shown, the base station and respiratory devices also comprise communication modules as described in the first embodiment.

Third Embodiment Base Station—with Data Hub

Figure 46:
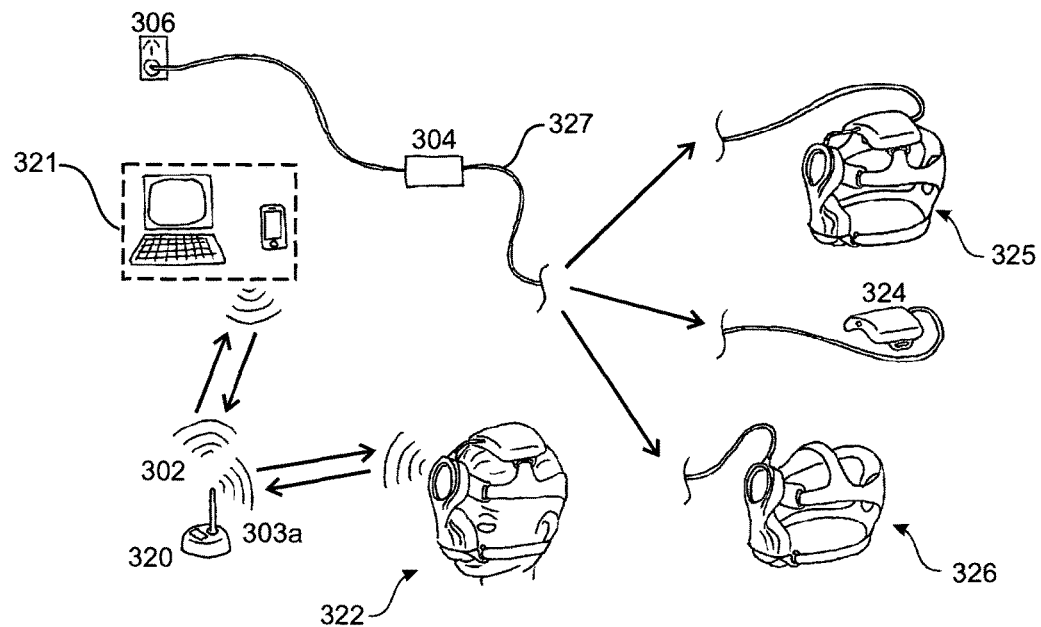
FIG. 46 shows a schematic view of a third embodiment base station in the form of a data hub in data communication with a wearable respiratory assistance apparatus, and additionally a separate power supply cable for powering and/or charging, and in particular showing various different powering and/or charging configurations for a wearable respiratory assistance apparatus having an onboard battery, a battery-less wearable respiratory assistance apparatus, or the charging of a removable battery from such an apparatus.

Referring to FIG. 46, the third embodiment base station is in the form of a data hub 320. The data hub 320 communicates with the respiratory device 322 over communication modules 303a,303b as before. The data hub 320 also communicates wirelessly 302 with an external system 321, such as a computer or portable communications device such as a laptop, tablet, smart phone or similar. A computer or application program running on the external system may be operable by a user to wirelessly control the settings or operating parameters of the respiratory device. It will be appreciated that the external system 321 and respiratory device 322 may communicate directly without the data hub 320 in alternative embodiments. As before, compliance data and device settings are relayed wirelessly from the respiratory device to the standalone data hub 320 for storage and or further wireless transmission to external systems. Removable media could also be used to transfer data for either of these two steps.

In this third embodiment configuration, a power supply 304, such as an AC adaptor connectable to the AC mains voltage 306, is connectable via a power cable 327 to the respiratory device components for powering or charging, ie the respiratory device is physically plugged into the power supply for operation and/or charging of any onboard energy storage devices. The intention is for the battery to be charged while the device is not in use, however the device can be used and charged simultaneously in a tethered mode of operation as shown at 325. Similarly the battery can be removed from the headgear/blower for charging as shown at 324 or the power supply may be directly plugged into the respiratory device for battery-less use as shown at 326. The power supply connection to the battery or respiratory device may contain a breakaway electrical connection to allow the cable to pull away from the battery or device if significant strain is applied.

Fourth Embodiment Base Station—with Battery Dock

Figure 47:
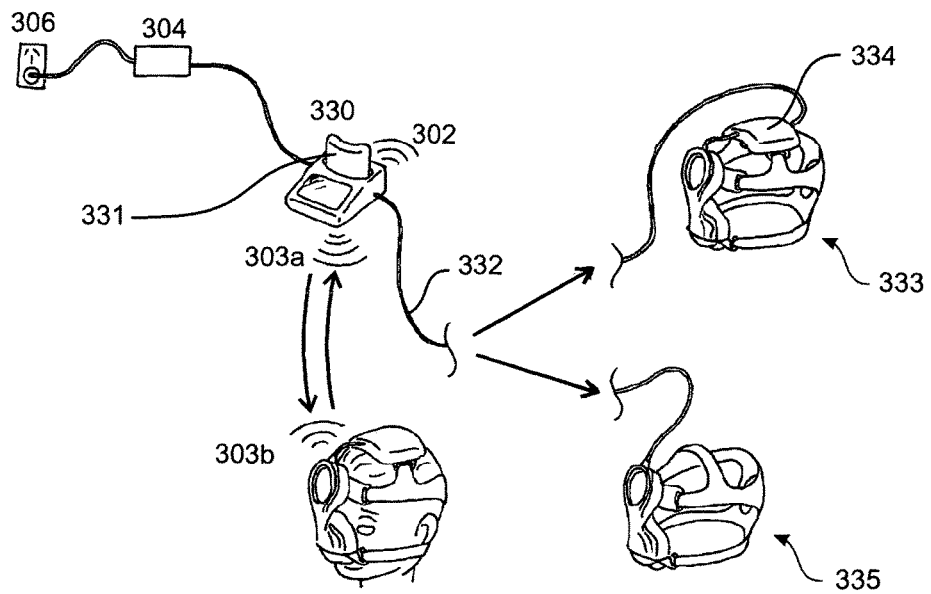
FIG. 47 shows a schematic view of a fourth embodiment base station in data communication with a wearable respiratory assistance apparatus, and which includes both a battery pack charging dock and a power supply cable for powering and/or charging, and in particular showing the powering and/or charging configurations for a wearable respiratory assistance apparatus having an onboard battery and a battery-less wearable respiratory assistance apparatus.

Referring to FIG. 47, the fourth embodiment base station 330 again comprises communication modules 302, 303 to enable the transmission and storage of compliance data, and to enable the user to change the respiratory device operation settings via a user interface on the base station.

The base station is powered by an AC adaptor 304 connected to the AC mains voltage supply 306, although it will be appreciated that the AC adaptor circuitry could alternatively be integrated into the base station. The base station comprises a battery dock for receiving a removable energy storage device of the respiratory device such as a battery or battery pack 331 for recharging, ie the battery is physically removed from the headgear of the respiratory device and docked into the base station to charge. A power cable 332 extends from the base station and is optionally connectable to the respiratory device for powering operation and/or charging. For example, the power cable 332 may be connected to a respiratory device 333 with an onboard battery 334 to allow tethered use of the respiratory device and simultaneous charging of the battery. Alternatively or additionally, the power cable may be plugged into a battery-less respiratory device as shown at 335 to allow tethered use of such a device. Again, the power cable connection to the battery or respiratory device may contain a breakaway electrical connection to allow the cable to pull away from the device if significant strain is applied.

Fifth Embodiment Base Station—with Integrated Wireless Power Transfer Mat

Figure 48:
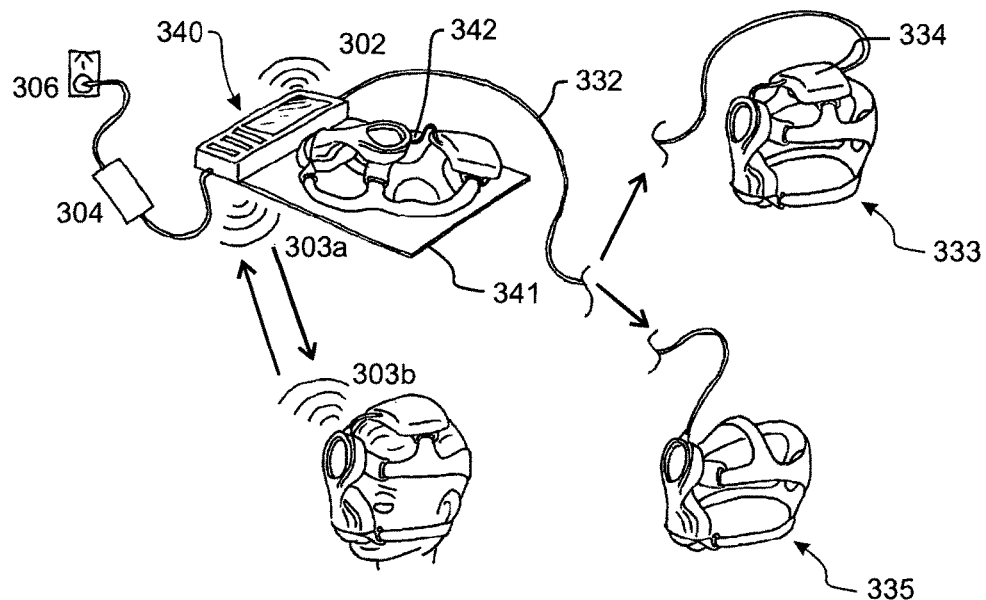
FIG. 48 shows a schematic view of a fifth embodiment base station in data communication with a wearable respiratory assistance apparatus, and which includes both an integrated power charging mat for wireless charging of the respiratory assistance apparatus and a power supply cable for powering and/or charging, and in particular showing the powering and/or charging configurations for a wearable respiratory assistance apparatus having an onboard battery and a battery-less wearable respiratory assistance apparatus.

Referring to FIG. 48, the fifth embodiment base station 340 has a configuration that is similar to the fourth embodiment and like reference numerals represent like features and functionality. The primary difference is that the fifth embodiment base station 340 does not have a battery dock, but is provided with an integrated power charging mat 341 of the type described in the first embodiment base station and which is configured to transfer power to the respiratory device 342 via wireless power transfer. For example, the battery of the respiratory device is physically placed on to the charging mat 341 to charge. Charging can occur either with the battery still attached to the respiratory device (as shown) or with the battery removed and placed on the mat by itself. The charging mat 341 can be open sided (as shown) or incorporated within an enclosure so the device is concealed while charging.

Sixth Embodiment Base Station—with Plug-in Charge

Figure 49:
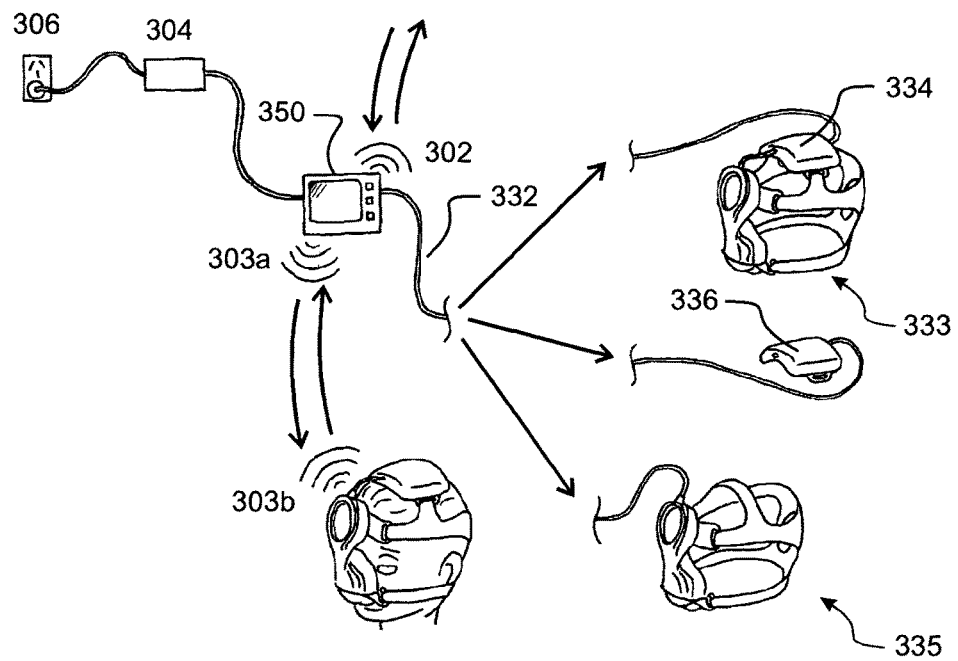
FIG. 49 shows a schematic view of a sixth embodiment base station in data communication with a wearable respiratory assistance apparatus, and which includes power supply cable for powering and/or charging, and in particular showing various different powering and/or charging configurations for a wearable respiratory assistance apparatus having an onboard battery, a battery-less wearable respiratory assistance apparatus, or the charging of a removable battery from such an apparatus.

Referring to FIG. 49, sixth embodiment base station 350 has a configuration that is similar to the fourth embodiment and like reference numerals represent like features and functionality. The primary difference is that the sixth embodiment base station 350 does not have a battery dock, but the power cable 332 is connectable to a removable battery pack 336 from the respiratory device if desired.

Figure 50:
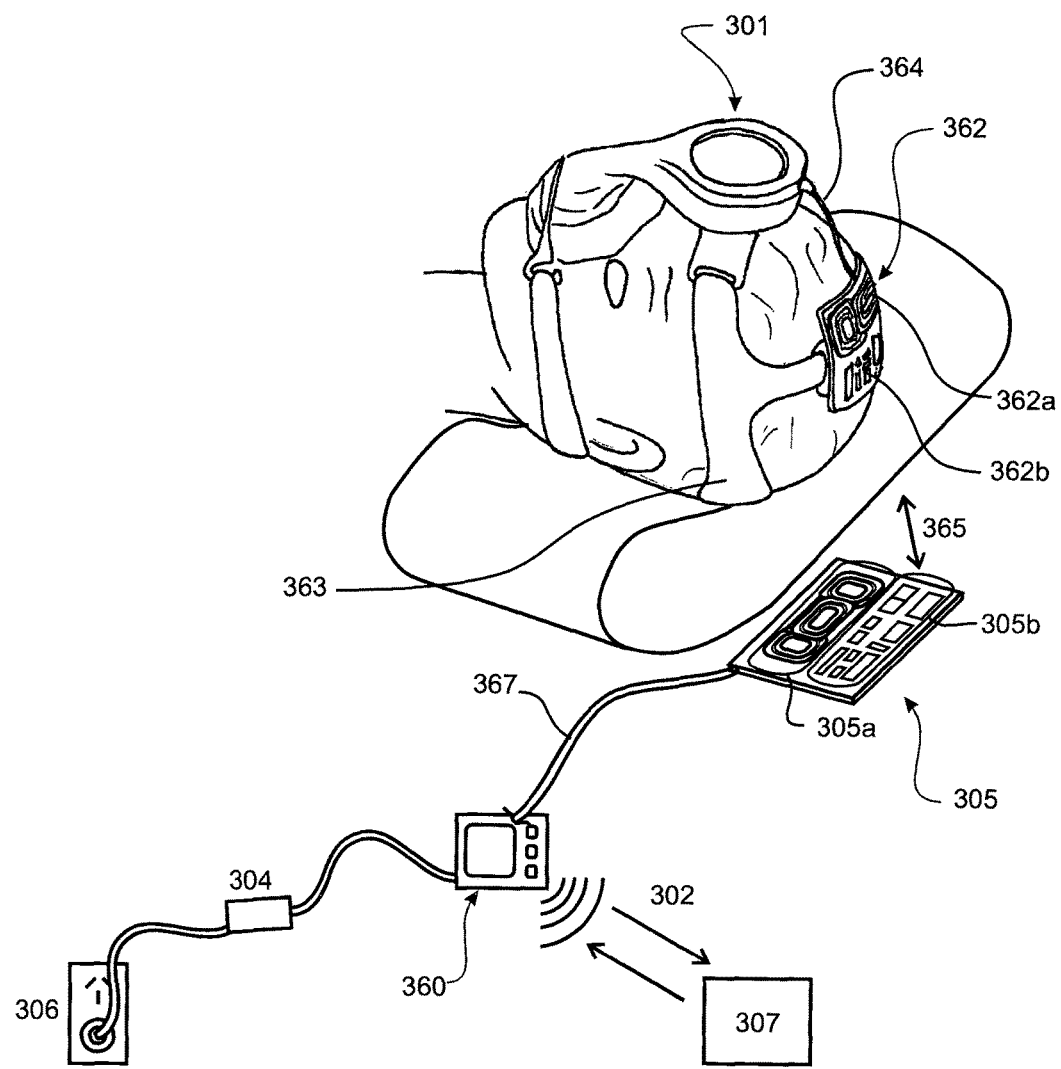
FIG. 50 shows a schematic view of a seventh embodiment base station in communication with a wearable respiratory assistance apparatus and directly via a separate power supply mat for loose-coupled wireless power transfer to the respiratory system apparatus.

Seventh Embodiment Base Station—with Separate Wireless Power and Data Transfer Mat Referring to FIG. 50, the seventh embodiment base station 360 is similar to the first and similar reference numerals represent similar features and functionality. The primary difference with the seventh embodiment is that the communication module for communicating with the respiratory device 301 is integrated into the power supply mat 305. In particular, the power supply mat 305 comprises both wireless power transfer transmitter or transmitter circuitry 305a and a communication module communication circuitry 305b. The wireless power transfer transmitter 305a is configured to provide loose-coupled power transfer to a complimentary wireless power transfer receiver or receiver circuitry 362a provided on a control board 362 of the respiratory device 301. Likewise, the control board also comprises a communication module communication circuitry 362b for communicating with the communication module 305b of the power supply mat 305. This configuration enables both power and data to be transferred from the power supply mat 305 to the respiratory device 301 across the same or single wireless connection medium or link 365.

As shown, the power transfer at 305 is connected via a cable 367 to the base station 360. This connection 367 enables the base station 360 to power the wireless power transfer circuitry of the power supply mat 305 and in addition to transmit and receive data to and from the respiratory device. In particular, the base station may send control signals to configure operating parameters or settings for the respiratory device and may retrieve usage compliance data from the respiratory device as described with reference to the first embodiment of the base station in FIG. 44.

The power received from the power supply mat may be used to power the respiratory device and/or charge any energy storage device on board the respiratory device, such as battery packs, super capacitors, or the like, as described in the first embodiment with reference to FIG. 44.

In this seventh embodiment, the control board 362 on board the respiratory device is shown mounted to the headgear 363 and in particular to the top headstrap in the location of the top of the user's head. The control board 362 is then connected via a cable 364 to the blower unit of the respiratory device 301 and/or any additional control circuitry in the blower unit housing. However, it will be appreciated that in alternative embodiments the control board 362 may be integrated into the main respiratory device housing rather than being mounted to the headgear as shown.

The foregoing description of the invention includes preferred forms thereof. Modifications may be made thereto without departing from the scope of the invention as defined by the accompany claims.

The invention claimed is:

1. A head-mounted respiratory assistance apparatus configured to provide a respiratory gases stream to a user, comprising:
   a main body securable to the head of a user;
   a blower unit provided on the main body having a gases inlet to receive a supply of gases from the surrounding atmosphere and which is operable to generate a pressurised gases stream at a gases outlet, wherein the blower unit comprises a casing and wherein the gases outlet extends radially outward from a center of the casing; and
   a patient interface provided on the main body having a gases inlet which is fluidly connected via a gases flow path to the gases outlet of the blower unit and which is configured to deliver the pressurised gases to the user's nose and/or mouth via one or more gases outlets,
   wherein the gases flow path from the gases inlet of the blower unit to the gases outlet(s) of the patient interface is substantially sealed such that there is zero bias flow along the gases flow path, and
   wherein the blower unit comprises a lightweight shroudless impeller, wherein the impeller comprises a plurality of separated impeller blades extending outward from a central hub of the impeller, and a motor with a rotatable drive shaft that is configured to rotate the impeller.

2. The head-mounted respiratory assistance apparatus according to claim 1 wherein the apparatus is configured to passively humidify and warm the pressurised respiratory gases in the gases flow path via accumulated heat and moisture build up within at least a portion of the gases flow path.

3. The head-mounted respiratory assistance apparatus according to claim 2 wherein the gases flow path is configured to accumulate heat and moisture build-up within at least a portion of the air flow path from exhaled gases from the user flowing back into the gases flow path from the patient interface.

4. The head-mounted respiratory assistance apparatus according to claim 2 further comprising one or more heat and moisture exchangers (HMEs) in the gases flow path of the respiratory assistance apparatus.

5. The head-mounted respiratory assistance apparatus according to claim 1 wherein the gases flow path volume between the gases inlet of the blower unit and the gases outlet(s) of the patient interface is less than approximately 200 mL.

6. The head-mounted respiratory assistance apparatus according to claim 5 wherein the gases flow path volume between the gases inlet of the blower unit and the gases outlet of the patient interface is in the range of approximately 50 mL to approximately 150 mL.

7. The head-mounted respiratory assistance apparatus according to claim 1 wherein the casing of the blower unit comprises upper and lower internal surfaces that enclose the impeller, and wherein the impeller has a plurality of blades that are substantially open to the upper and lower internal surfaces of the casing by virtue of being shroudless or otherwise having reduced material.

8. The head-mounted respiratory assistance apparatus according to claim 7 wherein the blower unit further comprises a partition to define first and second interior regions within the casing, the first region being defined by the casing and the partition and comprising the gases inlet and motor, the second region being defined by the casing and the partition and comprising the impeller, and wherein the first and second regions are fluidly connected by an opening formed in or by the partition.

9. The head-mounted respiratory assistance apparatus according to claim 8 wherein the impeller has an axis of rotation, the partition extending radially from the axis of rotation.

10. The head-mounted respiratory assistance apparatus according to claim 8 wherein the casing further comprises a volute that is fluidly connected to the second region by an air passage, and wherein the gases outlet of the blower unit is proximate the periphery of the volute.

11. The head-mounted respiratory assistance apparatus according to claim 1 wherein the motor of the blower unit comprises: a stator, and at least one bearing structure to support the rotatable drive shaft within the stator, the bearing structure comprising one or more bearings that are supported by one or more bearing mounts about an axis of the rotatable drive shaft.

12. The head-mounted respiratory assistance apparatus according to claim 11 wherein the stator comprises a stator frame, and an outer portion of the one or more bearing mounts engages the stator and/or an inner surface of the stator frame.

13. The head-mounted respiratory assistance apparatus according to claim 12 wherein the one or more bearing mounts are flexible and/or resilient, and wherein the one or more bearing mounts have a curved annular body and when engaged with the stator and/or stator frame, the annular body is coerced into an engaged configuration that provides preload to the one or more bearings.

14. The head-mounted respiratory assistance apparatus according to claim 11 wherein the blower unit further comprises a motor mount that couples the stator and the casing to provide compliant support to the motor.

15. The head-mounted respiratory assistance apparatus according to claim 11 wherein the rotatable drive shaft is plastic.

16. The head-mounted respiratory assistance apparatus according to claim 15 wherein the motor further comprises a rotor within the stator, and wherein the plastic rotatable drive shaft is formed and coupled to the rotor by injection moulding.

17. The head-mounted respiratory assistance apparatus according to claim 1 wherein the gases inlet of the patient interface is fluidly connected to a tubular connector of the gases outlet of the blower unit.

18. The head-mounted respiratory assistance apparatus according to claim 1 wherein the gases outlet of the blower unit comprises an outlet aperture that extends radially outward from the center of the casing and extends outwardly from a peripheral wall of the casing.

19. The head-mounted respiratory assistance apparatus according to claim 1 wherein a surface of each of the plurality of separated impeller blades is parallel to an axis of rotation of the impeller.

20. The head-mounted respiratory assistance apparatus according to claim 1 wherein each of the plurality of separated impeller blades comprises a forward swept blade tip.

* * * * *

UNITED STATES PATENT AND TRADEMARK OFFICE
CERTIFICATE OF CORRECTION

PATENT NO. : 10,137,264 B2
APPLICATION NO. : 14/376381
DATED : November 27, 2018
INVENTOR(S) : Adam John Darby et al.

It is certified that error appears in the above-identified patent and that said Letters Patent is hereby corrected as shown below:

In the Specification

Column 5, Line 53, change "Preferably" to --preferably--.

Column 8, Line 58-59, change "apparatus" to --apparatus.--.

Column 25, Line 27, change "90,90a," to --90, 90a,--.

Column 28, Line 15, change "90,90a," to --90, 90a,--.

Column 31, Line 53, change "acety" to --acetyl--.

Column 38, Line 21, change "303a,303b" to --303a, 303b--.

Column 38, Line 32, change "and or" to --and/or--.

Signed and Sealed this
Nineteenth Day of May, 2020

Andrei Iancu
*Director of the United States Patent and Trademark Office*